US006930175B1

(12) United States Patent
Pasternack et al.

(10) Patent No.: US 6,930,175 B1
(45) Date of Patent: Aug. 16, 2005

(54) GENE FAMILY WITH TRANSFORMATION MODULATING ACTIVITY

(75) Inventors: Gary R. Pasternack, Baltimore, MD (US); Gerald J. Kocheavar, College Station, TX (US); Jonathan R. Brody, Potomac, MD (US); Shrihari S. Kadkol, Ellicott City, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 368 days.

(21) Appl. No.: 09/591,500

(22) Filed: Jun. 12, 2000

Related U.S. Application Data

(63) Continuation of application No. PCT/US98/26433, filed on Dec. 11, 1998.
(60) Provisional application No. 60/069,677, filed on Dec. 12, 1997.

(51) Int. Cl.$^7$ .............................................. C07K 16/18

(52) U.S. Cl. ................................ 530/388.1; 530/387.1

(58) Field of Search .......................... 530/387.1, 381.7, 530/387.9, 388.1, 388.8

(56) References Cited

U.S. PATENT DOCUMENTS

| | | | |
|---|---|---|---|
| 4,874,845 A | 10/1989 | Saito et al. | |
| 4,889,818 A | 12/1989 | Gelfand et al. | |
| 5,200,313 A | 4/1993 | Carrico | |
| 5,527,884 A | 6/1996 | Russell et al. | |
| 5,726,018 A | 3/1998 | Pasternack | |
| 5,734,022 A | 3/1998 | Pasternack | |
| 5,756,676 A | 5/1998 | Pasternack | |
| 5,874,234 A | 2/1999 | Pasternack | |
| 6,040,173 A | 3/2000 | Pasternack | |
| 2003/0129631 A1 | 7/2003 | Pasternack et al. | |

FOREIGN PATENT DOCUMENTS

| | | |
|---|---|---|
| EP | 0375408 | 6/1990 |
| WO | WO 92/02554 | 2/1992 |
| WO | 9403594 | 2/1994 |
| WO | 9610092 | 4/1996 |
| WO | WO 99/29906 | 6/1999 |

OTHER PUBLICATIONS

Rebel, et al., "Human pp32 pseudogene," Gen Bank Accession No. U71084, Apr. 3, 1997.
Kochevar, et al., "*Homo sapiens* candidate tumor suppressor pp32r1 (PP32R1) gene," Gene Bank Accession No. AF008216, Feb. 5, 199.
Norbert Zilka et al., "A rapid immunohistochemical primary screening assay for hybridomas," Journal of Immunological Methods 9223 (2002) pp. 1–5.

Geert Van Leenders et al., "Demonstration of Intermediate Cells during Human Prostate Epithelial Differentation In Situ and In Vitro Using Triple–Staining Confocal Scanning Microscopy," Laboratory Investigation, Aug. 2000, vol. 80, No. 8, pp. 1251–1258.
Xiongwen Zhang et al., "Apoptosis induction in prostate cancer cells by a novel gene product, pHyde, involves caspase–3," Oncogene (2000) 20, pp. 5982–5990.
Valerio Orlando, "Polycomb, Epigenomes, and Control of Cell Indentity," Cell, vol. 112, pp. 599–606, Mar. 7, 2003.
Antoni Matilla et al., "The cerebellar leucine–rich acidic nuclear protein interacts with ataxin–1,"Nature, 389, pp. 818, 974–978, 604–607, 1997.
Asok Mukhopadhyay et al., "Curcumin downregulates cell survival mechanisms in human prostate cancer cell lines," Oncogene (2001) 20, 7597–7609.
Kazuo Oba et al., "Two putative tumor suppressor genes on chromosome arm 8p may play different roles in prostate cancer," Cancer Genetics and Cytogenetics 124 (2001), pp. 20–26.
G. J. L. H. Van Leenders et al., "Stem cell differentiation within the human prostate epithelium: implications for prostate carcinogenesis," BJU International (2001), 88(Suppl. 2), pp. 35–42.
Martin Radrizzani et al., "Differential expression of CPD1 during postnatal development in the mouse cerebellum," Brain Research 907 (2001), pp. 162–174.
Mitchell S. Steiner et al., "Growth Inhibition of Prostate Cancer by an Adenovirus Expressing a Novel Tumor Suppressor Gene, pHyde$^1$," Cancer Research 60, pp. 4419–4425, Aug. 15, 2001.
Josephine N. Harada et al., "Analysis of the Adenovirus E1B–55K–Anchores Proteome Reveals Its Link to Ubiquitination Machinery," Journal Of Virology, Sep. 2002, vol. 76, No. 18, pp. 9194–9206.

(Continued)

*Primary Examiner*—Larry R. Helms
*Assistant Examiner*—Misook Yu
(74) *Attorney, Agent, or Firm*—Hunton & Williams LLP

(57) ABSTRACT pp32 is a member of a highly conserved family of differentiation-regulated nuclear proteins that is highly expressed in nearly all human prostatic adenocarcinomas of Gleason Grade ≧ 5. This contrasts with the low percentage of prostate tumors that express molecular alterations in proto-oncogens or demonstrate tumor suppressor mutation or loss of heterozygosity. By analysis of specimens of human prostatic adenocarcinoma and paired adjacent normal prostate from three individual patients, the inventors have shown that normal prostate continues to express normal pp32, whereas three of three sets of RT-PCR-amplified transcripts from prostatic adenocarcinomas display multiple cancer-associated coding sequence changes. The cancer-associated sequence changes appear to be functionally significant. Normal pp32 exerts antineoplastic effects through suppression of transformation. In contrast, cancer-associated pp32 variants augment, rather than inhibit, transformation.

2 Claims, 27 Drawing Sheets

OTHER PUBLICATIONS

Monica Holmberg et al., Spinocerebellar ataxia type 7 (SCA7): a neurodegenerative disorder with neuronal intranuclear inclusions, Human Molecular Genetics, 1998, vol. 7, No. 5, pp. 913–918.

Xuejun Jiang et al., "Distinctive Roles of PHAP Proteins and Prothymosin–α in a Death Regulatory Pathway," Science, vol. 299, Jan. 10, 2003, pp. 223–226.

M. Jiang et al., Molecular cloning and characterization of a novel human gene (ANP32E alias LANPL) from human fetal brain, Cytogenet Genome Res. 97:68–71 (2002).

Maarten R. Leerkes et al., "In Silico Comparsion of the Transcriptome Derived from Purified Normal Breast Cells and Breast Tumor Cell Lines Reveals Candidate Upregulated Genes in Breast Tumor Cells," Genomics, vol. 79, No. 2, Feb. 2002, pp. 257–265.

Zusen Fan et al., "Tumor Suppressor NM23–H1 Is a Granzyme A–Activated Dnase during CTL–Mediated Apotosis, and the Nucleosome Assembly Protein SET Is Its Inhibitor," Cell, vol. 112, pp. 659–672, Mar. 7, 2003.

Samer W. K. Al–Murrani et al., "Expression of $I_2$ PP2A, an inhibitor of protein phosphatase 2A, induces c–Jun AND AP–1 activity," Biochem. J. (1999) 341, pp. 293–298.

C. M. Brennan et al., "HuR and Mma stability," CMLS Cell. Mol. Life Sci. 58 (2001), pp. 266–277.

Fusheng Li et al., Ataxin–3 Is a Histone–binding Protein with Two Independent Transcriptional Corepressor Acivities, The Journal Of Biological Chemistry, vol. 277, No. 47, Issue of Nov. 22, pp. 45004–45012, 2002.

Ji–Chun Xue et al., "Idenitification of a Novel Testis–Specific Leucine–Rich Protein in Humans and Mice," Biology of Reproduction 62, pp. 1278–1284 (2000).

Kadkol et al., "Novel Nuclear Phosphoprotein pp32 Is Highly Expressed in Intermediate–and High–Grade Prostate Cancer," The Prostate 34:231–237 (1998).

Chen et al., "Structure of pp32, an Acidic Nuclear Protein With Inhibits Oncogene–induced Formation of Transformed Foci," Molecular Biology of the Cell, vol. 7, 2045–2046, Dec. 1996.

Parker et al., "Cancer Statistics, 1996," CA, a Cancer Journal for Clinicians, 46:5–27, 1996.

Potosky et al., "The Role of Increasing Detection in the Rising Incidence of Prostate Cancer," JAMA, 273(7)548–552, 1995.

Fleming et al., "Expression of the c–myc Protooncogene in Human Prostatic Carcinoma and Benign Prostatic Hyperplasia," Cancer Research, 46:1535–1538, 1986.

Visakorpi et al., "Genetic Changes in Primary and Recurrent Prostate Cancer by Comparative Genomic Hybridization," Cancer Research, 55:342–347, 1995.

Gusev et al., "pp32 overexpression induces nuclear pleomorphism in rat prostatic carcinoma cells," Cell Proliferation, 29:643–653, 1996, Blackwell Science, Ltd.

Walensky et al., "A Novel M, 32,000 Nuclear Phosphoprotein Is Selectively Expressed in Cells Competent for SelfRenewal," Cancer Research, 53:4720–4726, 1993.

Vaesen et al., "Purification and Characterization of Two Putative HLA Class II Associated Protein: PHAPI and PHAPII," Biol. Chem. Hoppe–Seyler, 375:113–126, 1994, Walter de Gruyter & Co.

Fink et al., "Localization of the Gene Encoding the Putative Human HLA Class II–Associated Protien (PHAPI) to Chromosome 15q22.3–q23 by Flurescence in Situ Hybridization," Genomics, 29:309–310, 1995, Academic Press, Inc.

Li et al., "Molecular Identification of $1_1^{PP2A}$, a Novel Potent Heat–Stable Inhibitor Protien of Protein Phosphatase 2A," Biochemistry, 35:6998–7002, 1996, American Chemical Society.

Ulitzur et al,. "Biochemical Characterization of Mapmodulin, a Protein That Binds Microtuble–associated Protiens," Journal o fBiological Chemistry, 272:30577–30582, 1997, The American Society for Biochemistry and Molecular Biology, Inc.

Matsuoka et al., "A nuclear factor containing the leucine–rich repeats expressed in murine cerebellar neurons," Proc. Natl. Acad. Sci. USA, 91:9670–9674, 1994.

Mencinger et al., "Expression analysis and chromosomal mapping of a novel human gene, APRIL, encoding an acidic protein rich in leucines," Biochimica et Biophysica Acta., 1395:176–180, 1998, Elsevier Science B.V.

Malek et al., "Identification and Preliminary Characterization of Two Related Proliferation–associated Nuclear Prosphoprotiens," J. Biol. Chem., 265:13400–13409, 1990, The American Society for Biochemistry and Molecular Biology, Inc.

Isaacs et al., "Genetic Alterations in Prostate Cancer," Cold Spring Harbor Symposia on Quantitative Biology, 59:653–659, 1994, Cold Spring Harbor Lab Press.

Chen et al., "Structure of pp32, an Acidic Nuclear Protein Which Inhibits Oncogene–induced Formation of Transformed Foci," Molecular Biology of the Cell, 7:2045–2056, 1996, The American Society for Cell Biology.

Cattoretti et al., "Antigen Unmasking on Formalin–Fixed, Paraffin–Embedded Tissue Sections," Journal of Pathology, 171:83–98, 1993, John Wiley & Sons, Inc.

(Abstract) Anderson et al., "Tissue Specific Isoforms of Erythroid Protien 4.1,"Spectrin–Associated Protiens, item No. 2032, J. Cell Biol., 103: p. 542a.

(Abstract) Pasternack et al., "Protein 4.1 as a Myosin Binding and Modulating Protien: Insights into a new functional class of protiens," Cellular and Molecular Biology of Normal and Abnormal Erythroid Membranes, J. Cell Biochem,. Suppl. 13, Part B, pp. 209.

Krauss et al., "Structural protein 4.1 is located in mammalian centrosomes," Proc. Natl. Acad. Sci. USA 94:7297–7302 (1997), the National Academy of Sciences.

Chen, et al., 1989, "Phosphorylation of Retinoblatoma Gene Product is Modulated During the Cell Cycle and Cellular Differentiation," Cell, 58:1193–1198, Cell Press.

Cooper, et al., "RB and the Cell Cycle: Enterance or Exit?" 1989, Cell, 58:10009–1011, Cell Press.

Feuerstein, et al., 1988, "The Nuclear Matrix Protein, Numatrin (B23), Is Associated With Growth Factor–Induced Mitogenesis in Swiss 3T3 Fibroblasts and with T Lymphocyte Proliferation Stimulated by Lectins and Anti–T Cell Antigen Receptor Antibody," J. Cell Biol., 107:1629–1642, the Rockefeller University Press.

Gerdes, et al., 1984, "Cell Cycle Analysis of a Cell Proliferation–Associated Human Nuclear Antigen Defined by the Monoclonal Antibody Ki–67,"J. Immunol., 133:1710–1715, the American Association of Immunologists.

Gomez–Marquez, et al., 1989, "The Expression of Prothymosin β Gene in T Lymphocytes and Leukemic Lymphoid Cells Is Tied to Lymphocyte Proliferation," J. Biol. Chem., 264:8451–8454, The American Society for Biochemistry and Molecular Biology, Inc.

Morla, et al., 1989, "Reversible Tyrosine Phosphorylation of cdc2: Dephosphorylation Accompanies Activation During Entry into Mitosis," Cell, 58:193, Cell Press.

Shawver, et al., 1989, "Platelet–Derived Growth Factor Induces Phosphorylation of a 64–kDa Nuclear Protein," J. Biol. Chem., 264:1046–1050, the American Society for Biochemistry and Molecular Biology, Inc.

Tan, et al., 1987, "Autoantibody to the Proliferating Cell Nuclear Antigen Neutralizes the Activity of the Auxillary Protein for DNA Polymerase Delta," Nucleic Acids Res., 15:9299–9308, IRL Press Limited, Oxford, England.

Whelly, et al., 1977, "Relationship Between Cell Proliferation, Chromatin Template Activity And Accumulation of Nuclear Proteins," Cell Biol. Int. Rep., 1:13–21.

Ackerman, et al., 1985, "Phosphorylation of DNA Topisomerase II by Casein Kinase III: Modulation of Eukaryotic Topoisomerase II Activity in vitro," Proc. Natl. Acad. Sci., USA, 82:3164–3168.

Ackerman, et al., 1989, "Regulation of Casein Kinase II Activity by Epidermal Growth Factor in Human A–431 Carcinoma Cells," J. Biol. Chem., 264:11958–11965, the American Society for Biochemistry and Molecular Biology, Inc.

Duceman, et al., 1981, "Activation of Purified Hepatoma RNA Polymerase I by Homologous Protein Kinase NII," J. Biol. Chem., 256:10755–10758.

Durban, et al., 1985, "Topoisomerase I Phosphorylatoin in vitro and in Rapidly Growing Novikoff Hepatoma Cells," EMBO J., 4:2921–2926, IRL Press Limited, Oxford, England.

Friedman, et al., 1985, "Nuclear Protein Phosphorylation in Isolated Nuclei from HeLa Cells. Evidence that $^{32}P$ Incorporation from $[\gamma-^{32}]$ GTP is Catalyzed by Nuclear Kinase II," Biochem. Biophys. Acta, 847:165–176, Elsevier Science Publishers B.V.

Holcomb, et al., 1984, "Phosphorylation of the C–Proteins of HeLa Cell hnRNP Particles," J. Biol. Chem., 259:31–40, the American Society of Biological Chemists, Inc.

Klarlund, et al., 1988, "Insulin–Like Growth Factor I and Insulin Rapidly Increase Casein Kinase II Activity in BALB/c 3T3 Fibroblasts," J. Biol. Chem., 263:15872–15875, the American Society for Biochemistry and Molecular Biology, Inc.

Matthews, et al., 1984, "Nuclear Protien Kinases," Mol. Cell. Biochem., 59:81–99, Martinus Nijhoff Publishers, Boston, Mass., Printed in the Netherlands.

Pfaff, et al., 1988, "Casein Kinase II Accumulation in the Nucleolus and Its Role in Nucleoar Phosphorylation," Biochem. Biophys. Acta, 969:100–109, Elsevier Science Publishers B.V.

Sommercorn, et al., 1987, 1 "Activation of Casein Kinase II in Response to Insulin and to Epidermal Growth Factor," Proc. Natl. Acad. Sci., USA, 84:8834–8838.

Stetler, et al., 1982, "Phosphorylation of Deoxyridonucleic Acid Dependent RNA Polymerase II by Nuclear Protein Kinase NII: Mechanism of Enhanced Ribonucleic Acid Synthesis," Biochemistry, 21:3721–3728, American Chemical Society.

Walton, et al., 1985, "Phosphorylation of High Mobility Group Protien 14 by Casein Kinase II," J. Biol. Chem., 260:4745–4750, the American Society of Biological Chemists, Inc.

Eliyahu, et al., 1989, "Wild–Type p53 Can Inhibit Oncogene–Mediated Focus Formation," Proc. Natl. Acad. Sci., USA, 86:8763–8767.

Ginsberg, et al., 1991, "Transfected Mouse c–jun Can Inhibit Transformation of Primary Rat Embryo Fibroblasts," Oncogene, 6:669–672, Macmillan Press Limited.

Land, et al., 1983, "Tumorigenic Conversion of Primary Embryo Fibroblasts Required At Least Two Cooperating Oncogenes," Nature, 304:396–602, Macmillan Journals Ltd.

Makela, et al., 1992, "Alternative Forms of Max as Enhancers or Suppressors of Myc–Ras Cotransformation," Science, 256:373–377.

Resar, et al., 1993, "B–Myc Inhibits Neoplastic Transformation and Transcriptional Activation by c–Myc," Mol. Cell. Biol., 13:1130–1136, American Society for Microbiology.

Van Den Heuvel, et al., 1993, "Large E1B Protiens of Adenovirus Types 5 and 12 Have Different Effects of p53 and Distinct Roles in Cell Transformation," J. Virol., 67:5226–5234, American Society for Microbiology.

Yehiely, et al., 1992, "The Gene for the Rat Heat–Shock Cognate, hsc 70, Can Suppress Oncogene–Mediated Transformation," Cell. Growth Diff., 3:803–809.

Alnemri, et al., 1992,"Overexpressed Full–Length Human BCL2 Extends the Survival of Baculovirus–Infected S19 Insect Cells,"Proc. Natl. Acad. Sci, USA, 89–7295–7299.

Buttyan, R., 1991, "Genetic Response of Prostate Cells to Androgen Deprivation: Insights Into the Cellular Mechanism of Apoptosis," in Apoptosis, in Apoptosis: The Molecular Basis of Cell Death, J. Inglis, et al, eds., Cold Spring Harbor, NY: Cold Spring Harbor Laboratory Press, pp. 157–173.

De Jong, et al., 1994, "Subcellular Localization of the bcl–2 Protein in Malignant and Normal Lymphoid Cells,"Cancer Res., 54:256–260.

Gerschenson, et al., 1991, "Apoptosis and Cell Proliferation are Terms of the Growth Equation," in Apoptosis: The Molecular Basis of Cell Death, J. Inglis, et al, eds., Cold Spring Harbor, NY: Cold Spring Harbor Laboratory Press, pp. 175–192.

Hockenbery, et al., 1991, "BCL2 Protien is Topographically Restricted in Tissues Characterized by Apoptic Cell Death," Proc. Natl. Acad. Sci., USA, 88:6961–6965.

Kerr, et al., 1991, "Definition and Incidence of Apoptosis: An Historical Perspective,"in Apoptosis: The Molecular Basis of Cell Death, J. Inglis, et al, eds., Cold Spring Harbor Laboratory Press, pp. 5–29.

Martin, et al., 1994, "Dicing With Death: Dissecting the Components of the Apoptosis Machinery," Trends Biochem. Sci., 19:26–30.

Wagner, et al., 1993, "Myc–Mediated Apoptosis is Blocked By Ectopic Expression of Bcl–2," Mol. Cell. Biol., 13:2432–2440, American Society for Microbiology.

Briggs, et al., 1992, "Nuclear Morphometry for Prediction of Metastatic Potential in Early Squamous Cell Carcinoma of the Floor of the Mouth," Arch. Otolaryngol Head. Neck. Surg., 118:531–533.

Dawson, et al., 1991, "Nuclear Grading of Breast Carcinoma by Image Analysis, Classification by Multivariate and Neural Network Analysis," Am. J. Clin. Pathol., 95:S29–S37.

Diamond, et al., 1982 "A New Method To Assess Metastatic Potential of Human Prostate Cancer: Relative Nuclear Roundness," J. Urol., 128:729–734, the Williams & Wilkins Co., Printed in the U.S.

Diamond, et al., 1982, "Computerized Image Analysis of Nuclear Shape as a Prognostic Factor for Prognostic Factor for Prostatic Cancer," The Prostate, 3:321–332, Alan R. Liss, Inc.

Drescher, et al., 1993, "Prognostic Significance of DNA Content and Nuclear Morphology in Borderline Ovarian Tumors," Gynecol. Oncol., 48:242–246, Academic Press Inc.

Epstein, et al., 1984, "Nuclear Roundness Factor. A Predictor of Progression in Untreated State A2 Prostate Cancer," Cancer, 54:1666–1671.

Fleming, et al., 1990, "Image Analysis Cytometry of Dysplastic Nevi,"J. Invest. Dermatol., 95–287–291, the Society for Investigative Dermatology, Inc.

Galera–Davidson, et al., 1990, "Cytophotometric DNA Measurements in Medullary Thyroid Carcioma," Cancer, 65:2255–2260.

Hill, et al., 1989, "The Proportion of Stem Cells in Murine Tumors," Int. J. Radiat. Oncol. Biol. Phys., 16:513–518, Pergamon Press Inc., Printed in the U.S.

Murphy, et al., 1990, "Nuclear Shape Analysis for Assessment of Prognosis in Renal Cell Carcinoma," J. Urol., 143:1103–1107, American Urological Association, Inc.

Partin, et al., 1990, "Nuclear Morphometry as a Predictor of Response to Therapy in Wilms Tumor: A Preliminary Report," J. Urol., 144:952–954, American Urological Association, Inc.

Pienta, et al., 1991, "Correlation of Nuclear Morphometry with Progression of Breast Cancer," Cancer, 68:2012–2016.

Rickaert, et al., 1992, "Computerized Morphonuclear Characteristics and DNA Content of Adenocarcinoma of the Pancreas, Chronic Pancreatitis, and Normal Tissues: Relationship with Histopathologic Grading," Hum. Pathol., 23:1210–1215, W.B. Saunders Co.

Van Etten, et al., 1989, "The Mouse Type IV c–abl Gene Product Is a Nuclear Protein, and Activation of Transforming Ability is Associated with Cytoplasmic Localization," Cell 58:669–689, Cell Press.

Aster, et al., 1986, "The 4.1 Like Proteins Closely Related in Structure to Red Blood Cell Protein 4.1" J. Cell Biol., 103:115–122, the Rockefeller University Press of the Bovine Lens: Spectrin–binding Proteins.

Anderson, et al., 1998, "Tissue–Specific Analouges of Erthrocyte Protein 4.1 Retain Functional Domains," J. Cell. Biochem., 37:269–284, Alan R. Liss, Inc.

Aster, et al., 1984, "Identification of Spectrin and Protein 4.1–Like Proteins In Mammalian Lens," Biochem. Biophys. Res. Comm., 119:726–734, Academic Press Inc.

Aster, et al., 1986, "THe 4.1 Like Proteins Closely Related in Structure to Res Blood Cell Protiens Closely Related in Structure to Red Blood Cell Protien 4.1" J. Cell Biol., 103:115–122, the Rockefeller University Press.

Bourguignon, et al., 1986, "Lymphoma Thy–1 Glycoprotein Is Linked to the Cytoskeleton via a 4.1–Like Protein,"J. Cell Biol., 103:2529–2540, the Rockefeller University Press.

Cho, et al., 1988, "Antibodies to Cytoskeletal Erythrocyte Protein 4.1 Recognizes Domain Specific Proteins of the Hepatocyte Plasma Membrane in Isolated Hepatocyte Couplets," Gastroenterology, 94:A529.

Cohen, et al., 1982, "A Protein Immunologically Related To Erythrocyte Band 4.1 is Found On Stress Fibres of Non-Erythroid Cells." Nature, 299:648–650, Macmillan Journals Ltd.

Constantinescu, et al., 1986, "Immunological Detection of An Analogue of the Erthroid Protien 4.1 In Endothelial Cells," Cell Biol. Intl. Rept., 10:861–868.

Correas, Isabel, 1991, "Characterization of Isoforms of Protein 4.1 Present in the Nucleus," Biochem. J., 279:581–585, Printed in Great Britain.

Davies, et al., 1985, "Platelets Contain Proteins Immunologically Related to Red Cell Spectrin and Protein 4.1," Blood, 65:52–59, Grune & Stratton Inc.

De Cesaris, et al., 1989, "Spectrin, Fodrin and Protein 4.1–Like Protiens In Differentiating Rat Germ Cells," Differentiation, 41:216–222, Springer–Verlag.

Goodman, et al., 1984 "Identification and Location of Brain Protein 4.1," Science, 224:1433–1436.

Spencer, et al., 1990, "Membrane Skeleton Protein 4.1. in Developing Xenopus: Expression In Postmitotic Cells of the Retina," Developmental Biology, 139:279–291, Academic Press Inc.

Spiegal, et al., 1984, "An Analogue of the Erthroid Membrane Skeletal Protein 4.1 In Nonerythroid Cells," J. Cell Biol., 99:886–893, the Rockefeller University Press.

Stevenson, et al., 1989, "Fodrin and Band 4.1 in a plasma Membrane–Associated Fraction of Human Neutrophils," Blood, 74:2136–2143, Grune & Stratton Inc.

Tang, et al., 1998, "Translation of an mRNA Species Encoding Non–Erthroid Protein 4.1 Generates Two Proteins One of which May Be Localized In The Nucleus," Clin. Res., 36:405a.

Tang, et al., 1998, "Expression of Specific Isoforms of Protein 4.1 in Erythroid and Non–Erthroid Tissues,"Adv. Exp. Med. Biol., 241:81–95.

Tang, et al., 1988, "Selective Expression of an Erythroid-Specific Isoform of Protien 4.1," Proc. Natl. Acad. Sci., USA, 85–3713–3717.

Tang, et al., 1990, "Membrane Skeletal Protein 4.1 Of Human Erythroid and Non–Erythroid Cells Is Composed Of Multiple Isoforms With Novel Sizes, Functions and Tissue Specific Expression," Cell. Molec. Biol. of Normal and Abnormal Erythroid Membrane, Alan R. Liss, Inc. New York, pp. 43–59.

Tang, et al., 1990, "Heterogeneity of mRNA and Protein Products Arising From the Protein 4.1 Gene in Erythroid and Nonerythroid Tissues," J. Cell. Biol., 110:617–624, the Rockefeller University Press.

Ziparo, et al., 1986, "Proteins of the Membrane Skeleton In Rat Sertoli Cells," J. Cell. Sci., 86:145–154, the Company of Biologists Ltd., Printed in Great Britain.

Sonoda et al., "Complete Nucleotide Sequence of Human Phosphoribosyl Pyrophosphate Synthetase Subunit I (PRSI) cDNA and a Comparison with Human and Rat PRPS Gene Families," The Journal of Biochemistry. vol. 109., No. 2, pp. 361–364, Feb. 1991.

ATTC/NIH Repository Catalogue of Human and Mouse DNA/Probes and Libraries, Eighth Edition, pp. 1–58 and 63–70, 1994.

(Abstract) Paternack et al., "Murine Lymphocytes Express a Novel Form of Protein 4.1", Spectrin–associated Proteins, J. Cell Biol., 103: 543a, item No. 2035.

(Abstract) Pasternack et al., "Cycle–Dependent Variation in the Localization of a Protein Related to Protein 4.1", Nuclear Matrix and Other Proteins, J. Cell Biol., 105: 71a, item No. 392.

(Abstract) Paternack et al., "Characterization of a Protein 4.1 Analog from Murine B Lymphocytes", Membrane–Mediated Cytotoxicity, J. Cell Biochem., Suppl. 10, Part B, 97, item N. G143.

Jaskulski, et al., 1998, "Regulation of the Proliferating Cell Nuclear Antigen Cyclin and Thymidine Kinase.mRNA Levels by Growth Factors," J. Biol. Chem., 263:10175–10179, the American Society for Biochemistry and Molecular Biology, Inc.

Krauss, et al., "Structural Protein 4.1 in the Nucleus of Human Cells: Dynamic Rearrangements during Cell Division," J. Cell. Biol., 137:275–289, 1997, the Rockefeller University Press.

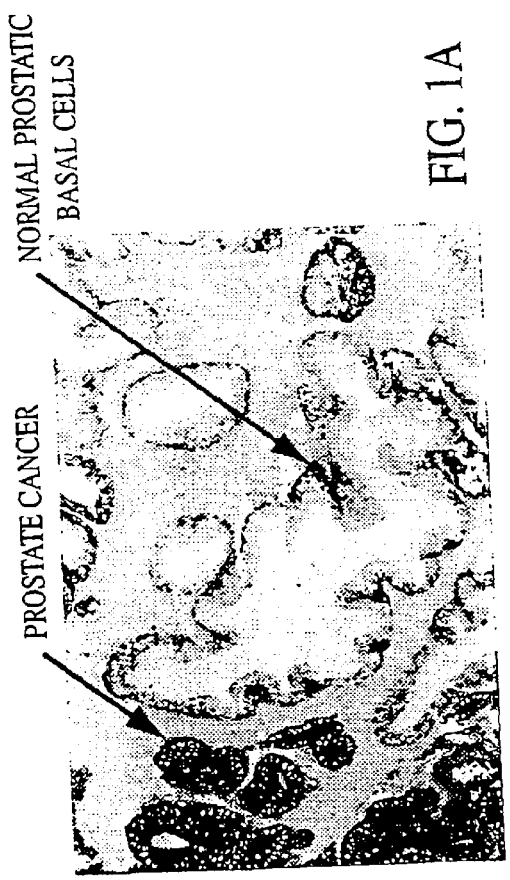
FIG. 1A
FIG. 1B-1
FIG. 1B-2

```
   1    AAGCTTTCCT GATCTCTAAA TCAAGGTCAG CTCCCTAAGC TCTTGGCTCC
  51    CGTACTGAAA CTTTTTCTTA TGTAACTCTC ATAAACACAT AGCATAATGT
 101    TTTGCATGTT TTTCTTCCCT ATCAGTTGCA AGTTCCAGCA GAGCTGATAT
 151    ATTTTCATTT CATTCGCTAC TATAGCCCTA GAGCCTGACA TAGTTTCTGG
 201    CTGTGAATGC TCAATAAATA TTTGTTTAAT TGAGTAGAAA CATAAAGTAT
 251    CTATTTCATT GAAGGAAAGA ATAATTAGCT ACATTTTTCT TTTTCTTGCC
 301    TTAATATTTG AGGAATTTGC TTATATGTCA TAATAAAAAA GTTAAAGCCT
 351    TATACATTAT ACTAAGGAAT TTGGACATTA AATTCAAGCT AGCCTTTCTA
 401    TAAACAAAAT ACTGAATTTC TGTCCCTAAA TTTGTTCCTT CCCTATTCTT
 451    CCCCATTGAG ATGACACCAA ATCCCTCTAG CTGCTCAAAC CAAGTACCCG
 501    TATGTTATTC TTAATTATCT CTTTACCTTG CTTCTCATAT GCAATTTGTT
 551    AACAAGTCAT CTTCAGTCTG TATCCATTAT TCTCCCTTTC CAGACCACCA
 601    ACATGTCTTG ACTATACTGC TACAATAGCC TCCCAACTCT TGTCCTACTT
 651    AAAATTCATT GTAAAAAATC AGTCTTGGCC GGGCACGGTG GCTCACACCT
 701    ATAATCCCAG CACTTTGGGA GTCCCAGGCG GGCGGGTCAC GAGGTCAAGA
 751    GATGGAGACC ATCATGGCCA ACATGGTGAA ACCCTGTCTC TACTATAAAT
 801    ACAAAAAAAT TATCTGGGTG TGGTGGCACA TGCCTGTAAT CCCAACTACT
 851    AGGGAGGCTG AGGCAGGAGA ATCGCTTGAA CCTGGAGGC GGAGGTTGCA
 901    GTGAGCCGAG ATCGCACCAT TGCACTCCAG CCTGGCAACA GAGCGAGACT
 951    CCATCCCAAA ACAAAACAAA ACAAACCAT GTAAAACATG TCTGTAAAAC
1,001    ATGTCAGATT TCGTGTTCAG AAGTCTTACA TGTCTTTTCA TTATGCTAAG
1,051    ATAAAACCCA AATGCATTTT CTTGGTTTCT AAAGCCAAGA AAATAAGAGT
1,101    TGCTTTCAGC AACCTTGTTT CTTCCGCCAT GCTTTTCCCT AGCTCACTCT
1,151    TTTAGGCAA GTCGACCTGA TTTTCTTTCT GTTAGTCTGT TTCTGCCTCG
1,201    TGGTCTGGCT TTCTTTCTGT TAGTCTGTTT CCACCTCGTG GTCTTGGTCC
1,251    TGGCTCTTCA TTCTGCCTGG AATGCTCTCC ACTCCAGATC CTTACTAGAT
1,301    CTTAGCTCAG TCATCACCCT CGCAGGAAGA TCTTCCAACC ATTCACCTGC
1,351    ATACACCTAT GGCTGCTCCC TAGAGAACAT CATTCTGTTT TCTTCACTTC
1,401    CTAGCACTTA CTGCTTTCTG AAATTATCTA CTTTGATTGT TTATTTCTTT
1,451    CTTTACTCTT ACTAGGATAC CTGGGTCATT AAAGGAGGGA TATTTCTCTC
1,501    TTATTTACTG TTATAAACTT AATGCTTAGG CTGTAGAAGT TATACAATAT
1,551    TTGAAGAATA AATCGTTAAA TGTATAACAT TTTTGAAGAA AGATAATTGT
```

```
1,601  GGGATCCATT TAGTTTGCAA ACATTTGATC TGTGTGTTAG ACAGAAGGCC
1,651  ATGGTAAAGG ACAAAGACAT ATTTTATAGG ACTGTACCCT GAAAAATAAA
1,701  TAAACTTGAA CCAGTTATAC AAGACTTATG TGCAGGAAAC AGGTACCAGT
1,751  TATATTTAGA AATGGTAAAT CACCTTCTAA GCATAACTCA GAGCACAATA
1,801  TATTAGAGGG TAGAGAGAGA AGTGCGTCTT AGATATTGGT AATCATATTA
1,851  GGACTGACGC CATCCTTGAT TTTTCTTCTG GGAAACAGCT CAAAATGACT
1,901  ATTTAATGTT TACAATGATA TCTTGCATCT TGCCAGTAAA TAATATAATA
1,951  GACACTAGGA ATCCAAATTG TAAGATGAAC AAGTCTTTAT AGAGGGAGAG
2,001  CCAAATACAC AATAAATAAC ACAAGGTGGT AAATGCAGTA ATACAAACAT
2,051  ACATACCATG CATAGGAGTG CAGAGAAGGT GTGCTTCTCC GAATGCAGTC
2,101  ACCCAGAAAG TCCTTCTGTA GAAAGGGATA TCTTAAATGG TGCTTAAAGG
2,151  AAAAGTAACC AAAGGCAACT AAAGATTGCA AGGAGGTCCC AGGAAAAAGC
2,201  AAAGAACCA AAGGTACATA GGCACAAAAG TAGCCTGCCT TCCTGGGAAC
2,251  TTCCAATAGT TTGCTGGAGC ACACAGTTAG AAGTACTGTG CCATGGGAGC
2,301  AAAGACTGAA GACATATGCA GGTTCAAGGG CACAGAGCCC CATATATGTC
2,351  ATGATAAGAT ATTGGGAAGC CACTGGGGAG CTACTGAAAC TTTAAGCAGG
2,401  GAAATAAAAT TGTCATATCT ACACCTTAGA AATTTGATTT TTTTCTCTTC
2,451  TTTTATCTTC TCTTCTCCTC TCTTCTCTCT CTCTCTCTCT CTCTCTCTCT
2,501  GTGTGTGTGT GTGTGTGTGT GTGTGTGTGT GACAGAGTCC TGCTCTGTCA
2,551  CCCAGGCTGG AGTGTAGTGG AGTGATCTCC GCTTACTGCA GTCTCTGCCT
2,601  CTCAAGCGAT TCCCTGCCTC AGCCTCCCGA GTAGCTGGGA TTACAGGCGG
2,651  GCTCTACAAC AGCTGGCTAA CTTTTGTATT TTTTGGTAAC AACCAGGTTT
2,701  TACCATGTTG GCCAGGCTGG TCTTGAACTC CTGACCTCAG GTGATCTGCC
2,751  TGCCTTGGCT TTCCAAAGTG CTGGGATTAC AGGCGTGAGC CACCCTGCCT
2,801  GGTGTAGAAG TTTGATTTTG ATGTCAGTGT GGTAGATGAA TTTGTGGGAA
2,851  GCAAAACAAG ATAGAGTTCA ATGACAGTGA AAAGTTTATT GTATAAGCTA
2,901  TATAAAAGAA AATGTTGAAG GTTTGAAATC CATTAGTGGC AGTAAGGGTG
2,951  TACAGAACGA AACTATTTGA GAAGTACACA AGGCAAGTCT TACTTTCAAG
3,001  GCAGTTTATC TAAGCTCATT CAATTGTCTC AGTGTTCTTG CTATGTGTGG
3,051  GTTATAGGAT TTGAACATA TGATCAATCT GAGCACACAT CAGTAAACTG
3,101  AATAGGATTA TTAAAATCCA CAAGCATTTT ACTAGTGGAA TCTGTGATAT
3,151  TTTCTAGCTA CTCTTGCTTG TTTTATTTGA ATCTTTTGCT CATATCCTAT
3,201  AGTAAAGATT TCAGGAAATA TATTTTTATT TGCCTAGAAT TTTAGCCTTT
```

FIG. 2 - Continued

```
3,251  TAGTTTTTTG AATCTATTGC TCATATTCTT ATAGTAAGAG TTTCAGGGAA
3,301  TGTATTTCTA TTTGTCTGGA ATTTTAGCCT TTCAGGTTTT TGAGCCCCTC
3,351  TTTTGCTTAT GGGACATAGT ATGAGACAAG ATGAAATGAT ACTTCTATTC
3,401  CCAATTCACT GATGGGGAAA ATGAAGCAAA AAATGTTATT CACTCAAGGC
3,451  TTCTGCCATG TTTCCTGGTG GAATTACGGC TCAGACACAA ATTTCCTAAT
3,501  GCCTGTGCTG CTAACTTCTC AATAGAACAC TATATTAATT TATCTTCTTC
3,551  CTGAGTGTTT TTCCACAAAT CCCATAGCCT GTGAAAGAT TGTTTTAGGG
3,601  AAATATTATT TTTAATATAG CATATTTGT CAATGTGGGA CATAGGACTA
3,651  GTACCTGCTG AAAACCATCT CATGATCCTT GTGTAAGAAC TAATTCACAC
3,701  TAGAAATACT ATTTTCCTTG CTCATTAAAA ACATAAATGT CTCAGAAAGT
3,751  AAAAAATTAT TCCTCTCTAA ATAAACATAC ATGCCACTCA AATTTTATTC
3,801  CTCTACCACT TGCCGTATCT AAACCTAGTT AGATACTTTG GTTTTAGGTA
3,851  TAATCTGACA GAACAGATAC AACCAAGATC ACATTGTGAG TCAGAAGTGG
3,901  AAAATTCATA ATTCATGATG ATACCAATAA AAGATAGATT TAGCTTTTTA
3,951  CAGGATGTTT TTGGCATTTT ATTCTTTCAT TTGAGGGGAG ATCTCACCAA
4,001  AATATGTCTT TCATGGTTCA TTGTGTTATT TAATTTCTGT GATGCATATT
4,051  CTCAGGTTAC TTTAAACCTA GTCTATAGAT TCAAAGATAT CCCGTGTCAG
4,101  GTCTCTAAAA GTAAAAGAA AAATGGGTAC TTGTGAAGGC TGATTCACAG
4,151  TAAGTAGTGT AGAGGGGAGT GCCTTGTGTA TTCACAAATT ATCAACGTGA
4,201  GCATCAGATA AGATTTTCTT TAGTCACACA CACCTACCTT CTTACTAGGA
4,251  AGATCCATAT ACTTGAATAA TTGTTCTGCT TGACCCAGGT TACTTATCAG
4,301  TCCCTTTATT ATAATATTTG TAAATATTGG GGCTCGAGAA CCGAGCGGAG
4,351  CTGGTTGAGT CTTCAAAGTC CTAAAACGTG CGGCCGTGGG TTCGAGGTTT
4,401  ATTGATTGAA TTCGGCTGGC ACGAGAGCCT CTGCAGACAG AGAGCGCGAG
4,451  AGATGGAGAT GGGCAGACGG ATTCATTCAG AGCTGCGGAA CAGGGCGCCC
4,501  TCTGATGTGA AAGAACTTGC CCTGGACAAC AGTCGGTCGA ATGAAGGCAA
4,551  ACTCGAAGCC CTCACAGATG AATTTGAAGA ACTGGAATTC TTAAGTAAAA
4,601  TCAACGGAGG CCTCACCTCA ATCTCAGACT TACCAAAGTT AAAGTTGAGA
4,651  AAGCTTGAAC TAAGAGTCTC AGGGGCCTG GAAGTATTGG CAGAAAAGTG
4,701  TCCAAACCTC ACGCATCTAT ATTTAAGTGG CAACAAAATT AAAGACCTCA
4,751  GCACAATAGA GCCACTGAAA CAGTTAGAAA ACCTCAAGAG CTTAGACCTT
4,801  TTCAATTGCG AGGTAACCAA CCTGAACGAC TACGGAGAAA ACGTGTTCAA
4,851  GCTTCTCCTG CAACTCACAT ATCTCGACAG CTGTTACTGG GACCACAAGG
4,901  AGGCCCCTTA CTCAGATATT GAGGACCACG TGGAGGGCCT GGATGACGAG
```

FIG. 2 - Continued

```
4,951  GAGGAGGGTG AGCATGAGGA GGAGTATGAT GAAGATGCTC AGGTAGTGGA
5,001  AGATGAGGAG GGCGAGGAGG AGGAGGAGGA AGGTGAAGAG GAGGACGTGA
5,051  GTGGAGGGGA CGAGGAGGAT GAAGAAGGTT ATAACGATGG AGAGGTAGAT
5,101  GGCGAGGAAG ATGAAGAAGA GCTTGGTGAA GAAGAAGGG GTCAGAAGCG
5,151  AAAATGAGAA CCTGAAGATG AGGGAGAAGA TGATGACTAA GTAGAATAAC
5,201  CTATTTTGAA AAATTCCTAT TGTGATTTGA CTGTTTTTAC CCATATCCCC
5,251  TCCCCCCTCC AATCCTGCCC CCTGAAACTT ACTTTTTTCT GATTGTAACA
5,301  TTGCTGTGGG AATGAGACGG GAAAGTGTA CTGGGGGTTG TGGAGGGAGG
5,351  GAGGGCAGGA GGCGGTGGAC TAAAATACTA TTTTTACTGC CAAATAAAAT
5,401  AATATTTGTA AATATTAACT GGGATACTAG CTTTGTAGAA TGATTACTAT
5,451  TAATTATTCT CTCTCTCTTT TTATTTTTTT ACACATTCTA TTCTTTTAAG
5,501  TATAGTCCTT TTAGTCCAAG GAAAGGCAC TACAATCCAC TTATTAATGC
5,551  TTGCTACTGT GTTCAAGTAA AATAAGCTCC AGGATTTAAC AAAAGAGGA
5,601  AAGAAAATAT TTACAATGAA AATGTTGCTA AAATTTAAA ACAAATTACA
5,651  GTAAATGTAT TGTTAAAGCA AATTCTATTT TTAAAATTTA TTAATAAGGA
5,701  AATAATTTGC TAAAGCAAAT TTTGGAAAA ATAATAATGC ACTTTATACT
5,751  TGATTTTATT TATTAAAACA ATGATTTATA AGCTT (SEQ ID NO: 1)
```

```
4,357 GAGTCTTCAA AGTCCTAAAA CGTGCGGCCG TGGGTTCGAG GTTTATTGAT TGAATTCGGC
    1 gaattcccaa agtcctaaaa cgcgcggccg tgggttcggg gtttattgat tgaattccgc 4,417 TGGCACGAGA GCCTCTGCAG ACAGAGAGCG CGAGAGATGG AGATGGGCAG ACGGATTCAT
   61 cggcgcggga gcctctgcag agagagagcg cgagagatgg agatgggcag acggattcat 4,477 TCAGAGCTGC GGAACAGGGC GCCCTCTGAT GTGAAAGAAC TTGCCCTGGA CAACAGTCGG
  121 ttagagctgc ggaacaggac gccctctgat gtgaaagaac ttgtcctgga caacagtcgg 4,537 TCGAATGAAG GCAAACTCGA AGCCCTCACA GATGAATTTG AAGAACTGGA ATTCTTAAGT
  181 tcgaatgaag gcaaactcga aggcctcaca gatgaatttg aagaactgga attcttaagt 4,597 AAAATCAACG GAGGCCTCAC CTCAATCTCA GACTTACCAA AGTTAAAGTT GAGA---AAG
  241 acaatcaacg taggcctcac ctcaatcgca aacttaccaa agttaaacaa acttaagaag 4,654 CTTGAACTAA ---------G AGTCTCAGGG GGCCTGGAAG TATTGGCAGA AAAGTGTCCA
  301 cttgaactaa gcgataacag agtctcaggg ggcctagaag tattggcaga aaagtgtccg 4,705 AACCTCACGC ATCTATATTT AAGTGGCAAC AAAATTAAAG ACCTCAGCAC AATAGAGCCA
  361 aacctcacgc atctaaattt aagtggcaac aaaattaaag acctcagcac aatagagcca 4,765 CTGAAACAGT TAGAAAACCT CAAGAGCTTA GACCTTTTCA ATTGCGAGGT AACCAACCTG
  421 ctgaaaaagt tagaaaacct caagagctta gacctttta attgcgaggt aaccaacctg 4,825 AACGACTACG GAGAAAACGT GTTCAAGCTT CTCCTGCAAC TCACATATCT CGACAGCTGT
  481 aacgactacg gagaaaatgt gttcaagctc ctcccgcaac tcacatatct cgacggctat 4,885 TACTGGGACC ACAAGGAGGC CCCTTACTCA GATATTGAGG ACCACGTGGA GGGCCTGGAT
  541 gaccgggacg acaaggaggc ccctgactcg gatgctgagg gctacgtgga gggcctggat 4,945 GACGAGGAGG AGGGTGAGCA TGAGGAGGAG TATGATGAAG ATGCTCAGGT AGTGGAAGAT
  601 gatgaggagg aggatgagga tgaggaggag tatgatgaag atgctcaggt agtggaagac 5,005 GAGGAGGGCG AGGAGGAGGA GGAGGAAGGT GAAGAGGAGG ACGTGAGTGG AGGGGACGAG
  661 gaggaggacg aggatgagga ggaggaaggt gaagaggagg acgtgagtgg agaggaggag
```

```
5,065 GAGGATGAAG AAGGTTATAA CGATGGAGAG GTAGATGGCG AGGAAGATGA AGAAGAGCTT
  721 gaggatgaag aaggttataa cgatggagag gtagatgacg aggaagatga agaagagctt 5,125 GGTGAAGAAG AAAGGGGTCA GAAGCGAAAA TGAGAACCTG AAGATGAGGG AGAAGATGAT
  781 ggtgaagaag aaagggggtca gaagcgaaaa cgagaacctg aagatgaggg agaagatgat 5,185 GACTAAGTAG AATAACCTAT TTTGAAAAAT TCCTATTGTG ATTTGACTGT TTTTACCCAT
  841 gactaagtgg aataacctat tttgaaaaat tcctattgtg atttgactgt ttttacccat 5,245 ATCCCCTCCC CCCTCC---- --AATCCTGC CCCCTGAAAC TTACTTTTTT CTGATTGTAA
  901 atccccctctc cccccccct ctaatcctgc ccctgaaac ttatttttt ctgattgtaa 5,299 CATTGCTGTG GGAATGAGAC GGGAAAAGTG TACTGGGGGT TGTGGAGGGA GGGAGGGCAG
  961 cgttgctgtg ggaacgagag gggaagagtg tactgggggt tgcgggggga ggatggcggg 5,359 GAGGCGGTGG ACTAAAATAC TATTTTTACT GCC (SEQ ID NO: 2)
1,021 tggg-ggtgg aataaaatac tatttttact gcc (SEQ ID NO: 3)
```

```
1    MEMGRRIHSE LRNRAPSDVK ELALDNSRSN EGKLEALTDE
1    MEMGRRIHLE LRNRTPSDVK ELVLDNSRSN EGKLEGLTDE

41   FEELEFLSKI NGGLTSISDL PKL-KLRKLE L---RVSGGL
41   FEELEFLSTI NVGLTSIANL PKLNKLKKLE LSDNRVSGGL

77   EVLAEKCPNL THLYLSGNKI KDLSTIEPLK QLENLKSLDL
81   EVLAEKCPNL THLNLSGNKI KDLSTIEPLK KLENLKSLDL

117  FNCEVTNLND YGENVFKLLL QLTYLDSCYW DHKEAPYSDI
121  FNCEVTNLND YRENVFKLLP QLTYLDGYDR DDKEAPDSDA

157  EDHVEGLDDE EEGEHEEEYD EDAQVVEDEE GEEEEEEGEE
161  EGYVEGLDDE EEDEDEEEYD EDAQVVEDEE DEDEEEEGEE

197  EDVSGGDEED EEGYNDGEVD GEEDEEELGE EERGQKRK*-
201  EDVSGEEEED EEGYNDGEVD DEEDEEELGE EERGQKRKRE
               ---------- (SEQ ID NO: 4)
241  PEDEGEDDD* (SEQ ID NO: 5)
```

FIG. 4

...
GGGTTCGAGGTTTATTGATTGAATTCGGCTGGCACGAGAGCCTCTGCAGACA
GACAGCGCGAGAGATGGAGATGGGCAGACGGATTCATTCAGAGCTGCGGAA
CAGGGCGCCCTCTGATGTGAAAGAACTTGCCCTGGACAACAGTCGGTCGAA
TGAAGGCAAACTCGAAGCCCTCACAGATGAATTTGAAGAACTGGAATTCTT
AAGTAAAATCAACGGAGGCCTCACCTCAATCTCAGACTTACCAAAGTTAAA
GTTGAGAAAGCTTCAACTAAGAGTCTCAGGGGGCCTGGAAGTATTGGCAGA
AAAGTGTCCAAACCTCACGCATCTATATTTAAGTGGCAACAAAATTAAAGA
CCTCAGCACAATAGAGCCACTGAAACAGTTAGAAAACCTCAAGAGCTTAGA
CCTTTTCAATTGCCAGGTAACCAACCTGAACGACTACGGAGAAACGTGTTC
AAGCTTCTCCTGCAACTCACATATCTCGACAGCTGTTACTGGGACCACAAGG
AGGCCCCTTACTCAGATATTGAGGACCACGTGGAGGGCCTGGATGACGAGG
AGGAGGGTGAGCATGAGGAGGAGTATGATGAAGATGCTCAGGTAGTGGAAG
ATGAGGAGGGCGAGGAGGACGAGGAGGAAGGTGAAGAGGAGGACGTGAGT
GGAGGGCACGAGGAGGATGAAGAAGGTTATAACGATGGAGAGGTAGATGG
CGAGGAAGATGAAGAAGAGCTTGGTGAACAAGAAAGGGGTCAGAAGCGAA
AATGAGAACCTGAAGATGAGGGAGAAGATGATGACTAAGTAGAATAACCTA
TTTTGAAAAATTCCTATTGTGATTTGACTGTTTTTACCCATATCCCCTCCCCC
CTCCAATCCTGCCCCCTGAA (SEQ ID NO:6)

```
                  1                                                            50
                                         c
   hpp32
AF008216          a                      g            a  a
    TSU6                                 g            a  a
    TSU3                                 g            t  a                    ..
    TSU1                   g             c
      P8                                              t  a
      P3                   g             c
      L3                                 g            a  a
   FT3-3                                              t  a                    ..
  FT3-18          g                                   t  a                    ..
   FT2-4          g                      g            a  a                     .
   FT2-2                                 c
   FT1-7                                 c
   FT1-3                   g             .            t  a                    ..
  FT1-11                                 c
      D5                                 c
      D3                                 c
      D1
Consensus  GGGTTCGGGG TTTATTGATT GAATTCCGCT GGCGCGGGAG CCTCTGCAGA 51                                                           100
   hpp32                   .                                    c
AF008216    c              .                                    c
    TSU6    c              .    c
    TSU3           a    t  .                     a  t
    TSU1                   .
      P8    a    c   ... t                       a  t  .
      P3                   .                                    c
      L3    c              .
   FT3-3           a       t    .                a  t
  FT3-18           a       t    .                a  t
   FT2-4    c              .                                    c
   FT2-2           g       .
   FT1-7                   .                     a  t
   FT1-3           a    t  .                                    c
  FT1-11                   .
      D5                   .
      D3                   .
      D1                        g
Consensus  GAGAGAGCGC -GAGAGATGG AGATGGGCAG ACGGATTCAT TTAGAGCTGC
```

FIG. 7A - Continued

```
              101                                                    150
   hpp32                                     c
AF008216            g
    TSU6      g
    TSU3            g                        c
    TSU1                  c              t              a
      P8
      P3                  c              t              a
      L3                                     c
   FT3-3            g                                   
 FT3-18                   c              t              a
  FT2-4                   c              t              a
  FT2-2            g
  FT1-7
  FT1-3
 FT1-11                   c              t              a
      D5                                            t
      D3
      D1
Consensus  GGAACAGGAC GCCCTCTGAT GTGAAAGAAC TTGTCCTGGA CAACAGTCGG 151                                                    200
   hpp32                            c
AF008216
    TSU6                            c
    TSU3
    TSU1      a            t g
      P8
      P3      a            t g
      L3                                 c
   FT3-3                                                g
  FT3-18     a            t g
   FT2-4     a            t g
   FT2-2                                 c
   FT1-7
   FT1-3                         g
  FT1-11     a            t g
      D5
      D3
      D1
Consensus  TCGAATGAAG GCAAACTCGA AGGCCTCACA GATGAATTTG AAGAACTGGA
```

FIG. 7A - Continued

```
              201                                              250
hpp32
AF008216                 a           g                    t   g
TSU6
TSU3                     a           g                    t   g
TSU1          a    a                 a                    t       g
P8                                                                g
P3            a    a                 a                    t       g
L3
FT3-3                    a           g                    t   g
FT3-18        a    a                 a                    t       g
FT2-4         a    a                 a                    t       g
FT2-2                    a           g                    t   g
FT1-7
FT1-3
FT1-11        a    a                 a                    t       g
D5
D3
D1
Consensus   ATTCTTAAGT ACAATCAACG TAGGCCTCAC CTCAATCGCA AACTTACCAA 251                                              300
                                                   ga
hpp32
AF008216         ... gt g ga        . ........               c   t
TSU6                                 . ...
TSU3             ... gt g ga                                 c   t
TSU1                                                         c   t
P8                                                           c   t
P3                                                 ga
L3
FT3-3            ... gt g ga        . ........               c   t
FT3-18                                                       c   t
FT2-4                                          . ........ a
FT2-2            ... gt g ga        . ........
FT1-7            ... gt g ga                   ga
FT1-3                                                        c   t
FT1-11                                             ga
D5                                                 ga
D3                                                 ga
D1
Consensus   AGTTAAACAA ACTTAAGAAG CTTGAACTAA GCAGTAACAG AGTCTCAGGG
```

FIG. 7A - Continued

```
                301                                                    350
                                    g
     hpp32                                                              t
    AF008216     g                              ta
      TSU6                                                              t
      TSU3      g                               ta
      TSU1                                      ta
        P8                                      ta
        P3
        L3     g                g                                       t
      FT3-3    g                                ta
     FT3-18                                     ta
      FT2-4                                                             t
      FT2-2    g                                                    c   t
      FT1-7    g
      FT1-3    g                g
     FT1-11                                     ta
        D5                      g
        D3                                      ta
        D1             g                g
   Consensus  GGCCTAGAAG TATTGGCAGA AAAGTGTCCA AACCTCACGC ATCTAAATTT 351                                                    400
     hpp32                                                              c
    AF008216                                              c
      TSU6                                                              c
      TSU3                                                c
      TSU1
        P8                                                c
        P3
        L3                                                              c
      FT3-3                                               c
     FT3-18                                               c
      FT2-4                                                             c
      FT2-2                                                             c
      FT1-7
      FT1-3                                               c
     FT1-11
        D5                                                c
        D3
        D1
   Consensus  AAGTGGCAAC AAAATTAAAG ACCTCAGCAC AATAGAGCCA CTGAAAAAGT
```

FIG. 7A - Continued

|       | 401 |   |   |   | 450 |
|-------|-----|-----|-----|-----|-----|
| hpp32 |     |     |     |     |     |
| AF008216 |  |     |     | c   |     |
| TSU6  | g   |     |     |     |     |
| TSU3  |     |     |     | c   |     |
| TSU1  | g   |     |     |     |     |
| P8    |     |     | c   |     |     |
| P3    | g   |     |     | c   |     |
| L3    |     |     |     |     |     |
| FT3-3 |     |     |     | c   |     |
| FT3-18| tg  |     |     | c   |     |
| FT2-4 | g   |     |     |     |     |
| FT2-2 |     |     |     |     |     |
| FT1-7 |     |     |     |     |     |
| FT1-3 |     |     |     |     |     |
| FT1-11| g   |     |     | c   |     |
| D5    |     |     |     |     |     |
| D3    | g   |     |     | c   |     |
| D1    |     |     |     |     |     |
| Consensus | TAGAAAACCT | CAAGAGCTTA | GACCTTTTCA | ATTGCGAGGT | AACCAACCTG |

|       | 451 |   |   |   | 500 |
|-------|-----|-----|-----|-----|-----|
| hpp32 |     |     |     |     | c   |
| AF008216 |  | g   | c   | t   |     |
| TSU6  | a   | t   | g ga |    | t - |
| TSU3  |     | g   | c   | t   |     |
| TSU1  | a   | t   | ga  |     |     |
| P8    |     |     |     |     | c   |
| P3    | a   |     |     |     | c   |
| L3    |     |     |     |     | c   |
| FT3-3 |     | g   | c   | t   |     |
| FT3-18| a   | t   | ga  |     |     |
| FT2-4 | a   | t   | ga  |     |     |
| FT2-2 |     | g   | c   | t   |     |
| FT1-7 |     | g   | c   | t   |     |
| FT1-3 |     |     |     |     | c   |
| FT1-11| a   | t   | ga  |     |     |
| D5    |     |     |     |     | c   |
| D3    | a   | t   | ga  |     |     |
| D1    |     |     |     |     | c   |
| Consensus | AACGACTACC | GAGAAAATGT | GTTCAAGCTC | CTCCTGCAAC | TCACATATCT |

FIG. 7A - Continued

```
              501                                                                550
hpp32                    a
AF008216          a    t   c                              t      a    at
TSU6        a              c  t                           a           g
TSU3              a    t   c                              t      a    at
TSU1        a              c  t                           a           g
P8                    a
P3                    a
L3                    a
FT3-3             a    t   c                              t      a    at
FT3-18            a        c  t                           a           g
FT2-4       a              c  t                           a           g
FT2-2             a    t   c                              t      a    at
FT1-7             a    t   c                              t      a    at
FT1-3                 a
FT1-11      a              c  t                           a           g
D5                    a
D3          a              c  t                           a           g
D1                    a
Consensus   CGACGGCTGT GACCGGGACG ACAAGGAGGC CCCTGACTCG GATGCTGAGG 551                                                                600
                                       t
hpp32
AF008216    a c                                           g      c
TSU6            tt     t              a
TSU3        c c                                           g      c
TSU1            tt     t              a
P8                                              t
P3                                              t
L3                                              t
FT3-3       a c                                           g      c
FT3-18                          c  t
FT2-4           tt     t              a
FT2-2       a c                                           g      c
FT1-7       a c                                           g      c
FT1-3                                           t
FT1-11          tt     t              a
D5                                              t
D3              tt     t              a
D1                                              t
Consensus   GCTACGTGGA GGGCCTGGAT GACGAGGAGG AGGATGAGGA TGAGGAGGAG
```

FIG. 7A - Continued

```
              601                                              650
   hpp32                           c
 AF008216                                        c            g
    TSU6                 a
    TSU3                                         c            g
    TSU1                 a
      P8                     a       c
      P3                             c
      L3                             c
    FT3-3                                        g            g
   FT3-18                             c
    FT2-4                a
    FT2-2                                        g            g
    FT1-7                                        g            g g
    FT1-3                             c
   FT1-11                a
      D5                             c
      D3                a
      D1                             c
Consensus  TATGATGAAG ATGCTCAGGT AGTGGAAGAT GAGGAGGACG AGGATGAGGA 651                                              700
   hpp32                                         g   c
 AF008216                                            c        a g t
    TSU6         c                                   c        a g t
    TSU3                                         g   c
    TSU1         c                                   c        a g t
      P8
      P3
      L3
    FT3-3                                        g   c g
   FT3-18                                            c        a g t
    FT2-4         c                                  c
    FT2-2                                        g   c
    FT1-7                                        g   c
    FT1-3                                            c        a g t
   FT1-11         c
      D5                                             c        a g t
      D3         c
      D1
Consensus  GGAGGAAGGT GAAGAGGAGG ACGTGAGTGG AGAGGAGGAG GAGGATGAAG
```

FIG. 7A - Continued

```
                701                                              750
      hpp32                          g
   AF008216                a         t
       TSU6                          g
       TSU3                          t
       TSU1      a
         P8
         P3
         L3
       FT3-3                         g
      FT3-18
       FT2-4      a                  t
       FT2-2                         g
       FT1-7
       FT1-3
      FT1-11      a                  t
         D5
         D3      a                   t
         D1
  Consensus  AAGGTTATAA CGATGGAGAG GTAGATGACG AGGAAGATGA AGAAGAGCTT
                751                                              800
      hpp32                                          c
   AF008216                                          t
       TSU6                                         ta         a
       TSU3                                          t
       TSU1                                         ta         a
         P8                                          c
         P3                                          c
         L3                                          c
       FT3-3                                         t
      FT3-18                                         c
       FT2-4                                        ta         a
       FT2-2                                         t
       FT1-7                                         c
       FT1-3                                         c
      FT1-11                                        ta         a
         D5                                          c
         D3                                         ta         a
         D1                                          c
  Consensus  GGTGAAGAAG AAAGGGGTCA GAAGCGAAAA -GAGAACCTG AAGATGAGGG
```

FIG. 7A - Continued

```
801                                                          850
  hpp32
  AF008216                         a              t                      t
     TSU6        c       c                        t                      t
     TSU3                          a
     TSU1        c       c                        t                      t
       P8
       P3
       L3
     FT3-3                         a
    FT3-18                                        t                      t
     FT2-4       c       c
     FT2-2                         a
     FT1-7
     FT1-3                                        t                      t
    FT1-11       c       c
       D5                                         t
       D3        c       c
       D1
Consensus  AGAAGATGAT GACTAAGTGG AATAACCTAT TTTGAAAAAT TCCTATTGTG 851                                                900
  hpp32                                                             c
  AF008216                                              ... ...
     TSU6       t                g   g   c     ... ..  .    a
     TSU3                                      ... ...
     TSU1       t                g   g         ... ..       a
       P8
       P3
       L3                                          .
     FT3-3                                     a ... ...
    FT3-18                       g   g         ... ..       a
     FT2-4       t               g   g         ... ..       a
     FT2-2                                   c... ...
     FT1-7
     FT1-3
    FT1-11       t               g   g         ... ..       a
       D5
       D3
       D1
Consensus  ATTTGACTGT TTTTACCCAT ATCCCCTCTC CCCCCCCCCT CTAATCCTGC
```

FIG. 7A - Continued

```
              901
hpp32                        (SEQ ID NO: 8)
AF008216                     (SEQ ID NO: 9)
TSU6                         (SEQ ID NO: 10)
TSU3                         (SEQ ID NO: 11)
TSU1                         (SEQ ID NO: 12)
P8                           (SEQ ID NO: 13)
P3                           (SEQ ID NO: 14)
L3                           (SEQ ID NO: 15)
FT3-3                        (SEQ ID NO: 16)
FT3-18                       (SEQ ID NO: 17)
FT2-4                        (SEQ ID NO: 18)
FT2-2                        (SEQ ID NO: 19)
FT1-7                        (SEQ ID NO: 20)
FT1-3                        (SEQ ID NO: 21)
FT1-11                       (SEQ ID NO: 22)
D5                           (SEQ ID NO: 23)
D3                           (SEQ ID NO: 24)
D1                           (SEQ ID NO: 25)
Consensus  CCCCTGAA          (SEQ ID NO: 7)
```

```
                    1                                                                    50
       hpp32                      g                                                          
       TSU-6                                       f        q                            l n
       TSU-1       kw                                                                        
       PC3-8                                       f        q                            l n
       PC3-3       kw                              i        q                  a            k
       FT3-3              s        a               a                 a                    l n
       FT3-18      kw                              f        q                  a            k
       FT2-2              s        a                                                         
       FT1-7                                                v                                
       DU-145-5                                                                              
       DU-145-3
    Consensus   MEMGRRIHLE LRNRTPSDVK ELVLDNSRSN EGKLEGLTDE FEELEFLSTI 51                            d                       t              100
       hpp32                                   a v                                           
       TSU-6                                   a v                                           
       TSU-1       i                           a v                                           
       PC3-8                                   a v                                           
       PC3-3       i                                                          t    y         
       FT3-3       g       sd        . r       ...                                           
       FT3-18      i                           a v                            t    y         
       FT2-2       g       sd        . r       ...k                           t    y         
       FT1-7                         . r       ...                            t              
       DU-145-5                                 d                                            
       DU-145-3                                 d
    Consensus   NVGLPSIANL PKLNKLKKLE LSSNRVSGGL EVLAEKCPNL IHLNLSGNKI 101                                                                    150
       hpp32                   e        t           n    ---------- ----------
       TSU-6                   e        t           n    ---------- ----------
       TSU-1                            s                                                    
       PC3-8                   e        t           n                                        
       PC3-3                                                   g         l      scyw
       FT3-3            q               e        t    n    ---------- ----------
       FT3-18                                                  g         l      scyw
       FT2-2            q                                      g         l      scyw
       FT1-7            q                                                                    
       DU-145-5                         e        t    n    ---------- ----------
       DU-145-3
    Consensus   KDLSTIEPLK KLENLKSLDL FNCEVTNLND YRENVFKLLP QLTYLDGYDR
```

```
                151                                                        200
    hpp32    ---------- ---------- ---------- ---------- ----------
    TSU-6    ---------- ---------- ---------- ---------- ----------
    TSU-1    ---------- ---------- ---------- ---------- ----------
    PC3-8
    PC3-3
    FT3-3    h     y  i    dh         g  h              g  e
    FT3-18   ---------- ---------- ---------- ---------- ----------
    FT2-2    h     y  i    dh         g  h              g  e
    FT1-7    h     y  i    dh         g  h              g  eg
    DU-145-5 ---------- ---------- ---------- ---------- ----------
    DU-145-3 ---------- ---------- ---------- ---------- ----------
   Consensus DDKEAPDSDA EGYVEGLDDE EEDEDEEEYD EDAQVVEDEE DEDEEEEGEE 201                                               249
    hpp32    ---------- ---------- ---------- ---------- ---------
    TSU-6    ---------- ---------- ---------- ---------- ---------
    TSU-1    ---------- ---------- ---------- ---------- ---------
    PC3-8
    PC3-3
    FT3-3          gdg              g                   -- ---------
    FT3-18   ---------- ---------- ---------- ---------- ---------
    FT2-2          gd               g                   -- ---------
    FT1-7          gd
    DU-145-5 ---------- ---------- ---------- ---------- ---------
    DU-145-3 ---------- ---------- ---------- ---------- ---------
   Consensus EDVSGEEEED EEGYNDGEVD DEEDEEELGE EERGQKRKRE PEDEGEDDD 1                                                          50
    hpp32
    TSU-6                    g                f     q                  l  n
    TSU-1           kw
    PC3-8           kw                        f     q                  l  n
    PC3-3                s       a            a          a                k
    FT3-3                                     a     q                  l  n
    FT3-18          kw
    FT2-2                s       a                        a               k
    FT1-7
    DU-145-5                                        v
    DU-145-3
   Consensus MEMGRRIHLE LRNRTPSDVK ELVLDNSRSN EGKLEGLTDE FEELEFLSTI
```

FIG. 7B - Continued

```
              51                                                              100
hpp32                        d                          t
TSU-6                                   a v
TSU-1          i                        a v
PC3-8                                   a v
PC3-3          i                        a v
FT3-3          g    sd    . r    ...                    t   y
FT3-18         i                        a v
FT2-2          g    sd    . r    ...k                   t   y
FT1-7                     . r    ...                    t   y
DU-145-5                     d                          t
DU-145-3                     d
Consensus  NVGLTSIANL PKLNKLKKLE LSSNRVSGGL EVLAEKCPNL IHLNLSGNKI 101                                                             150
hpp32                     e       t          n      ---------- ----------
TSU-6                     e       t          n      ---------- ----------
TSU-1                     e       t          n      ---------- ----------
PC3-8                             s                 ---------- ----------
PC3-3                     e       t          n      ---------- ----------
FT3-3          q                                    g    l        scyw
FT3-18                    e       t          n      ---------- ----------
FT2-2          q                                    g    l        scyw
FT1-7          q                                    g    l        scyw
DU-145-5                                            ---------- ----------
DU-145-3                  e       t          n
Consensus  KDLSTIEPLK KLENLKSLDL FNCEVTNLND YRENVFKLLP QLTYLDGYDR 151                                                             200
hpp32      ---------- ---------- ---------- ---------- ----------
TSU-6      ---------- ---------- ---------- ---------- ----------
TSU-1      ---------- ---------- ---------- ---------- ----------
PC3-8
PC3-3
FT3-3        h    y  i  dh         g h                   g e
FT3-18     ---------- ---------- ---------- ---------- ----------
FT2-2        h    y  i  dh         g h                   g e
FT1-7        h    y  i  dh         g h                   g  eg
DU-145-5   ---------- ---------- ---------- ---------- ----------
DU-145-3   ---------- ---------- ---------- ---------- ----------
Consensus  DDKEAPDSDA EGYVEGLDDE EEDEDEEEYD EDAQVVEDEE DEDEEEEGEE
```

FIG. 7B - Continued

```
             201                                                      249
    hpp32    ----------  ----------  ----------  ----------  ---------  (SEQ ID NO:27)
    TSU-6    ----------  ----------  ----------  ----------  ---------  (SEQ ID NO:28)
    TSU-1    ----------  ----------  ----------  ----------  ---------  (SEQ ID NO:29)
    PC3-8                                                               (SEQ ID NO:30)
    PC3-3                                                               (SEQ ID NO:31)
    FT3-3       gdg          g                               -- ------  (SEQ ID NO:32)
    FT3-18   ----------  ----------  ----------  ----------  ---------  (SEQ ID NO:33)
    FT2-2       gd           g                               -- ------  (SEQ ID NO:34)
    FT1-7       gd                                                      (SEQ ID NO:35)
  DU-145-5                                                              (SEQ ID NO:36)
  DU-145-3   ----------  ----------  ----------  ----------  ---------  (SEQ ID NO:37)
  Consensus  EDVSGEEEED  EEGYNDGEVD  DEEDEEELGE  EERGQKRKRE  PEDEGEDDD  (SEQ ID NO:26)
```

GENE FAMILY WITH TRANSFORMATION MODULATING ACTIVITY

This application is a continuation of PCT/US 98/26433 filed Dec. 11, 1998 which claims benefit of 60/069,677 filed Dec. 12, 1997

The work leading to this invention was supported in part by Grant No. RO1 CA 54404 from the National Institutes of Health. The U.S. Government retains certain rights in this invention.

BACKGROUND

1. File of the Invention

This invention is directed to various members of a gene family with transformation modulating activity, and to diagnostic and gene therapy techniques based an the variants.

2. Review of Related Art

Prostatic adenocarcinoma is the most frequent malignancy in adult men with approximately 317,000 new cases diagnosed each year (Parker, et al., CA, 46:8–27, 1996). In spite of the capabilities for early diagnosis and treatment (Potosky, et al., JAMA, 273:548–552, 1995), it represents the second leading cause of cancer death in men following lung cancer.

To date, the study of alterations in specific genes has not been particularly rewarding in primary prostate cancer. Most alterations in the widely studied oncogenes and tumor suppressor genes occur in only 20–30% of primary prostate carcinomas, except for the myc gene, where overexpression has been observed in as many as 50–60% of such cases (Fleming, et al., Cancer Res., 46:1535–1538, 1986). Up to 40% of primary prostate cancers studied by comparative genomic hybridization display chromosomal aberrations (Visakorpi, et al., Cancer Res., 55:342–347, 1995), although such alterations occur more frequently as tumors recur and become refractory to hormonal therapy. Characterization of candidate proto-oncogenes or tumor suppressor genes at such altered loci may eventually shed light on tumor progression in the prostate.

pp32 (GenBank HSU73477) is a highly conserved nuclear phosphoprotein. Increased expression of pp32 or closely related species is a frequent feature of clinical cancers. For example, in human prostate cancer, high-level expression of RNA hybridizing with pp32 probes occurs in nearly 90% of clinically significant prostate cancers, in contrast to the substantially lower frequencies of alterations of other oncogenes and tumor suppressors (See U.S. Pat. No. 5,726,018, incorporated herein by reference).

Molecular Features and Activities of pp32.

pp32 is a nuclear phosphoprotein that is differentiation-regulated during differentiation of adult prostatic epithelium (Walensky, et al., Cancer Res. 53:4720–4726, 1993). The human pp32 cDNA sequence (Gen-Bank U73477) is 1052 bp in length and encodes a protein of 249 amino acids. The protein is composed of two domains: an amino terminal amphipathic α-helical region containing a leucine zipper, and a highly acidic carboxyl terminal region. The murine and human forms of pp32 are highly conserved with over 90% nucleic acid homology and over 95% protein-level homology.

Human pp32 has been isolated independently by a number of groups. Vaesen et al. ("Purification and characterization of two putative HLA class II associated proteins: PHAPI and PHAPII." *Biol. Chem. Hoppe-Seyler.*, 375:113–126. 1994) cloned an essentially equivalent molecule, termed PHAPI, from an EBV-transformed human B-lymphoblastoid cell line; PHAPII, cloned by the same strategy, is unrelated to pp32. This study identified PHAPI through its association in solution with human HLA class II protein, noting membrane and cytoplasmic localization as well as nuclear; the gene has putatively been localized to chromosome 15q22.3-q23 by fluorescent in situ hybridization (Fink, et al., "Localization of the gene encoding the putative human HLA class II-associated protein (PHAPI) to chromosome 15q22.3-q23 by fluorescence in situ hybridization." *Genomics*, 29:309–310,1995). More recently, a group studying inhibitors of protein phosphatases identified pp32 as IIPP2a an inhibitor of protein phosphatase 2a (Li, et al., "Molecular Identification of II PP2A, a novel potent heat-stable inhibitor protein of protein phosphatase 2A." *Biochemistry* 35:6998–7002, 1996); another phosphatase inhibitor, I2PP2a, is unrelated to pp32. Interestingly, another recent report (Ulitzur, et al., "Biochemical characterization of mapmodulin, a protein that binds microtubule-associated proteins." *Journal of Biological Chemistry* 272:30577–30582, 1997) identified pp32 as a cytoskeletally-associated cytosolic protein in CHO cells. It is not clear whether this finding stems from a difference in system, or whether pp32 can localize to the cytoplasm under certain circumstances, pp32 has also been identified as LANP, a leucine rich nuclear protein in the central nervous system (Matsuoka, et al., "A nuclear factor containing the leucinc-rich repeats expressed in murine cerebellar neurons. *Proc Nail Acad Sci USA* 91:9670–9674, 1994).

There are also a number of reports of gene products bearing lesser degrees of homology to pp32. The Vacsen group has identified a series of unpublished sequences, termed PHAP12a (EMBL Locus HSPHAP12A) and PHAP12b (EMBL Locus HSPHAP12B), also cloned from an EBV-transformed human B-lymphoblastoid cell line. These variant pp32 sequences are distinct from the sequences reported herein, representing the April protein instead. April, cloned from human pancreas, is shorter than PHAP12a by two N-terminal amino acids (Mencinger, et al., "Expression analysis and chromosomal mapping of a novel human gene, APRIL, encoding an acidic protein rich in leucines." *Biochimica et Biophysica Acta.* 1395:176–180, 1998, see EMBL Locus HSAPRIL), PHAP12b is identical to a subset of APRIL. Silver-stainable protein SSP29 (unpublished GenBank Locus HSU70439) was cloned from HeLa cells and is identical to PHAP12a.

The nuclear phosphoprotein pp32 has been linked to proliferation. Malek and associates reported that various neoplastic cell lines showed markedly elevated expression levels and that bacterial polysaccharide induced expression of pp32 epitopes by B lymphocytes upon polyclonal expansion (Malek, et al., J. Biol. Chem., 265:13400–13409, 1990). Walensky and associates reported that levels of pp32 expression, measured by in situ hybridization, increased in direct relation to increasing Gleason grade of human prostatic cancers.

pp32 cDNA probes hybridize strongly with prostatic adenocarcinoma, whereas the hybridization signal in normal prostate is confined to basal cells. Polyclonal,anti-pp32 antibodies react strongly with sections of human prostatic adenocarcinoma. The antibodies and riboprobes used by the investigators in previous studies are consistent with cross-reactivities of the reagents with all reported members of the pp32 nuclear phosphoprotein family, therefore, while previous descriptions focused upon pp32, it cannot be excluded that homologous proteins were detected.

SUMMARY OF THE INVENTION

In one aspect, this invention provides a DNA molecule containing at least a portion of the sequence consisting of base pairs 4894–4942 of the sequence shown in FIG. 2 or its complement. Alternatively, the DNA molecule may contain at least a portion consisting of base pairs 4879–4927, or base pairs 4858–4927. Alternatively, this invention provides a DNA molecule that contains at least a portion of a nucleotide sequence encoding amino acid residues 146–163 of tumor-derived pp32r1 sequence; preferably the DNA encodes all of that segment. In one mode, the DNA molecule is an expression vector which expresses said amino acid sequence, and the invention also includes a recombinant cell containing the expression vector. In another mode, the DNA molecule has the particular sequence operatively linked to a promoter in antisense orientation. In another alternative, this invention provides a DNA probe which specifically hybridizes on Northern blot with nucleic acid encoding the amino acids from residue 146–163 of the tumor-derived pp32r1 sequence, a preferred probe would have a sequence of at least 8 contiguous nucleotides "unique" to the nucleotide sequence of the pp32r1 variant as described herein. In yet another alternative, the invention provides a pair of nucleic acid primers each of which comprises at least 10 contiguous nucleotides, at least one of the primers binding specifically to the pp32r1 sequence, where if the primers arc used in nuclcic acid amplification of a suitable source of human nucleic acid, the amplification will produce an amplified nucleic acid encoding at least residues 146–163 of the pp32r1 sequence.

In still another aspect, this invention provides antibodies that specifically bind the tumor derived pp32, but do not bind to normal pp32. Preferably, these antibodies are monoclonal antibodies. The invention also provides polypeptides containing epitopes that bind these antibodies.

In yet another aspect this invention provides diagnostic methods for predicting malignant potential of neuroendocrine, neural, mesenchymal, lymphoid, epithelial or germ cell derived tumors by determining, in a sample of human neuroendocrine, neural, mesenchymal, lymphoid, epithelial or germ cell derived tissue, the level of, or the intracellular sites of expression of, a gene product expressed from a gene sequence which encodes, inter alia, residues 146–163 of tumor derived pp32r1. Where the gene product is mRNA, the mRNA is extracted from the sample and quantitated, optionally by PCR, or the level of mRNA may be determined by in situ hybridization to a section of the tissue sample. Where the gene product is protein, the determination may include reacting the sample with an antibody that specifically binds to tumor derived pp32, but not to normal pp32. Preferably, the tissue sample is carcinoma tissue, e.g., carcinoma or sarcoma of a tissue selected from the group consisting of epithelial, lymphoid, hematopoietic, mesenchymal, central nervous system and peripheral nervous system tissues, including colon carcinoma, prostate carcinoma and non-Hodgkin's lymphoma.

In still another aspect, this invention provides an androgen-activated transcriptional promoter which may be inserted into recombinant DNA molecules. The minimal promoter is made up of a transcription initiation site and at least one binding site for a steroid hormone receptor protein. Typically the consensus sequence for the steroid hormone receptor protein binding site is positioned within 5000 nucicotide base pairs (bp), more preferably within 3000 bp, or even fewer bp of the transcription initiation site: In a preferred mode, a number of binding sites for steroid hormone receptor proteins are positioned within that distance of the transcription initiation site, the promoter may contain five, ten or even 5 steroid hormone receptor protein binding sites. Preferably, the binding site(s) for steroid hormone receptor protein binding are selected from the consensus sequences listed on Table 1. In a preferred mode of the invention, the androgen-activated transcriptional promoter is operatively linked to an open reading frame comprising at least one exon of a protein coding sequence, operative linking of the open reading frame thereby providing an expression vector in which expression of the open reading frame is regulated by steroids.

In another aspect, this invention provides a method for screening candidate compounds for pharmacological activity by (1) culturing a cell transfected with the DNA molecule containing the androgen-activated transcriptional promoter which is operatively linked to an open reading frame comprising at least one exon of a protein coding sequence. and (2) determining expression of the open reading frame in the presence and absence of the compound. In a preferred mode the androgen-activated promoter may be all or an operative portion of the sequence in FIG. 2 which is up-stream of the translation initiation site, or alternatively the androgen-activated promoter may be the 2700 bp of the sequence in FIG. 2 which is upstream from the translation initiation site. pp32) is a member of a highly conserved family of differentiation-regulated nuclear proteins that is highly expressed in nearly all human prostatic adenocarcinomas of Gleason Grade $\geq$ 5. This contrasts with the low percentage of prostate tumors that express molecular alterations in proto-oncogenes or demonstrate tumor suppressor mutation or loss of heterozygosity. By analysis of specimens of human prostatic adenocarcinoma and paired adjacent normal prostate from three individual patients, the inventors have shown that normal prostate continues to express normal pp32, whereas three of three sets of RT-PCR-amplified transcripts from prostatic adenocarcinomas display multiple cancer-associated coding sequence chances. The cancer-associated sequence changes appear to be functionally significant. Normal pp32 exerts antineoplastic effects through suppression of transformation. In contrast, cancer-associated pp32 variants augment, rather than inhibit, transformation.

BRIEF DESCRIPTION OF THE DRAWINGS

FIG. 1A shows detection of pp32-related mRNA in benign prostate and prostate cancer tissue sections by in silts hybridization.

FIG. 1B shows immunohistochemical stain of prostate cancer sections with anti-pp32 antibodies.

FIG. 2 shows the genomic sequence of variant pp32r1 isolated from human placenta.

FIG. 3 provides a base-by-base comparison of the sequence of pp32r1 (top) with normal human pp32 (bottom). The numbering system for pp32r1 corresponds to FIG. 1, and the numbering system for normal pp32 is taken from Chen, et al. Nucleotide base differences are underlined in the pp32r1 sequence. Sequences within the normal pp32 sequence missing in pp32r1 are represented by dashes. The open reading frame for pp32r1 is indicated by overlining.

FIG. 4 shows the alignment of the pp32r1 amino acid sequence (top) with normal human pp32 (bottom). Residue changes are underlined in the pp32r1 sequence. Amino acids missing in the pp32r1 sequence compared to normal pp32 arc represented by dashes.

FIG. 5 shows the genomic sequence of variant pp32r2.

FIG. 7 shows the alignment of nucleic acid (A) and amino acid (B) sequences from human prostatic adenocarcinoma and prostatic adenocarcinoma cell lines with pp32.

DETAILED DESCRIPTION OF THE INVENTION

Figure 6A:
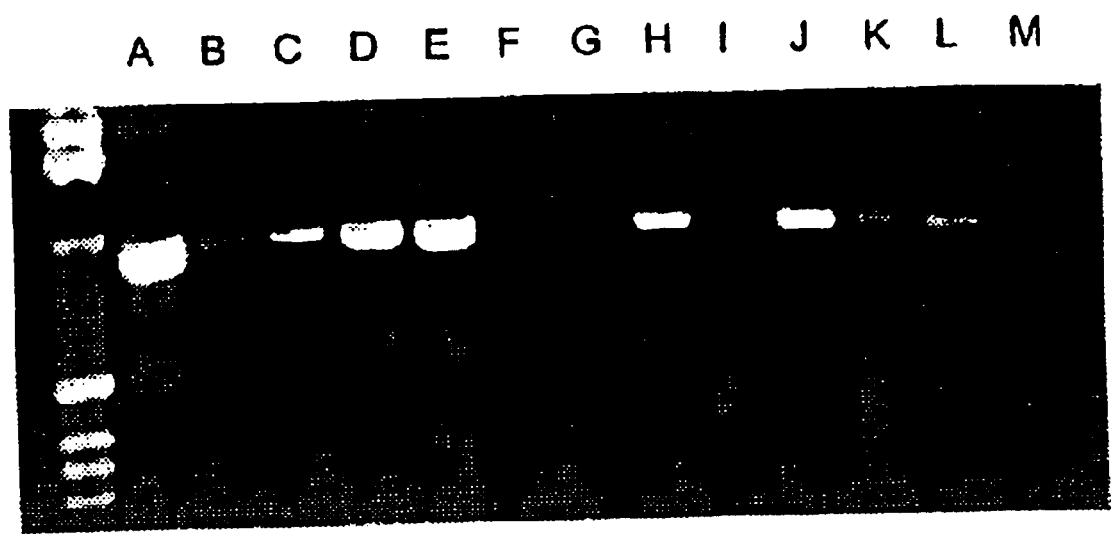
FIG. 6A shows RT-PCR amplification of pp32 and pp32 variants from human prostate cancer and prostate cancer cell line.

The inventors have discovered that phenotypic changes in pp32 are a common feature of human prostate cancer. Previous data show that 87% of prostate cancers of Gleason Score 5 and above express pp32 or closely-related transcripts (U.S. Pat. No. 5,734.022, incorporated herein by reference). This is striking in comparison to the frequency of molecular alterations in other widely studied oncogenes and tumor suppressor genes in primary prostatic adenocarcinoma, which occur-in a substantially smaller proportion of cases. For example, myc overexpression (Fleming, et al.) Occurs in around 60% of cases, and p53 is abnormal in only around 25% of primary tumors (Isaacs, et al., in "Genetic Alterations in Prostate Cancer." *Cold Spring Harbor Symposia on Quantitative Biology*, 59:653–659, 1994).

Several lines of evidence suggest that pp32 may act as a tumor suppressor. Functionally, pp32 inhibits transformation in vitro by oncogene pairs such as ras with myc, mutant p53, E1a, or jun, or human papilloma virus E6 and E7 (Chen, et al., "Structure of pp32, an acidic nuclear protein which inhibits oncogene-induced formation of transformed foci." *Molecular Biology of the Cell*. 7:2045–2056, 1996), pp32 also inhibits growth of transformed cells in soft agar (Chen, et al.). In another system, ras-transfected NIH3T3 cells previously transfected to overexpress normal human pp32 do not form foci in vitro or, preliminarily, do not form tumors in nude mice, unlike control cells. In contrast, knockout of endogenous pp32 in the same system by an antisense pp32 expression construct markedly augments tumorigenesis (Example 12 below).

In clinical prostate cancer, the situation at first appears counterintuitive. Most human prostate cancers seem to express high levels of pp32 by in situ hybridization (see Example 1 below) and stain intensely with anti-pp32 antibodies. Because pp32 inhibits oncogene-mediated transformation (Chen, et al.), its paradoxical expression in cancer was investigated at the sequence level. The paradoxical question of why prostate cancers seem to express high-levels of an anti-oncogenic protein was addressed by comparing the sequence and function of pp32 species from paired normal prostate and adjacent prostatic carcinoma from three patients as well as from four prostate cancer cell lines. It is demonstrated herein that pp32 is a member of a closely-related gene family, and that alternate expression of these closely-related genes located on different chromosomes modulates oncogenic potential in human prostate cancer. The variant pp32 species expressed in prostate cancer are closely related to pp32.

The present data indicate that prostate cancers express variant pp32 transcripts. whereas adjacent normal prostate expresses normal pp32. Two instances clearly show that expression of alternate genes on different chromosomes can lead to the phenotypic switch, rather than mutation or alternate splicing. This switch in molecular phenotype is accompanied by a switch in functional pp32 phenotype. Normal pp32 is anti-oncogenic in character, in contrast to the pro-oncogenic variant transcripts that foster oncogene-mediated transformation. The high frequency of this abnormality suggests that expression of variant pp32 species may play an etiologic role in the development of human prostate cancer. In addition, these findings have significant diagnostic and prognostic implications.

Definitions

In describing the present invention, the following terminology is used in accordance with the definitions set out below.

Nucleic Acids

In discussing the structure of particular double-stranded DNA molecules, sequences may be described herein according to the normal convention of giving only the sequence in the 5' to 3' direction along the nontranscribed stand of DNA (i.e., the strand having a sequence homologous to the mRNA).

A DNA sequence "corresponds" to an amino acid sequence if translation of the DNA sequence in accordance with the genetic code yields the amino acid sequence (i.e., the DNA sequence "encodes" the amino acid sequence), one DNA sequence "corresponds" to another DNA sequence if the two sequences encode the same amino acid sequence.

Two DNA sequences are "substantially similar" when at least about 90% (preferably at least about 94%, and most preferably at least about 96%) of the nucleotides match over the defined length of the DNA sequences. Sequences that arc substantially similar can be identified by the assay procedures described below or by isolating and sequencing the DNA molecules. See e.g., Maniatis et al., infra, DNA Cloning, vols. I and II infra: Nucleic Acid Hybridization, infra.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A "coding sequence" or "open reading frame" is an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptides in vivo. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. Promoter sequences typically contain additional sites for binding of regulatory molecules (e.g., transcription factors) which affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

Vectors are used to introduce a foreign substance, such as DNA, RNA or protein, into an organism. Typical vectors include recombinant viruses (for DNA) and liposomes (for protein). A "DNA vector" is a replicon, such as plasmid, phage or cosmid, to which another DNA segment may be attached so as to bring about the replication of the attached segment. An "expression vector" is a DNA vector which contains regulatory sequences which will direct protein synthesis by an appropriate host cell. This usually means a promoter to bind RNA polymerase and initiate transcription of mRNA, as well as ribosome binding sites and initiation signals to direct translation of the mRNA into a polypeptides. Incorporation of a DNA sequence into an expression vector at the proper site and in correct reading frame, followed by transformation of an appropriate host cell by the vector, enables the production of a protein encoded by said DNA sequence.

An expression vector may alternatively contain an antisense sequence, where a small DNA fragment, corresponding to all or part of an mRNA sequence, is inserted in opposite orientation into the vector after a promoter. As a result, the inserted DNA will be transcribed to produce an RNA which is complementary to and capable of binding or hybridizing with the mRNA. Upon binding to the mRNA, translation of the mRNA is prevented, and consequently the protein coded for by the mRNA is not produced. Production and use of antisense expression vectors is described in more detail in U.S. Pat. No. 5,107,065 (describing and exemplifying antisense regulation of genes in plants) and U.S. Pat. No. 5,190,931 (describing antisense regulation of genes in both prokaryotes and eukaryotes and exemplifying prokaryotes), both of which arc incorporated herein by reference.

"Amplification" of nucleic acid sequences is the in vitro production of multiple copies of a particular nucleic acid sequence. The amplified sequence is usually in the form of DNA. A variety of techniques for carrying out such amplification are described in a review article by Van Brunt (1990, Bio/Technol., 8(4):291–294). Polymerase chain reaction or PCR is a prototype of nucleic acid amplification, and use of PCR herein should be considered exemplary of other suitable amplification techniques.

Polypeptides

For the purposes of defining the present invention, two proteins are homologous if 80% of the amino acids in their respective amino acid sequences are the same; for proteins of differing length, the sequences will be at least 80% identical over the sequence which is in common (i.e., the length of the shorter protein).

Two amino acid sequences are "substantially similar" when at least about 87% of the amino acids match over the defined length of the amino acid sequences, preferably a match of at least about 89%, more preferably a match of at least about 95%. Typically, two amino acid sequences which are similar will differ by only conservative substitutions.

"Conservative amino acid substitutions" are the substitution of one amino acid residue in a sequence by another residue of similar properties, such that the secondary and tertiary structure of the resultant peptides are substantially the same. Conservative amino acid substitutions occur when an amino acid has substantially the same charge or hydrophobicity as the amino acid for which it is substituted and the substitution has no significant effect on the local conformation of the protein. Amino acid pairs which may be conservatively substituted for one another are well-known to those of ordinary skill in the art.

The polypeptides of this invention encompass pp32r1 and pp32r1 analogs, pp32r2 and pp32r2 analogs, along with other variants of pp32 and their analogs, pp32r1 and pp32r2 are naturally occurring, mature proteins, and further encompass all precursors and allelic variations of pp32r1 and pp32r2, as well as including forms of heterogeneous molecular weight that may result from inconsistent processing in vivo. An example of the pp32r1 sequence is shown in FIG. 3, top line. "pp32r1 analogs" are a class of peptides which includes:

1) "Allelic variations of pp32r1," which are polypeptides which are substantially similar to pp32r1. Preferably the amino acid sequence of the allelic variation is encoded by a nucleic acid sequence that differs from the sequence of pp32r1 by one nucleotide in 300;
2) "Truncated pp32r1 peptides." which include fragments of either pp32 or allelic variations of pp32r1 that preferably retain either (i) an amino acid sequence unique to pp32r1. (ii) an epitope unique to pp32r1 or (iii) pp32r1 activity;
3) "pp32r1 fusion proteins," which include heterologous polypeptides which are made up of one of the above polypeptides (pp32r1, allelic variations of pp32r1 or truncated pp32r1 peptides) fused to any heterologous amino acid sequence.

"Unique" sequences of the pp32r1 variant according to this invention, either amino acid sequences or nucleic acid sequences which encode them, are sequences Which are identical to a sequence of a pp32r1 polypeptides, but which differ in at least one amino acid or nucleotide residue from the sequences of human pp32 (Genbank Locus HSU73477), murine pp32 (Genbank Locus MMU73478) human cerebellar leucine rich acidic nuclear protein (LANP) (Genbank Locus AF025684), murine LANP (Genbank Locus AF022957). IIPP2a or human potent heat-stable protein phospatase 2a inhibitor (Genbank Locus HSU60823), SSP29 (Genbank Locus HSU70439), HLA-DR associated protein 1 (Genbank Locus HSPPHAP1. Accession No. X75090), PHAP12a (EMBL Locus HSPHAP12A. Genbank Accession No. Y07569), PHAP12b (EMBL Locus HSPHAP12B. Genbank Accession No. Y07570), and April (EMBL Locus HSAPRIL), and preferable, are not found elsewhere in the human genome. (A list of these sequences is provided in Table 3A.) Similarly, an epitope is "unique" to pp32r1 polypeptides if it is found on pp32r1 polypeptides but not found on any members of the set of proteins listed above. Analogs of pp32r2 and unique pp32r2 sequences are defined similarly. Of course, unique sequences of pp32r1 are not found in pp32r2 and vice versa.

"Variants of pp32" are homologous proteins which differ from pp32 by at least 2 amino acids. In particular, sequence comparison between pp3; and a variant will demonstrate at least one segment of 10 amino acids in which the sequence differs by at least two (2) amino acids. More typically a variant will exhibit at least two such 10 amino acid segments. Preferably, variants of pp32 in accordance with this invention will exhibit differences in functional activity from pp32. In particular, pp32r1 and pp32r2 are variants of pp32 whose activity includes stimulation of transformation in the ratefibroblast transformation assay described herein.

A composition comprising a selected component A is "substantially free" of another component B when component A makes up at least about 75% by weight of the combined weight of components A and B. Preferably, selected component A comprises at least about 90% by weight of the combined weight, most preferably at least about 99% by weight of the combined weight. In the case of a composition comprising a selected biologically active protein, which is substantially free of contaminating proteins, it is sometimes preferred that the composition having the activity of the protein of interest contain species with only a single molecular weight (i.e., a "homogeneous" composition).

As used herein, a "biological sample" refers to a sample of tissue or fluid isolated from a individual, including but not limited to, for example, plasma, serum, spinal fluid, lymph fluid, the external sections of the skin, respiratory, intestinal, and genitourinary tracts, tears, saliva, milk, blood cells, tumors, organs, and also samples of in vivo cell culture constituents (including but not limited to conditioned medium resulting from the growth of cells in cell culture medium, putatively virally infected cells, recombinant cells, and cell components).

"Human tissue" is an aggregate of human cells which may constitute a solid mass. This term also encompasses a suspension of human cells, such as blood cells, or a human cell line.

The term "immunoglobulin molecule" encompasses whole antibodies made up of four immunoglobulin peptide chains, two heavy chains and two light chains, as well as immunoglobulin fragments. "Immunoglobulin fragments" are protein molecules related to antibodies, which are known to retain the epitopic binding specificity of the original antibody, such as Fab, F(ab)'$_2$, Fv, etc. Two polypeptides are "immunologically cross-reactive" when both polypeptides react with the same polyclonal antiscrum.

General Methods

The practice of the present invention employs, unless otherwise indicated, conventional molecular biology, microbiology, and recombinant DNA techniques within the skill of the art. Such techniques are well known to the skilled worker and are explained fully in the literature. See, e.g., Maniatis, Fritsch & Sambrook. "Molecular Cloning: A Laboratory Manual" (1982); "DNA Cloning: A Practical Approach." Volumes I and II (D. N. Glover, ed., 1985); "Oligonucleotide Synthesis" (M. J. Gait, ed., 1984), "Nucleic Acid Hybridization" (B. D. Hames & S. J. Higgins, eds., 1985): "Transcription and Translation" (B. D. Hames & S. J. Higgins, eds., 1984): "Animal Cell Culture" (R. I. Freshney, ed., 1986); "Immobilized Cells and Enzymes" (IRL Press. 1986); B. Perbal, "A Practical Guide to Molecular Cloning" (1984), and Sambrook, et al., "Molecular Cloning: a Laboratory Manual" (1989).

pp32 Related Genomic DNA

Screening a human genomic library in bacteriophages with probes generated from human pp32 cDNA yielded a new sequence that contained an open reading frame encoding a protein homologous with pp32 (see Example 2: pp32 sequence, reported in Chen, et al., *Mol. Biol. Cell*, 7:2045–2056, 1996). While the pp32r1 and pp32r2 sequences (see FIGS. 2 and 5) are substantially homologous to pp32, multiple single nucleotide base changes and short deletions suggest that they are encoded by gene distinct from pp32 gene. The pp32 family also includes substantially homologous polypeptides reported by others: HLA-DR associated protein 1 (Vaesen, 1994), leucine-rich acidic nuclear protein (Matsuoka, 1994), and protein phosphatase 2A inhibitor (Li, 1996).

DNA segments or oligonucleotides having specific sequences can be synthesized chemically or isolated by one of several approaches. The basic strategies for identifying, amplifying and isolating desired DNA sequences as well as assembling them into larger DNA molecules containing the desired sequence domains in the desired order, are well known to those of ordinary skill in the art. See, e.g., Sambrook, et al., (1989); B. Perbal. (1984). Preferably, DNA segments corresponding to all or a part of the cDNA or genomic sequence of pp32r1 may be isolated individually using the polymerase chain reaction (M. A. Innis, et al., "PCR Protocols: A Guide To Methods and Applications." Academic Press. 1990). A complete sequence may be assembled from overlapping oligonucleotides prepared by standard methods and assembled into a complete coding sequence. See, e.g., Edge (1981) *Nature* 292:756; Nambair, et al. (1984) *Science* 223:1299: Jay, et al. (1984) *J. Biol. Chem.*, 29:6311.

The assembled sequence can be cloned into any suitable vector or replicon and maintained there in a composition which is substantially free of vectors that do not contain the assembled sequence. This provides a reservoir of the assembled sequence, and segments or the entire sequence can be extracted from the reservoir by excising from DNA in the reservoir material with restriction enzymes or by PCR amplification. Numerous cloning vectors are known to those of skill in the art, and the selection of an appropriate cloning vector is a matter of choice (see, e.g., Sambrook, et al., incorporated herein by reference). The construction of vectors containing desired DNA segments linked by appropriate DNA sequences is accomplished by techniques similar to those used to construct the segments. These vectors may be constructed to contain additional DNA segments, such as bacterial origins of replication to make shuttle vectors (for shuttling between prokaryotic hosts and mammalian hosts), etc.

Procedures for construction and expression of proteins of defined sequence are well known in the art. A DNA sequence encoding pp32r1, pp32r2, or an analog of either pp31R1 or pp32r2, can be synthesized chemically or prepared from the wild-type sequence by one of several approaches, including primer extension, linker insertion and PCR (see. e.g., Sambrook, et al.). Mutants can be prepared by these techniques having additions, deletions and substitutions in the wild-type sequence. It is preferable to test the mutants to confirm that they are the desired sequence by sequence analysis and/or the assays described below. Mutant protein for testing may be prepared by placing the coding sequence for the polypeptides in a vector under the control of a promoter, so that the DNA sequence is transcribed into RNA and translated into protein in a host cell transformed by this (expression) vector. The mutant protein may be produced by growing host cells transfected by an expression vector containing the coding sequence for the mutant under conditions whereby the polypeptides is expressed. The selection of the appropriate growth conditions is within the skill of the art.

The assembled sequence can be cloned into any suitable vector or replicon and maintained there in a composition which is substantially free of vectors that do not contain the assembled sequence. This provides a reservoir of the assembled sequence, and segments or the entire sequence can be extracted from the reservoir by excising from DNA in the reservoir material with restriction enzymes or by PCR amplification. Numerous cloning vectors are known to those of skill in the art, and the selection of an appropriate cloning vector is a matter of choice (see, e.g., Sambrook, et al., incorporated herein by reference). The construction of vectors containing desired DNA segments linked by appropriate DNA sequences is accomplished by techniques similar to those used to construct the segments. These vectors may be constructed to contain additional DNA segments, such as bacterial origins of replication to make shuttle vectors (for shuttling between prokaryotic hosts and mammalian hosts), etc.

Producing the Recombinant Peptide

Preferably, DNA from the selected clones should be subcloned into an expression vector, and the protein expressed by cells transformed with the vector should be tested for immunoreactivity with antibodies against the recombinant protein of this invention prepared as described below. Such subcloning is easily within the skill of the ordinary worker in the art in view of the present disclosure. The amino acid coding region of the DNA sequence of this invention may be longer or shorter than the coding region of the disclosed sequence, so long as the recombinant peptide expressed by the DNA sequence retains at least one epitope cross-reactive with antibodies which are specifically immunoreactive with pp32r1, pp32r2, or other pp32 variant as desired. The preparation of selected clones which contain DNA sequences corresponding to all or part of the sequence of pp32r1 or pp32r2 may be accomplished by those of ordinary skill in the art using conventional molecular biology techniques along with the information provided in this specification.

It is possible to purify a pp32 variant protein, such as pp32r1, which is cross-reactive with antibodies specific for pp3, from an appropriate tissue/fluid source. however, a cross-reactive pp32, variant, or analog thereof, may also be produced by recombinant methods from a DNA sequence encoding such a protein or polypeptides. Polypeptides corresponding to the recombinant protein of this invention may be obtained by transforming cells with an expression vector containing DNA from a clone selected from an mammalian (preferably human) library as described herein. Suitable expression vector and host cell systems are well known to those of ordinary skill in the art, and are taught, for instance, in Sambrook, et al., 1989. The peptide may be obtained by growing the transformed cells in culture under conditions wherein the cloned DNA is expressed. Of course, the peptide expressed by the clone may be longer or shorter than pp32r1 or pp32r2, so long as the peptides are immunologically cross-reactive. Depending on the expression vector chosen, the peptide may be expressed as a fusion protein or a mature protein which is secreted or retained intracellularly, or as an inclusion protein. The desired polypeptides can be recovered from the culture by well-known procedures, such as centrifugation, filtration, extraction, and the like, with or without cell rupture, depending on how the peptide was expressed. The crude aqueous solution or suspension may be enriched for the desired peptide by protein purification techniques well known to those skilled in the an. Preparation of the polypeptides may include biosynthesis of a protein including extraneous sequence which may be removed by post-culture processing.

Using the nucleotide sequences disclosed herein and the polypeptides expressed from them, antibodies can be obtained which have high binding affinity for pp32r1 or pp32r2, but much lower affinity for pp32 and/or other variants of pp32, Such antibodies. whether monoclonal or purified polygonal antibodies can be used to specifically detect pp32r1 or pp32r2. Techniques for preparing polypeptides, antibodies and nucleic acid probes for use in diagnostic assays, as well as diagnostic procedures suitable for detection of pp32 are described in U.S. Pat. Nos. 5,726,018 and 5,734,022, incorporated herein by reference, and these techniques may be applied to pp32r1 or pp32r2 by substitution of the nucleic acid sequences disclosed herein. Similar substitution may be applied to other variants of pp32.

pp32r1 Promoter Sequence

Multiple consensus sequences for binding active steroid receptors found in genomic sequences upstream from the pp32r1 coding region are consistent with hormone regulation of gene expression. The consensus sequences were associated with the both induction and repression of expression by steroid hormones. The combination of both positively and negatively acting elements suggests complex regulation of pp32r1 expression.

Possible steroid hormone regulation of pp32r1 expression is important in regard to prostate cancer. While about one-half of treated patients initially respond to androgen ablation, subsequent hormone refraction and continued aggressive tumor growth is common (Garnick, M. B., Prostate Cancer." in *Scientific American Medicine*, Dale. D. C. and Federman. D. D. Eds., Scientific American Inc., New York. 1995). Many different steroid hormones regulate the growth of prostate cancer cells (Huggins, et al., "Studies on prostate cancer: 1. The effect of castration, of estrogen, and of androgen injection on serum phosphatases in metastatic carcinoma of the prostate," *Cancer Res.*, 1:293, 1941). These findings established a basis for androgen ablation therapy for the treatment of metastatic prostate cancer.

The present invention provides androgen-activated promoters based on the upstream portion of the genomic sequence in FIG. 2. The promoter sequence provided by this invention is bounded at its 3' terminus by the translation start codon of a coding sequence and extends upstream (5' direction) to include at least the number of bases or elements necessary to initiate transcription at levels above background. Within the promoter sequence will be found a transcription initiation site (conveniently defined by mapping with nuclease S1), a protein binding domain (consensus sequence) within about 100 bases upstream of the transcription initiation site generally designated the TATA box (a binding site for TATA box binding proteins and RNA polymerase), and various other protein binding domains (consensus sequences) upstream of the TATA box that modulate the basic transcriptional activity of the transcription initiation site and the TATA box. The various other protein binding domains preferably contain recognition sequences shown in Table 1 for binding (1) androgen receptors, estrogen receptors, glucocorticoid receptors, and progesterone receptors: (2) transcription factors containing the leucine zipper motif including, but not limited to Fos, Jun, JunB, and Myc: and, (3) certain tissue specific transcription factors including, but not limited to GATA-1 and GATA-2. The various other protein binding domains upstream of the TATA box may contribute to specificity (tissue specific expression), accuracy (proper initiation), and strength (transcription frequency) of the promoter. The promoter elements may serve overlapping functions so that the promoter may function in the absence of subsets of these elements.

Therapy

Inhibition of function of protransforming variants of pp32 by any means would be expected to be an avenue of therapy.

U.S. Pat. No. 5,726,018, incorporated herein by reference, describes various therapeutic avenues which may be applied by the skilled worker based on the nucleotides and protein sequences disclosed herein. In a particular embodiment, all or a portion of the sequence of pp32r1 or pp32r2 may be supplied in the antisense orientation to block expression of the variants found in carcinomas, particularly prostate cancer. Suitable methods for preparation of antisense expression vectors and administration of antisense therapy may be found in U.S. Pat. No. 5,756,676, incorporated herein by reference. Prescreening of the patient population using the diagnostic methods described herein to identify patients having tumors expressing the particular pp32 variant is preferred.

Screening for compounds having therapeutic effects in prostate cancer may also be facilitated by the present invention. Studies which may be used to screen candidate compounds are described in U.S. Pat. No. 5,756,676, incorporated herein by reference, modified by the use of cell lines which express particular variants of pp32 (see, e.g., Examples below). Compounds which affect steroid dependent protein expression may also be detected according to this invention by similar screening studies using an androgen-activated promoter as provided herein operatively coupled to a DNA sequence whose expression may be detected. (Marker sequences are well known in the art see, e.g., Sambrook, et al., and selection of an appropriate detectable expression marker is a routine matter for the skilled worker.) Screening by testing the effect of candidate compounds on recombinant cells containing an expression vector having an androgen-activated promoter operatively coupled to an expression marker, with appropriate controls, is within the skill of the art, in view of the promoter sequences provided herein. In one aspect this invention provides a method for screening candidate compounds for pharmacological activity by (1) culturing a cell transfected with the DNA molecule containing an androgen-activated transcriptional promoter which is operatively linked to an open reading frame comprising at least one exon of a protein coding sequence, and (2) determining expression of the open reading frame in the presence and absence of the compound. In a preferred mode the androgen activated promoter may be the portion of the sequence in FIG. 2 which is up-stream of the translation initiation site, or alternatively the androgen activated promoter may be the 2700 bp upstream from the translation initiation site.

Diagnostic Methods Based on the pp32 Gene Family

In one aspect, this invention provides methods for detecting and distinguishing among members of the pp32 gene family. As explained herein, the presence of one or more members of the gene family may be detected using assays based on common structures among the members resulting from common or similar sequences. For example, polyclonal antibodies elicited by pp32 will cross-react with pp32r1 and pp32r2, including various alleles of these pp32 variants. Similarly, the full coding region of the pp32 cDNA will hybridize under suitable conditions with nucleic acid encoding any of the variants, as shown by the in situ detection of the variants in tumor sections which were subsequently shown to contain either pp32r1 or pp32r2 allelic forms (Example 1). Selection of conditions that promote the immune cross-reactivity or cross-hybridization necessary for such detection is within the skill of the art, in view of the examples provided herein. For example, by using large nucleotide probes in hybridization experiments, the effects of one or a few differences in sequence may be overcome, i.e., larger probes will bind to more dissimilar target sequences, in contrast to shorter probes for which each nucleotide makes a larger percentage contribution to the affinity, and a single nucleotide alteration will cause a greater relative reduction in hybridization efficiency. Typically probes of 50 or more nucleotides are used to find homologues to a given sequence, and the studies reported in Example 1 used the entire sequence of pp32 as a probe to find cells expressing homologous members of the gene family other than pp32. Likewise, polyclonal antisera elicited to an antigen having multiple epitopes is more likely to cross-react with a second antigen that has a few of the same epitopes along with many different epitopes, while a monoclonal antibody or even a purified polyclonal antiscrum might not bind to the second antigen.

In addition to determining the presence of one or more members of the pp32 gene family, this invention also provides methods for distinguishing among members. Determining which pp32 variant may be useful, for instance, to determine whether a transformation promoting or suppressing variant is present in a tissue sample. Suitable methods for distinguishing include both immunoassay and nucleic acid binding assays. Preferred are methods which can detect a 10-fold difference in the affinity of the detecting ligand (e.g., antibody or oligonucleotide) for the target analyte. Such methods are well documented for other systems, and may be adopted to distnguish between pp32 variants by routine modification of such methods in view of the guidance provided herein.

Protein level assays may rely on monoclonal or purified polyclonal antibodies of relatively greater affinity for one variant compared to another (see, e.g., Smith, et al. ("Kinetics in interactions between antibodies and haptens." Biochemistry, 14(7):1496–1502. 1975, which shows that the major kinetic variable governing. antibody-hapten interactions is the rate of dissociation of the complex, and that the strength of antibody-hapten association is determined principally by the activation energy for dissociation), and Pontarotti, et al.("Monoclonai antibodies to antitumor Vinca alkaloids: thermodynamics and kinetics," Molecular Immunology, 22(3):277–84, 1985, which describes a set of monoclonal antibodies that bind various dimeric alkaloids and can distinguish among the alkaloid haptens due to different relative affinities of the various monoclonal antibodies for particular dimeric alkaloids), each of which is incorporated herein by reference). Suitable modifications of the conditions for immunoassays to emphasize the relative affinity of monoclonal antibodies with different affinity are also discussed in U.S. Pat. No. 5.759,791, incorporated herein by reference.

A number of methods are available which are capable of distinguishing between nucleic acid sequences which differ in sequence by as little as one nucicotide. For example, the ligase chain reaction has been used to detect point mutations in various genes (see, e.g., Abravaya, et al., "Detection of point mutations with a modified ligase chain reaction (Gap-LCR)." *Nucleic Acids Research*, 23(4):675–82, 1995, or Pfeffer, et al., "A lipase chain reaction targeting two adjacent nucleotides allows the differentiation of cowpox virus from other Orthopoxvirus species," *Journal of Virological Methods*, 49(3):353–60, 1994, each of which is incorporated herein by reference). Amplification of a sequence by PCR also may be used to distinguish sequences by selection of suitable primers, for example, short primers, preferably 10–15 matching nucleotides, where at least one of the primers has on the 3' end a unique base that matches one variant but not other variants, and using annealing conditions under which the primer having the unique base has at least a ten-fold difference in dissociation rate between the fully matching variants and variants which do not fully match. Similar differentiation may be achieved in other methods dependent on hybridization by using short probes (typically under 50 bp, preferably 25 bp or less more preferably less than 20 bp or even 10–12 bp) by adjusting conditions in hybridization reactions to achieve at least a ten-fold difference in dissociation rate for the probes between the fully matching variants and variants which do not fully match. Cleavase fragment length polymorphism may also be used, and a specific example below provides guidance from which the skilled worker will be able to design similar studies by routine selection of other cleavase enzymes in view of the sequences provided herein.

The diagnostic methods of this invention may be used for prognostic purposes and patient differentiation as described herein. In particular, the methods of this invention allow differentiation between products expressed from the various sequences disclosed in FIG. 7. Preferred methods are those that detect and/or differentiate, between pp32, pp32r1, and/or pp32r2. Situations in which differentiation between pp32 variants will be of benefit will be readily apparent to the skilled clinician, in view of the present disclosure. Selection among the diagnostic methods provided by this invention of a suitable technique to achieve the desired benefit is a routine matter for the skilled clinician.

EXAMPLES

In order to facilitate a more complete understanding of the invention, a number of Examples are provided below. However, the scope of the invention is not limited to specific embodiments disclosed in these Examples, which are for purposes of illustration only.

Example 1

Cellular Location of pp32 Expression pp32 mRNA can be detected by in situ hybridization with a pp32 probe under stringent conditions.
In situ hybridization. Bases 1–298 of the pp32 cDNA sequence (GenBank IISU73477) were subcloned into the Bluescript vector by standard techniques. Digoxigenin labeled anti-sense and sense RNA probes were generated using a commercially available kit (Bochringer Mannheim). Vector DNA linearized with BamHI and XhoI served as template for antisense and sense probe generation respectively. In vitro transcription was performed for 2 hours at 37° in a final volume of 20 $\mu$l which contained 1 $\mu$g of template DNA, 2 U/$\mu$l of either T3 or T7 RNA polymerase. 1 U/$\mu$l ribonuclease inhibitor, 1 mM each of ATP, CTP, GTP, 0.65 mM UTP, 0.35 mM digoxigenin-II-UTP, 40 mM Tris-HCl pH 8.0, 10 mM NaCl, 10 mM DTT, 6 mM $MgCl_2$ and 2 mM spermidine. The reaction was stopped by adding 2 $\mu$l of 0.2M EDTA, pH 8. 0 and the synthesized transcripts were precipitated for 30 min at −70° with 2.2 $\mu$l of 4 M LiCl and 75 $\mu$l of pre-chilled ethanol. RNA was pelleted by centrifugation, washed with 80% ethanol, mildly dried and dissolved in 100 $\mu$l of DEPC treated water. Yields of labeled probe were determined by an enzyme linked irrimunoassay using a commercially available kit (Bochringer Mannheim). Non-radioactive in situ hybridization was performed with anti-sense and sense pp32 RNA probes generated by in vitro transcription (see U.S. Pat. No. 5,726,018, incorporated herein by reference). FIG. 1A shows that normal prostatic basal cells are positive, whereas the clear, differentiated glandular cells are negative. In contrast, prostatic adenocarcinoma, shown at left, is strikingly positive. Note that the signal is cytoplasmic since it is mRNA and not the protein that is detected in this assay.

pp32 displays a distinctive pattern of expression in vivo (Chen, et al., Malek, et al., "Identification and preliminary characterization of two related proliferation-associated nuclear phosphoproteins." *Journal of Biological Chemistry*, 265:13400–13409, 1990; Walensky, et al., "A novel M(r) 32,000 nuclear phosphoprotein is selectively expressed in cells competent for self-renewal." *Cancer Research* 53:4720–4726, 1993). In normal peripheral tissues, expression is restricted to stem-like cell populations such as crypt epithelial cells in the gut and basal epithelium in the skin: in the adult central nervous system, cerebral cortical neurons and Purkinje cells also express pp32. In normal prostate. basal cells express pp32, whereas pp32 mRNA is not detectable by in situ hybridization in differentiated glandular cells (FIG. 1A). In contrast, strong in situ hybridization to pp32 probes is found in nearly all clinically significant human prostatic adenocarcinomas. 87% of human prostatic adenocarcinomas of Gleason Score 5 and above express mRNA that hybridizes strongly with probes to pp32 in Contrast to only 11% of prostate cancers of Gleason Score 4 and below in a study of 55 patients.
Immunohistochemistry. Formalin-fixed, paraffin-embedded tissue was sectioned at 4 $\mu$M, deparaffinized, hydrated, processed for heat-induced antigen retrieval at 95 in 0.01 M citrate buffer, pH 6.0, for 20 min (Cattoretti, et al., "Antigen unmasking on formalin-fixed, paraffin-embedded tissue sections," *Journal of Pathology* 171:83–98. 1993), then incubated overnight at room temperature with a 1120 dilution of anti-pp32 antibody. Following washing, the slide was sequentially developed with biotinylated swine-anti-rabbit IgG at 1/100 (Dako), strepavidin peroxidase (Dako), and diaminobenzidine. FIG. 1B shows a representative high-grade human prostate cancer stained with affinity-purified rabbit polyclonal anti-pp32 antibody (Gusev, et al., "pp32 overexpression induces nuclear pleomorphism in rat prostatic carcinoma cells," *Cell Proliferation* 29:643–653, 1996). The left-hand panel shows a representative field at 250x: the rectangle indicates the area shown in computer generated detail in the right-hand panel. Strongly hybridizing tumors show intense immunopositivity with antibodies to pp32, indicating that they express pp32 or immunologically related proteins (FIGS. 1A and 1B).

Example 2

ESTs corresponding to pp32

Several potential variant pp32 species have been identified in the prostate cancer expressed sequence tag libraries of the NCI's Cancer Genome Anatomy Project. Clone 588488 encodes a protein that is 96% identical to APRIL, although absent retrieval and sequencing of the full clone, it is impossible to tell whether the entire EST clone encodes a pp32 related sequence; neither is it possible to assess the biologic function of this molecule at this time. Nevertheless, it is apparent that the sequenced portion encodes a protein bearing great similarity to pp32. This EST does not appear in the database for normal prostate. As with the variant pp32 species recovered from prostate cancer, generation of this molecule by mutation would require a complex mechanism.

pp32-related genes are present in other organisms. The existence of a pp32 gene family in rodent would be consistent with the existence of a comparably sized family in human. A murine pp32 (GenBank U73478) has 89% amino acid identity to pp32, but less identity to pp32r1 and APRIL. (The murine cerebellar leucinc rich acidic nuclear protein has a single amino acid substitution relative to murine pp32.) We additionally identified a murine FST, GenBank AA066733, with closest identity to APRIL, protein at 85% identity over 148 amino acids of a predicted open reading frame. Several other murine EST's. AA212094 and W82526, are closely related to the pp32 family but are not significantly more related to either pp32, pp32r1, or APRIL. A human homologue of such a gene would be expected to encode a fourth member of this gene family. We identified EST's predicted to encode pp32-related proteins in *C. elegans*, schistosomes, zcbrafish, and *Drosophila* (data not shown). However, these sequences may not represent the complete extent of the pp32 gene family in these organisms, and thus are not informative for the likely size of the mammalian pp32 gene family.

Example 3

The Structure of a Gene Encoding a Relative of the pp32 Family

Screening a human genomic library in bacteriophages with probes generated from human pp32 cDNA yielded a new sequence that contained an open reading frame encoding a protein homologous with pp32.

Screening a Human Genomic Library in Bacteriophages for pp32 cDNA:

A genomic library from human placenta in the Lambda Fix II vector was expressed in *E. coli* strain XL-1 Blue MRA (Stratagene #946206). Screening for bacteriophage clones containing DNA inserts homologous with pp32 cDNA followed routine procedures (Sambrook, et at.). Briefly, nitrocellulose filters that had overlain bacteriophage plaques were hybridized with P-32 labeled probes for pp32 cDNA. The probes were prepared by the random primer method (Stratagene #300385) using pp32 cDNA as a template (Chen, et al., *Molec, Biol, Cell*, 7:2045–2056,1996.). Reactive bacteriophage plaques were plugged and the bacteriophages were eluted, reexpressed, and rescreened with pp32 cDNA probes until pure. Bacteriophage DNA was prepared by the plate lysate method (Sambrook, et al.).

Identifying Restriction Fragments within Bacteriophage DNA Containing Sequences Homologous with pp32 cDNA.

DNA from a bacteriophage clone containing pp32 cDNA sequences was digested with HindIII. Using routine methods, the restriction fragments were separated by agarose gel electrophoresis, transferred in alkaline buffer to positively charged nylon filters, and hybridized with probes that were selective for the 5' and 3' ends of the pp32 cDNA (Sambrook et al.). The 5' and 3' probes were prepared as described above except that the products of polymerase chain reactions (PCR) were used as templates for the labeling reactions (Saiki, et al., *Science*, 239:487491, 1988). One PCR product was a 249 base pair segment of pp32 cDNA containing nucleotides 32 through 279. It was the result of a reaction using a pp32 cDNA template and the primers 5'-TATGCTAGCGGGTTCGGGGTTTATTG-3' (SEQ ID NO: 41) and 5'-GATTCTAGATGGTAAGTTTGCGATTGAGG-3' (SEQ ID NO: 42) (primer set A).

The other product was a 263 base pair segment of pp32 cDNA including nucleotides 677 through 938. It was the result of a reaction using a pp32 cDNA template and the primers 5'-GAATCTAGAAGGAGGAGGAAGGTGAAGAG-3' (SEQ ID NO: 43) and 5'-CTATCTAGATTCAGGGGGCAGGATTAGAG-3' (SEQ ID NO: 44) (primer set B).

The PCR reactions included 35 cycles of one minute denaturations at 95° C., one minute primer annealings at 50° C., and one minute extensions at 72° C. (cycling program A). A 4.7 kb HindIII restriction fragment that hybridized with the 5' probe, but not with the 3' probe and a 0.9 kb HindIII fragment that hybridized with the 3' probe, but not with the 5' probe were subcloned into pBluescript (Gibco) by routine methods (Sambrook, et al.). The nucleotide sequences of both strands of purified plasmid DNA containing the inserts were determined by automated procedures (DNA Analysis Facility, Johns Hopkins University School of Medicine).

Completion of Sequencing by Direct Sequencing of PCR Products. Alignment of the sequences of the 4.7 and 0.9 kb HindIII restriction fragments with pp32 cDNA showed about 90% homologies between the 3' end of the 4.7 kb fragment and the 5' region of pp32 cDNA and the 5' end of the 0.9 kb fragment and the 3' region of the pp32 cDNA. There was an unaligned 199 base pair gap of pp32 cDNA sequence between the ends of the restriction fragments. Primers were designed to specifically anneal to relative pp32 sequences on both sides of the sequence gap. The primer sequences were 5'-GAGGTTMATFGATTGAATTCGGCT-3' (SEQ ID NO: 45) and 5'-CCCCAGTACAC=TITCCCGTCTCA-3' (SEQ ID NO: 46) (primer set Polymerase chain reactions followed cycling program A with primer set C and pure bacteriophage DNA as a template. The 943 base pair products were shown by ethidium bromide staining agarose gels, extracted from excised fragments of low melt agarose (NuSieve) electrophoresis gels, and sequenced by automated procedures as described above.

A sequence of 5,785 bases was obtained from the human placental genomic library bacteriophage clone containing segments homologous with pp32 cDNA (FIG. 2). This sequence was deposited in Genbank under Accession No. U71084, Locus HSU71084. The sequence has an open reading frame extending from nucleotides 4,453 to 5,154. Analysis of the nucleotide sequence upstream of the open reading frame revealed consensus sequences for active steroid hormone receptors at over twenty positions (Table 1).

Sequence analysis of the open reading frame showed 94% sequence homology to pp32 (FIG. 3). Alignment of the open reading frame sequence to pp32 cDNA revealed 33 scattered, solitary base differences and clustered differences of two and seven bases. There were two internal deletions of three and nine bases. The open reading frame encoded a polypeptides containing 234 amino acid residues with 88% protein-level homology to pp32 (FIG. 4). Alignment of the translated sequence to the pp32 amino acid sequence revealed 18 scattered, solitary amino acid residue differences, three differences in clusters of two residues, and one difference in a clusters of four residues. There were two internal deletions of one and three residues and a terminal deletion of eleven residues. The translated sequence contained 69 acidic residues, 26 fewer than pp32.

Example 4

Chromosome Mapping of pp32r1

The pp32r1 gene maps to chromosome 4 as determined by PCR of the NIGMS monochromosomal panel 2 (Drwinga, et al., "NIGMS human/rodent somatic cell hybrid mapping panels 1 and 2," Genomics 16:311314, 1993) followed by sequencing of the PCR product. Interestingly, the full sequence of pp32r1 including 4364 nucleotides of sequence 5' to the start ATG contained over 400 matches in a blastn search of the non-redundant GenBank database. These matches were to two short regions of about 278 and 252 base pairs (nucleotides 674–952 and 2542–2794) that represent repeats in opposite orientations, The repeats are significantly related to elements on many chromosomes.

The human pp32 gene has been mapped to chromosome 15q22.3-q23 by fluorescence in situ hybridization (Fink, et al.). A Unigene entry for pp32 (Hs, 76689; HLA-DR associated protein 1) lists 93 EST sequences corresponding to this gene. 12 of which contain a mapped sequence-tagged site (STS). These STS sites are all reported to map to chromosome 15, as are many of the pp32 EST's analyzed by electronic PCR (http://www.ncbi.nlm.nih.gov). APRIL protein was also mapped to chromosome 13q25 (Mencinger, et al.: GenBank Y07969).

Example 5

Sequence Analysis of pp32r2

A pp32-related sequence (designated pp32r2) has been identified on chromosome 12 by methods analogous to those described in Example 2 for isolation of the unique intronless pp32-related gene pp32r1, found on chromosome 4. It was initially thought that the chromosome 12 sequence, encoding a truncated protein, might represent a pseudogene: however that interpretation has been reassessed in view of the present findings. The sequence has been designated pp32r2, and is recorded in Genbank as locus AF008216: the sequence of pp32r2 is shown in FIG. 5. By BESTFIT analysis (Genetics Computer Group. Inc., Wisconsin Package, version 9.1. Madison, Wis 1997), pp32r2is 99.5% identical to FT1.11, FT2.4 and T1, showing four nucleotide differences over the 875 nucleotide overlap of the sequences; this level of variation is consistent with a polymorphism. Similarly. BESTFIT analysis shows that PP32R1 is 99.6% identical to FT3.3 and 99.4% identical to FT2. 2, displaying four and five nucleotide differences, respectively (see FIG. 7 below).

Example 6

Sequence Comparison of Multiple Clones

Screening of a human placental genomic library in Lambda Fix II vector (Stratagene #946206) with P-32 labeled probes for pp32 cDNA yielded a clone of approximately 23 kb. 4.7 kb and 0.9 kb HindIII restriction fragments of this clone hybridized with probes for pp32 cDNA. The 4.7 kb clone aligned with the 5' portion of he pp32 cDNA sequence, and the 0.9 kb fragment aligned with the 3' end. A small discontinuity of 0.2 kb was sequenced from a bridging PCR product. No introns were identified.

Cultured cells including the whole human embryonic line FSH173WE and the prostatic cancer cell lines PC-3 and 1 NCaP (American Type Culture Collection) were grown under recommended tissue culture conditions. Poly A+RNA was prepared by oligo dT adsorption (MicroFasTrack, Invitrogen) and used as a template for the generation of cDNA through reactions with reverse transcriptase and random hexamers (GeneAmp RNA PCR Kit, Perkin Elmer). The cDNA sequences encoding the open reading frame were amplified by nested PCR using primers specifically selective for the genomic sequence over pp32 sequences. The final 298 base pair products were seen by ethidium bromide staining agarose electrophoretic gels.

Using procedures similar to those described in Example 3, except without the need for nested primers in most cases, transcripts from DU-145 cells and from numerous patients were sequenced for comparison to the transcripts from the above samples. The results are shown in Table 2. A summary of the degree of identity between various transcripts is provided in Table 3.

Example 7

Sequence Variation for Individual Isolates of Different Cell Lines and Tumor Tissue The explanation for the apparent discordant expression pp32 in cancer is that prostate tumors do not generally express pp32, but rather express variant pp32 species that promote transformation, instead of inhibiting it.

RT-PCR and CFLP. Sequences were reverse-transcribed and amplified using bases 32 to 52 of HSU73477 as a forward primer and 919 to 938 of the same sequence as a reverse primer in conjunction with the Titan One-Tube RT-PCR kit (Bochringer). Reverse transcription was carried out at 50° for 45 min followed by incubation at 94° for 2 min: the subsequent PCR utilized 45 cycles of 92° for 45,55° for 45 sec, and 68° for 1 min with a final extension at 68° for 10 min in a PTC 100 thermocycler (MJ Research). Template RNA was isolated from cell lines or frozen tumor samples using RNAzol B (Tel-Test) according to the manufacturer's instructions, then digested with RNAse-free DNAse 1 (Bochringer), pCMV32 was used as a positive control without reverse transcription. The cleavage assay was performed according to the manufacturer's specifications (Life Technologies) with digestion at 55° for 10 min at 0.2 mM $MnCl_2$ and electrophoresed on a 6% denaturing polyacrylamide sequencing gel.

At the level of RTPCR, paired normal prostate and prostatic adenocarcinoma from three patients yielded amplification products (FIG. 6A) ranging from 889 to 909 bp. The reaction employed consensus primers capable of ampliring the full-length coding sequence from pp32 and the two closely-related intronless genomic sequences pp32r1 and pp32r2. The sole difference noted was a diminished amplicon yield from normal tissue as compared to neoplastic. Four human prostatic adenocarcinoma cell lines. DU-145, LNCaP, PC-3, and TSUPR-1, also yielded similar products.

FIG. 6A shows RT-PCR amplified DNA from human prostate and prostate cancer cell lines. Lane a is an undigested control whose band migrated substantially slower than the digestion produces; samples in all other lanes were digested with cleavage as described. The lanes show: 1 kb ladder (Life Technologies), A; pCMV32. B; DU-145. C. LNCaP. D; PC-3. E; TSUPr-1. F; a representative sample, FT-1, without reverse transcription. G; FN-1) H; FT-1. I; FN-2. J; FT-2. K; FN-3. L; FT-3. M; negative control with template omitted. FN indicates frozen benign prostate and the number indicates the patient: FT indicates frozen prostatic adenocarcinoma and the number indicates the patient. Numbers on the left-hand side of the figure indicate the size in kb of a reference 1 kb DNA ladder (Life Technologies).

Figure 6B:
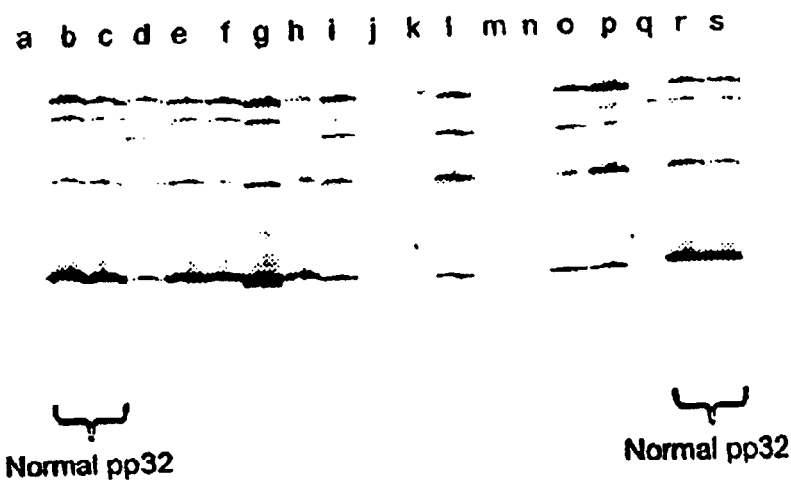
FIG. 6B shows cleavase fragment length polymorphism analysis of pp32 detects variant pp32 transcripts in human prostate cancer.

Qualitative differences between normal and neoplastic tissue began to emerge when the RT-PCR products were subcloned and analyzed by cleavage fragment length polymorphism analysis (CFLP) and sequence analysis. FIG. 6B shows a cleavase fragment length polymorphism analysis of cloned cDNA amplified by RT-PCR from human prostatic adenocarcinoma, adjacent normal prostate, and human prostatic adenocarcinoma cell lines using primers derived from the normal pp32 cDNA sequence. The lanes show individual RT-PCR-derived clones from the DU-145, LNCaP, PC-3 and TSUPr1 cell lines, from frozen prostate cancer (FT) and from frozen normal prostate (FN): a, undigested normal pp32 cDNA; b, normal pp32 cDNA; c, DU-145-1; d, DU-145–3; e, DU-145–5; f, LNCaP-3; g, PC3–3; h, PC3–8; i, TSUPr1, -I;j, TSUPr1–3; k, TSUPr1–6; 1, FT1.11; m, FT1.7; n, FT2.2; o, FT2.4; p, FT3.18; q, FT3.3; r, FN3.17; s, FN2.1, LNCaP expresses normal pp32. The band shifts correspond to sequence differences. All clones of RT-PCR product from normal prostate tissue displayed a normal CFLP pattern that corresponded precisely to that obtained from cloned pp32 cDNA template (GenBank HSU73477. FIG. 6B), Prostatic adenocarcinomas yielded four distinct CFLP patterns upon similar analysis, of which three were unique and one mimicked the normal pp32 pattern. Examination of DU-145. PC-3, and TSUPR-1 cell lines yielded substantially similar results whereas LnCaP yielded only a normal pp32 CFLP pattern. Further analysis at the sequence level confirmed that normal prostate and LnCaP contained solely normal pp32 transcripts.

Transcripts obtained from prostatic adenocarcinomas and from most cell lines represented closely-related variant species of pp32, summarized in Table 1. These transcripts varied from 92.4% to 95.9% nucleotide identity to normal pp32 cDNA (Genetics Computer Group, Inc., Wisconsin Package, version 9.1. Madison, Wis., 1997). Of the sixteen variant transcripts obtained, fifteen had open reading frames encoding proteins ranging from 89.3% to 99.6% identity to normal pp32. The table summarizes data obtained for variant pp32 transcripts obtained from human prostatic adenocarcinoma and prostate cancer cell lines. Sequences falling into closely related groups are indicated by the group letters (A.B.C); U indicates unassigned sequence not clearly falling into a group. The origin of each sequence is: FT, frozen tumor followed by patient number, decimal point, and clone number; D, DU-145 followed by clone number (as are all cell line sequences); P, PC3; and T, TSUPr1. Nucleotide identity, gaps in the nucleotide sequence alignient, and protein identity were determined from BESTFIT alignments with the normal pp32 cDNA and protein sequences. The effect on transformation is described as: stimulates, more foci obtained when transfected with ras+myc than with ras+myc+vector control; inactive, equivalent foci obtained as with ras+myc+vector control, and suppresses, fewer foci obtained as with ras+myc+vector control.

The predicted protein sequences fell into three discrete groups: [1] truncated sequences spanning the N-terminal 131 amino acids of pp32, of which one such sequence substantially equivalent to pp32r2 was obtained identically from two of three patients and from the TSUPR-1 cell line; [2] sequences more closely homologous to a distinct pp32-related gene, pp32r1 than to pp32, and [3] heterogeneous pp32-related sequences. Tumors from two of the three patients analyzed contained no detectable normal pp32 transcripts. Two of twelve cloned transcripts from the third patient tumor were normal by CFLP pattern, with sequence confirmation of normality on one clone. Two clones from cell lines were normal by CFLP screening, but were later shown to represent variant sequences.

FIGS. 7A and 7B show a multiple pairwise alignment of nucleotide and predicted protein sequences for all transcripts (Smith, et al., "Identification of common molecular subsequences." J. Mol. Biol., 147:195–197 1981). The figures were compiled with the GCG Pileup and Pretty programs (Smith, et al.). Differences from the consensus sequences are shown as indicated: agreement with the consensus sequence is shown as a blank. Normal human pp32 is designated hpp32. Sequences from the TSUPr1. PC3, and DU-145 cell lines are as indicated. The designation FT indicates sequence derived from a frozen human prostatic adenocarcinoma. Only the normal pp32 sequence, hpp32, was obtained from normal prostate adjacent to tumor tissue. FIG. 8A shows alignment of the amplicon nucleotide sequences with pp32 and the predicted amplicon from pp32r1. FIG. 8B shows alignment of the predicted protein sequences. One sequence (FT 1.11), independently obtained three times from two separate patients and the TSUPR-1 cell line, is shown only once in the diagram. The pileup and pairwise alignments illustrate several important points: [1] there is a high degree of sequence conservation at both the nucleotide and predicted amino acid levels; [2] the sequence differences are distributed throughout the length of the sequence without obvious hotspots: [3] there is no obvious clustering or segmentation of sequence differences: and [4] the variant sequences fall into the previously described groups. These points are detailed in FIGS. 8A and 8B.

Example 8

Diagnostic Method to Distinguish Among Family Members

The three members of the pp32 family which are expressed in human prostate cancer are pp32, pp32r1 and pp32r2. Whereas pp32 suppresses in vitro transformation and in vivo tumorigenesis in model systems, pp32r1 and pp32r2 are pro-transforming and are tumorigenic in the same systems. It is possible to determine which of the three members is expressed in a tissue sample by using a protocol similar to that described in Example 7.

Analysis from freshly frozen human tissue and cell lines. Total RNA is extracted from freshly frozen human tissues or human cancer cell lines and subjected to reverse transcription and polymerase chain reaction amplification with single set of primers capable of amplifying the entire coding region of the cDNA of all the three genes. A suitable set of primers is:

Upper: 5'GGGTTCGGGGITTATTG3'-(SEQ ID NO: 47)
  This corresponds to bp32 to bp48
  of the pp32 cDNA sequence (Genbank U73477)
Lower: 5'CTCTAATCCTGCCCCCTGAAA3'-(SEQ ID NO: 48) This corresponds to bp919
  of bp938 of the pp32 cDNA sequence (Genbank U73477)
The observed amplicon sizes with this primer set are pp32–907 bp, pp32r1–889 bp and pp32r2–900 bp. The three cDNAs are distinguished from each other by restriction enzyme digestion with the following enzymes—EcoRI, HindIII and Xho I. The resultant digest is run on a 2.5% agarose gel to positively identify the three different cDNAs. The table below lists the sizes of the bands observed. The bolded numbers indicate the band sizes useful for identification of the three cDNAs.

TABLE 4A

Expected band sizes upon restriction digestion of the RT-PCR product from fresh tissue and cell lines

|  | Undigested | EcoR I | EcoR I/Hind III Double digest | EcoR I/Xho I Double digest |
|---|---|---|---|---|
| hpp32 | 907 | 21.177,709 | 21.177.69.640 | 21.177,709 |
| pp32r1 | 889 | 21.177,691 | 21.19.66.198,427 | 21.177,691 |
| pp32r2 | 900 | 21.879 | 21.244.635 | 21.385,494 |

Analysis from formalin fixed and paraffin embedded tissue. A similar approach is followed for identification of pp32, pp3r1 and pp32r2 transcripts from formalin fixed and paraffin embedded tissues. Total RNA is extracted and subjected to reverse transcription and PCR amplification with a single set of primers capable of amplifying a stretch of 200 bp from all the three cDNAs. A suitable set of primers is:
  Upper primer—from bp394 to bp414 of the pp32 cDNA sequence (Genbank U73477)
  Lower primer—from bp609 to bp629 of the pp32 cDNA sequence (Genbank U73477)

The three cDNAs are distinguished from each other by restriction enzyme digestion with the following enzymes—Hind III. Xho I and BseR I. The resultant digest is-run on a 3% agarose gel to positively identify the three different cDNAs. The table below lists the sizes of the bands observed. The bolded numbers indicate the band sizes useful for identification of the three cDNAs.

TABLE 5A

Expected band sizes upon restriction digestion of the RT-PCR product from formalin fixed and paraffin embedded tissues

|  | Undigested | Hind III | Xho I | BseR I |
|---|---|---|---|---|
| hpp32 | 200 | 200 | 200 | 80,120 |
| pp32r1 | 200 | 100,100 | 200 | 200 |
| pp32r2 | 200 | 200 | 44,156 | 80,120 |

Figure 8:
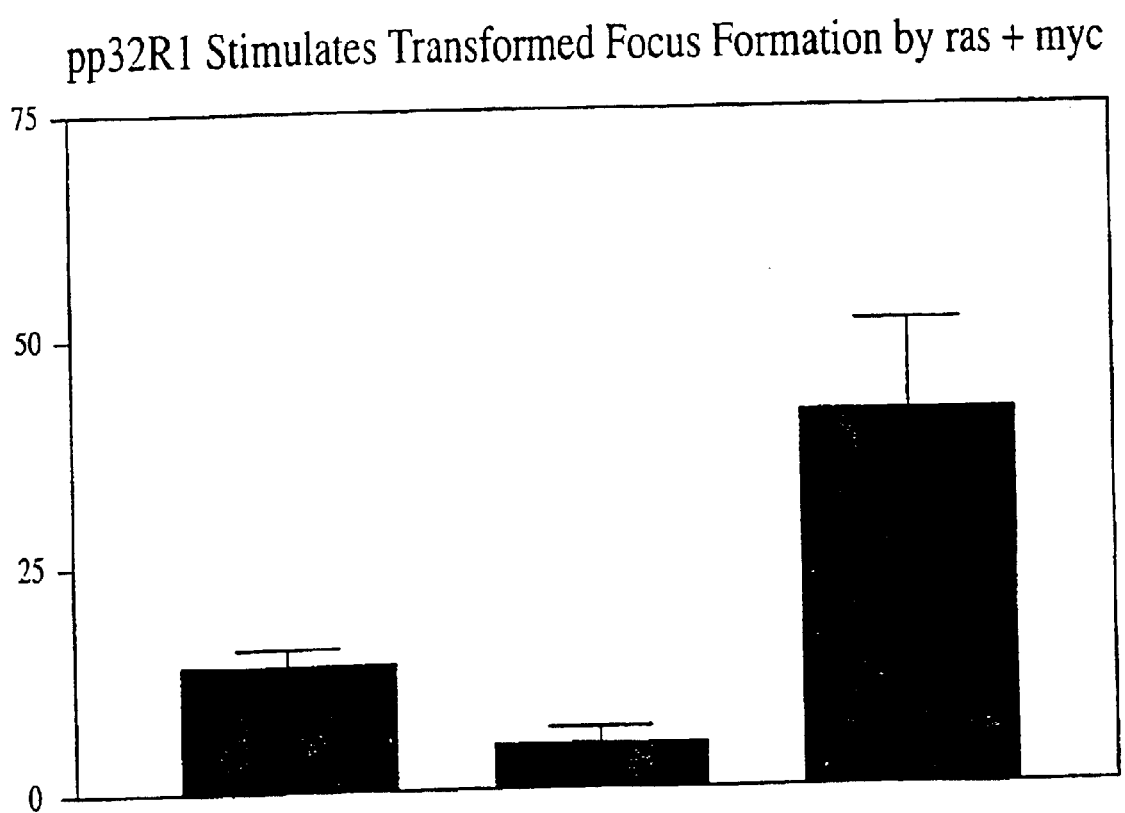
FIG. 8 is a bar graph showing ras+myc induced transformed focus formation. Co-transfection with a pp32 expression vector reduces transformation. While co-transfection with a pp32r1 expression vector stimulates transformation.

Example 9 pp32r1 Augments Oncogene-Mediated Transformation of Rat Embryo Fibroblasts.

pp32r1 was subcloned into a eukaryotic expression vector under the CMV promoter and analyzed for its effect on ras+myc-mediated formation of transformed foci in rat embryo fibroblasts. Genomic sequences including the entire coding region for pp32r1 were amplified by PCR and subcloned into the eukaryotic TA cloning and expression vector pCR3.1 vector (Invitrogen) which contains a CMV promoter. The assay was performed as described (Chen, et al. Mol Biol Cell. 7:2045–56, 1996) with each T75 flask receiving 5 micrograms of pEJ-ras, and/or 10 micrograms of pMLV-c-myc, pCMV32, pp32r1 in PCR3.1, or PCR 3.1 alone. After 14 days, transformed colonies were enumerated. FIG. 8 shows the results. The data represent the average of seven replicates from two separate experiments in duplicate and one in triplicate. The error bars indicate standard error of the mean. In contrast to pp32, which consistently suppresses focus formation induced by ras+myc and other oncogene pairs, pp32r1 caused a statistically significant stimulation of focus formation with p=0.004 by an unpaired t-test.

Example 10

Figure 9:
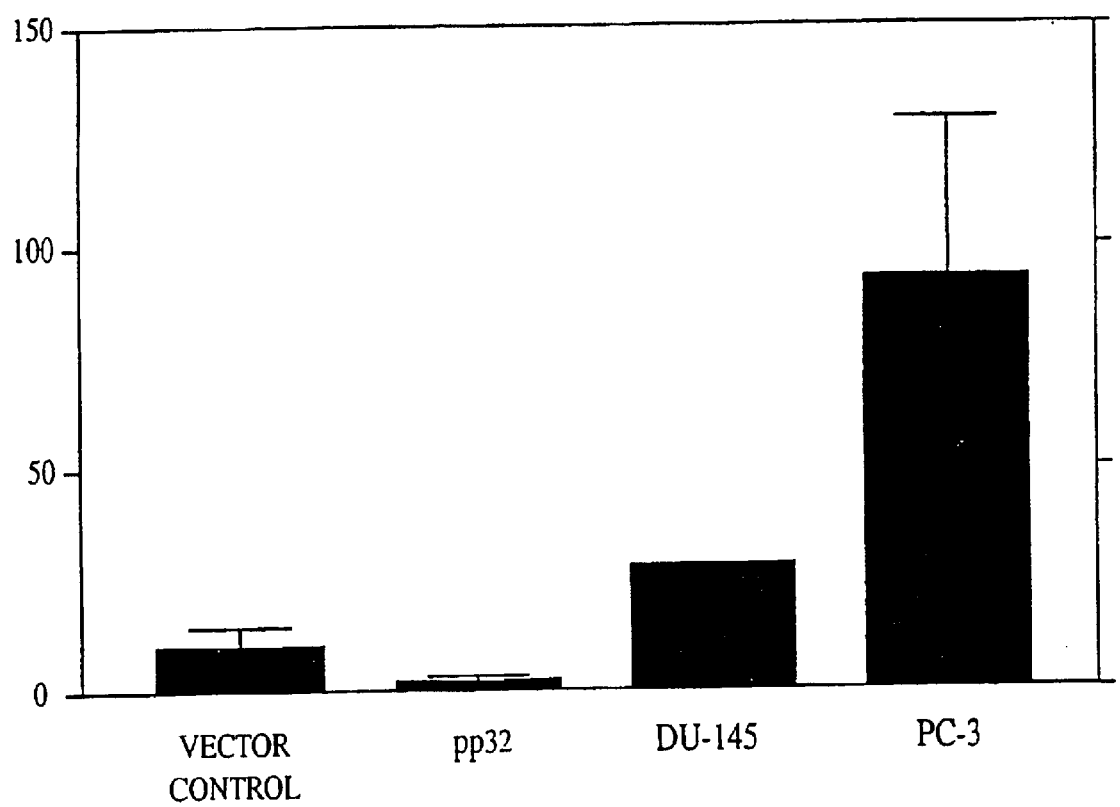
FIG. 9 is a bar graph showing pp32r1 stimulation of ras+myc induced transformed focus formation. Co-transfection with a pp32 expression vector reduces transformation, while co-transfection with expression vectors for pp32r1 sequences from prostate cancer cell lines stimulate transformation.

Effect of Transcripts from Various Cell Lines on Rat Fibroblast Transformation Assays Expression constructs prepared as described above from PC-3 and DU-145 cells were tested in the rat embryo fibroblast transformation assay described by Chen, et al., Mol Biol Cell., 7:2045–56, 1996, incorporated herein by reference. The results are shown in FIG. 9. Transcripts from the two cell lines stimulated ras+myc induction of transformed rat embryo fibroblast foci, in contrast to normal pp32, which suppressed transformation. The figure shows the mean+/− the standard deviation, except for DU-145, which represents a single determination.

Example 11

Transformation Activity of Various Isolates from Patient Tumors

Figure 10:
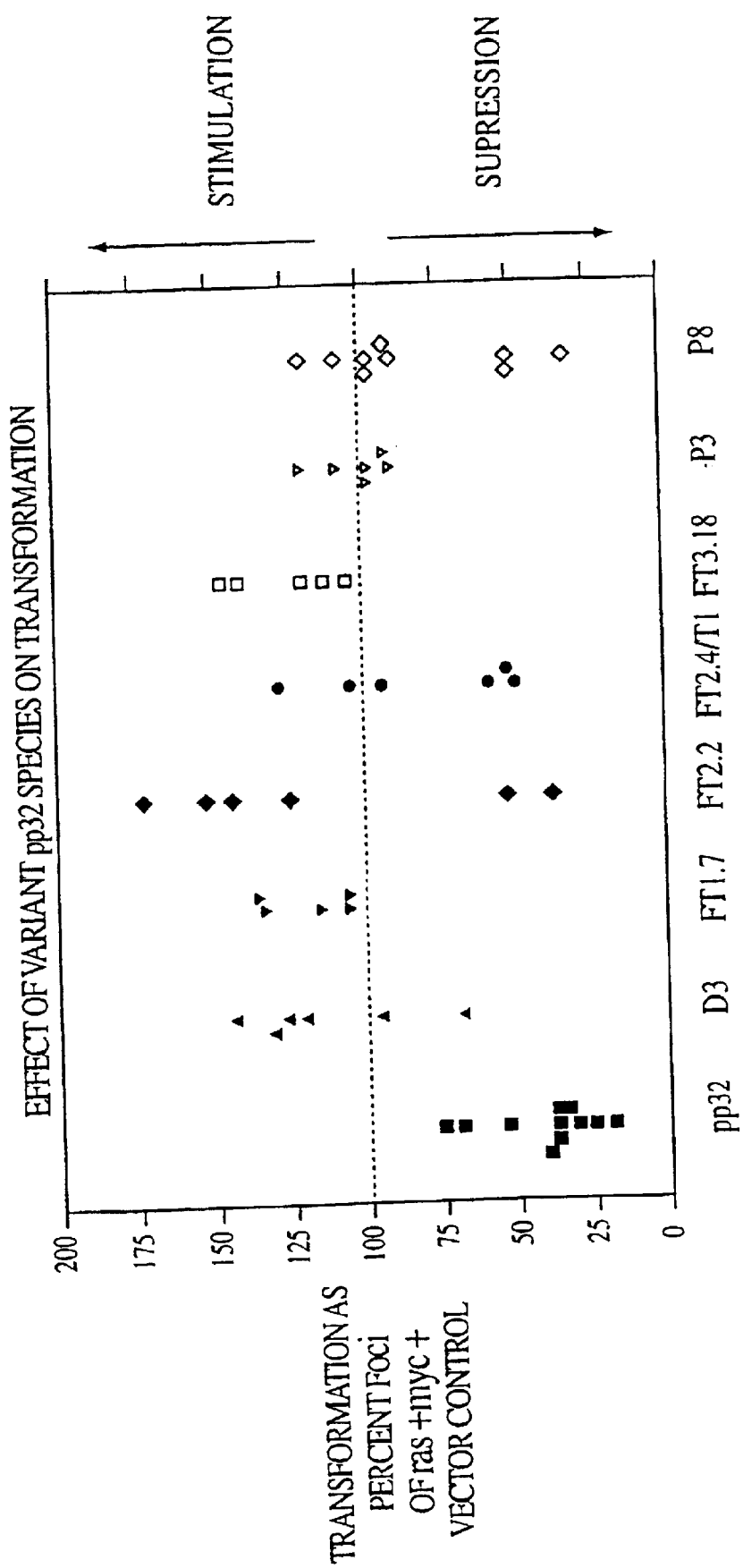
FIG. 10 is a graph of transformation assay results for cells transfected with variant pp32 species, which are shown to stimulate transformation with variable potency.

The variant transcripts isolated from prostate cancer patients differ significantly from pp32 in sequence. The isolated transcripts were found to stimulate transformation. Transformation assay. Rat embryo fibroblasts were transfected with the indicated constructs as described (Chen, et al.) and transformed foci enumerated. For each experiment, approximately $1 \times 10^6$ cells were plated per T75 flask and incubated for 2 to 3 d prior to transfection to achieve approximately 40% confluency. For each flask of primary rat embryo fibroblasts, the plasmids indicated in each experiment were added in the following amounts: pEJ-ras, 5 $\mu$g; and pMLV-c-myc, pCMV32, pCMVneo, or variant pp32 constructs in pCR3.1 (Invitrogen), 10 $\mu$g. Plasmids were prepared in two volumes Lipofectin (2 $\mu$l lipofectin per $\mu$g DNA) then gently mixed by inversion in 1.5 ml OPTIMEM in sterile 15 ml polystyrene tubes and allowed to incubate at room temperature for>15 min. For experiments with more than one ask, mixtures of all reagents were increased in proportion to the numbers of flasks required for each transfection. Cells were washed once with OPTIMEM (Gibco-BRL), and then fed with 6 ml of OPTIMEM and 1.5 ml of the DNA/Lipofectin mix. After overnight incubation, the cells were grown in standard media and refed with fresh media twice weekly. Foci were counted fourteen days post-transfection. FIG. 10 summarizes four separate experiments. Each data point represents the results from an individual flask expressed as the percent foci obtained in the contemporaneous control of ras+myc+vector.

FIG. 10 shows that expressed variant transcripts from prostate cancer cell lines and from human prostatic adenocarcinoma generally produce increased numbers of transformed foci when co-transfected with ras and myc, as compared to the number of foci obtained when ras and myc are transfected with blank vector. Variant pp32 transcripts from DU-145 (D3), and from three prostate cancers (FT 1.7. FT 2.2, and FT3.18) yield increased numbers of transformed foci over those produced by ras and myc alone with blank vector. This stands in marked contrast to normal pp32, which consistently suppresses transformation. These activities are also summarized in Table 1.

Example 12

Effect of pp32 Variants on Tumorigenesis In Vivo

Experiments testing the effect of transfection of NIH3T3 cells on tumorigenesis in vivo are consistent with in vivo results in rat embryo fibroblasts. NIH3T3 cells were stably transfected by lipofection with the pp32 species indicated in Table 6A carried in the pCR3.1-Uni CMV-driven mammalian expression vector (Invitrogen). The G418-resistant clones employed in these experiments were all shown by genomic PCR to carry the indicated pp32 species. For analysis of tumorigenesis. $5 \times 10^6$ cells in 100 microliters of unsuppiemented Dulbecco's modified Eagle's medium without phenol red were infected into the flanks of female athymic nude mice on an outbred background of greater than six weeks in age (Harlan). For logistical reasons, inoculations a the various groups were staggered over a seven day period. Each group of mice was euthanized precisely seven weeks after inoculation. Where a mouse had a tumor, the tumor was dissected, measured, and weighed, and Table 6A reports the average weight of tumors in mice injected with cells carrying various vectors. One tumor from each group was examined histologically. All tumors were fibrosarcomas without noteworthy inflammation present. Data obtained with NIH31T3 cells indicate that NIH3T3 cells stably transfected with the variant pp32 species P3, P8, FT1.7, FT2.2, and FF2.4 form tumors when inoculated into nude mice. In contrast. NIH3T3 cells stably transfected to express human pp32 fail to form tumors in vivo even when further transfected with ras. Lines of NIH3T3 cells were also established that were stably transfected with expression constructs encoding pp32 or pp32-antisense. Basal expression of pp32 is essential for maintenance of contact inhibition and serum-dependent cell growth: antisense ablation of endogenous pp32 synthesis permitted cells to grow normally following serum withdrawal. Constitutive over-expression of pp32 potently suppressed ras-mediated transformation of NIH3T3 cells in vitro and tumorigenesis in vivo. In contrast, antisense ablation of endogenous pp32 dramatically increased the number and size of ras-transformed foci; in vivo, tumors obtained from ras-transformed antisense pp32 cells were approximately 50-fold greater in mass than tumors obtained from ras-transformed control cells.

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in medicine, immunology, hybridoma technology, pharmacology, pathology, and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

TABLE 1

| Position | Factor Strand | Consensus Sequence | |
|---|---|---|---|
| 4 | C | TTTCCT | PEA3 |
| 21 | N | CAAGGTCA | ELP |
| 23 | N | AGGTCA | PPAR |
| 32 | C | CCCTAA | TBFI |
| 41 | N | CTTGGC | NF-1 (-like proteins) |
| 81 | N | TAAACAC | Pit-1 |
| 82 | N | AAACACA | HiNF-A |
| 113 | C | CTTCCC | c-Ets-2 |
| 118 | N | CTATCA | GATA-1 |
| 122 | N | CAGTTG | c-Myc |
| 212 | C | AATAAATA | TFIID |
| 213 | N | ATAAATA | ETF |
| 247 | N | TATCTA | NIT2 |
| 261 | C | AAGGAA | c-Ets-2 |
| 262 | B | AGGAAA | PEA3 |
| 283 | C | TTTTTCTTTTTC | Hb (SEQ ID NO:49) |
| 320 | C | TTATAT | GAL4 |
| 333 | N | TAAAAAA | TBP |
| 349 | N | TTATACATT | TBP |
| 363 | C | AAGGAA | c-Ets-2 |
| 394 | C | TTTCTATA | TBP |
| 398 | N | TATAAA | TBP |
| 398 | N | TATAAA | TFIID |
| 411 | C | CTGAATT | Pit-1 |
| 420 | N | TGTCCC | GR |
| 423 | C | CCCTAA | TBF1 |
| 434 | N | TTCCTT | c-Ets-2 |
| 447 | C | CTTCCC | c-Ets-2 |
| 514 | N | TTATCTCT | GATA-1 |
| 514 | C | TTATCT | GATA-2 |
| 515 | N | TATCTC | NIT2 |

TABLE 1-continued

| Position | Factor Strand | Consensus Sequence | |
|---|---|---|---|
| 537 | N | TATGCA | EFII |
| 553 | N | AAGTCA | GCN4 |
| 608 | N | TGACTA | GCN4 |
| 628 | N | CCTCCCAAC | LyF-1 |
| 640 | N | TGTCCT | GR |
| 648 | N | TTAAAATTCA | 1-Oct (SEQ ID NO:50) |
| 648 | N | TTAAAATTCA | 4-Oct (SEQ ID NO:50) |
| 649 | N | TAAAAT | F2F |
| 649 | N | TAAAAT | Pit-1 |
| 661 | N | TAAAAAA | TBP |
| 673 | N | CTTGGC | NF-1 (like proteins) |
| 725 | N | AGGCGG | Sp1 |
| 729 | N | GGGCGG | ETF |
| 729 | N | GGGCGG | Sp1 |
| 729 | C | GGGCGG | Sp1 |
| 741 | N | AGGTCA | PPAR |
| 793 | N | TATAAATA | B factor |
| 793 | N | TATAAA | TBP |
| 793 | N | TATAAATA | TFIID |
| 793 | N | TATAAAT | TMF |
| 794 | N | ATAAATA | ETF |
| 809 | N | TTATCT | GATA-1 |
| 809 | C | TTATCT | GATA-2 |
| 815 | N | GGGTGTGG | TEF-2 |
| 826 | C | CACATG | muEBP-C2 |
| 826 | C | CACATG | TFE3-S |
| 826 | C | CACATG | USF |
| 978 | N | ATGTAAAACA | 1-Oct (SEQ ID NO:51) |
| 978 | N | ATGTAAAACA | 2-Oct (SEQ ID NO:51) |
| 978 | N | ATGTAAAACA | NF-IL-2A (SEQ ID NO:51) |
| 1000 | N | ATGTCAGA | CSBP-1 |
| 1006 | N | GATTTC | H4TF-1 |
| 1034 | C | TTTTCAT | Pit-1 |
| 1047 | N | AAGATAAAACC | RVF (SEQ ID NO:52) |
| 1048 | N | AGATAA | GATA-1 |
| 1048 | C | AGATAA | GATA-2 |
| 1049 | N | GATAAA | TFIID |
| 1083 | C | GCCAAG | NF-1 (-like proteins) |
| 1124 | N | CGCCAT | UCRF-L |
| 1163 | C | GACCTG | TGT3 |
| 1307 | N | CAGTCA | GCN4 |
| 1347 | C | TGCATA | EFII |
| 1373 | C | AGAACA | AR |
| 1373 | N | AGAACAT | GR |
| 1373 | N | AGAACA | GR |
| 1373 | C | AGAACA | GR |
| 1373 | N | AGAACA | PR |
| 1373 | C | AGAACA | PR |
| 1373 | N | AGAACA | PR A |
| 1373 | C | AGAACA | PR A |
| 1393 | C | TCACTT | IFG-1 |
| 1393 | C | TCACTT | IRF-2 |
| 1395 | C | ACTTCCT | EIA-F |
| 1423 | N | TTATCT | GATA-1 |
| 1423 | C | TTATCT | GATA-2 |
| 1424 | N | TATCTA | NIT2 |
| 1452 | N | TTACTC | GCN4 |
| 1471 | N | TGGGTCA | C-Fos |
| 1471 | N | TGGGTCA | c-Jun |
| 1471 | N | TGGGTCA | ER |
| 1496 | N | TCTCTTA | c-Myc |
| 1511 | N | TATAAA | TBP |
| 1511 | N | TATAAA | TFIID |
| 1549 | C | TITGAA | TFlID |
| 1568 | C | AATGTATAA | TBP |
| 1581 | C | TTTGAA | TFIID |
| 1590 | C | AGATAA | GATA-1 |
| 1590 | N | AGATAA | GATA-2 |
| 1591 | C | GATAATTG | Dfd |
| 1657 | C | AGGACA | GR |
| 1670 | C | ATTTTA | F2F |
| 1670 | C | ATTTTA | Pit-1 |
| 1671 | C | TTTTATA | B factor |
| 1671 | C | TTTTATA | Dr1 |
| 1671 | C | TTTTATA | En |
| 1671 | C | TTTTATA | TBP |

TABLE 1-continued

| Position | Factor Strand | | Consensus Sequence |
|---|---|---|---|
| 1671 | C | TTTTATA | TBP-1 |
| 1671 | C | TTTTATA | TFIIA |
| 1671 | C | TTTTATA | TFIIB |
| 1671 | C | TTTTATA | TFIID |
| 1671 | C | TTTTATA | TFIIE |
| 1671 | C | TTTTATA | TFIIF |
| 1671 | C | TTTTATA | TRF |
| 1672 | C | TTTATA | TBP |
| 1694 | C | AATAAATA | TFIID |
| 1695 | N | ATAAATA | ETF |
| 1733 | N | AGGAAA | PEA3 |
| 1749 | C | TTATAT | GAL4 |
| 1783 | N | TAACTCA. | AP-1 |
| 1829 | N | TAGATA | NIT2 |
| 1857 | N | CGCCAT | UCRF-L |
| 1875 | N | TTCTGGGAA | IL-6 RE-BP |
| 1895 | N | TGACTA | GCN4 |
| 1899 | N | TATTTAA | TBP |
| 1942 | N | ATATAA | GAL4 |
| 1985 | C | TTTATA | TBP |
| 1985 | C | TTTATA | TFIID |
| 2010 | C | AATAAATA | TFIID |
| 2011 | N | ATAAATA | ETF |
| 2058 | C | TGCATA | EFII |
| 2095 | N | CAGTCA | GCN4 |
| 2146 | N | AAGGAA. | c-Ets-2 |
| 2147 | N | AGGAAA | PEA3 |
| 2190 | N | AGGAAA | PEA3 |
| 2220 | C | GGCACA | GR |
| 2252 | C | CCAATAG | gammaCAAT |
| 2286 | N | TGTGCC | GR |
| 2292 | N | ATGGGA | PTF1-beta |
| 2314 | N | TATGCA | EFII |
| 2328 | C | GGCACA | GR |
| 2350 | C | ATGATAAG | GATA-1 |
| 2351 | N | TGATAAG | GATA-1 |
| 2363 | N | GGGAAG | c-Ets-2 |
| 2367 | N | AGCCACT | CP2 |
| 2369 | C | CCACTGGGGA | AP-2 (SEQ ID NO:53) |
| 2404 | N | TAAAAT | F2F |
| 2404 | N | TAAAAT | F2F |
| 2404 | N | TAAAAT | Pit-1 |
| 2409 | N | TTGTCATA | 77 + 82K protein |
| 2409 | N | TTGTCATA | VETF |
| 2415 | N | TATCTA | NIT2 |
| 2451 | C | TTTATC | TFIID |
| 2452 | N | TTATCT | GATA-1 |
| 2452 | C | TTATCT | GATA-2 |
| 2486 | N | CTCTCTCTCTCTC | GAGA factor (SEQ ID NO:54) |
| 2644 | N | AGGCGG | Sp1 |
| 2658 | N | ACAGCTG | GT-IIBalpha |
| 2658 | N | ACAGCTG | GT-IIBbeta |
| 2709 | C | GGCCAGGC | AP-2 |
| 2723 | N | TGA4CT | GR |
| 2731 | N | TGACCT | PPAR |
| 2731 | C | TGACCTCA | URTF |
| 2753 | N | CTTGGC | NF-1 (-like proteins) |
| 2818 | C | TGATGTCA | AP-1 |
| 2818 | C | TGATGTCA | c-Fos |
| 2818 | C | TGATGTCA | c-Jun |
| 2818 | C | TGATGTCA | CREB |
| 2845 | N | GGGAAG | c-Ets-2 |
| 2858 | N | AGATAG | GATA-1 |
| 2858 | N | AGATAG | GATA-1 |
| 2864 | C | AGTTCA | GR |
| 2899 | N | ATATAA | GAL4 |
| 2900 | N | TATAAAA | B factor |
| 2900 | N | TATAAAA | Dr1 |
| 2900 | N | TATAAAA | En |
| 2900 | N | TATAAAA | TBP |
| 2900 | N | TATAAA | TBP |
| 2900 | N | TATAAAA | TBP-1 |
| 2900 | N | TATAAAA | TFIIA |
| 2900 | N | TATAAAA | TFIIB |
| 2900 | N | TATAAAA | TFIID |
| 2900 | N | TATAAAA | TFIIE |
| 2900 | N | TATAAAA | TFIIF |
| 2900 | N | TATTAAAA | TRF |
| 2921 | C | TTTGAA | TFIID |
| 2924 | C | GAAATC | H4TF-1 |
| 2930 | C | CATTAG | IsI-1 |
| 2948 | C | TGTACA | GR |
| 2948 | C | TGTACA | PR |
| 2948 | C | TGTACA | PR A |
| 2964 | C | ATTTGAGAA | VITF |
| 3030 | N | AGTGTTCT | GR |
| 3032 | N | TGTTCT | AR |
| 3032 | N | TGTfCT | GR |
| 3032 | C | TGTfCT | GR |
| 3032 | N | TGTTCT | PR |
| 3032 | C | TGTTCT | PR |
| 3032 | N | TGTTCT | PR A |
| 3032 | C | TGTTCT | PR A |
| 3104 | C | GGATTATT | TII |
| 3106 | C | ATTATTAA | AFP1 |
| 3111 | N | TAAAAT | F2F |
| 3111 | N | TAAAAT | Pit-1 |
| 3125 | C | ATTTTA | F2F |
| 3125 | C | ATTTTA | Pit-1 |
| 3142 | N | TGTGAT | GR |
| 3169 | N | GTTTTATT | HOXD10 |
| 3169 | N | GTTTTATT | HOXD8 |
| 3169 | N | GTTTTATT | HOXD9 |
| 3175 | C | TTTGAA | TFIID |
| 3185 | N | TTGCTCA | Zta |
| 3206 | C | GATTTC | H4TF-1 |
| 3212 | N | AGGAAA | PEA3 |
| 3238 | C | ATTTTA | F2F |
| 3238 | C | ATTTTA | Pit-1 |
| 3256 | C | TTTGAA | TFIID |
| 3266 | N | TTGCTCA | Zta |
| 3320 | C | ATTTTA | F2F |
| 3320 | C | ATTTTA | Pit-1 |
| 3358 | N | ATGGGA | PTF1-beta |
| 3360 | C | GGGACA | GR |
| 3440 | C | CACTCA | GCN4 |
| 3460 | C | TTTCCT | PEA3 |
| 3483 | N | GACACA | GR |
| 3491 | C | TTTCCT | PEA3 |
| 3495 | N | CTAATG | IsI-1 |
| 3523 | C | AGAACA | AR |
| 3523 | N | AGAACA | GR |
| 3523 | C | AGAACACT | GR |
| 3523 | C | AGAACA | GR |
| 3523 | N | AGAACA | PR |
| 3523 | C | AGAACA | PR |
| 3523 | N | AGAACA | PR A |
| 3523 | C | AGAACA | PR A |
| 3538 | C | TTTATC | TFIID |
| 3539 | N | TTATCT | GATA-1 |
| 3539 | C | TTATCT | GATA-2 |
| 3551 | N | TGAGTG | GCN4 |
| 3569 | C | TCCCAT | PTF 1-beta |
| 3594 | N | TTAGGG | TBF1 |
| 3653 | C | CCTGCTGAA | LyF-1 |
| 3668 | C | CTCATGA | 1-Oct |
| 3668 | C | CTCATGA | 2-Oct |
| 3668 | N | CTCATGA | Oct-2B |
| 3668 | N | CTCATGA | Oct-2B |
| 3668 | N | CTCATGA | Oct-2C |
| 3679 | C | TGTGTAA | Zta |
| 3685 | C | AGAACT | GR |
| 3712 | C | TTTCCT | PEA3 |
| 3713 | N | TTCCTT | c-Ets-2 |
| 3717 | N | TTGCTCA | Zta |
| 3727 | C | AAAACATAAAT | ssARS-T (SEQ ID NO:55) |
| 3749 | N | TAAAAAA | TBP |
| 3784 | C | CACTCA | GCN4 |
| 3791 | C | ATTTTA | F2F |
| 3791 | C | ATTTTA | Pit-1 |
| 3815 | N | TATCTA | NIT2 |
| 3829 | C | TAGATA | NIT2 |

TABLE 1-continued

| Position | Factor Strand | Consensus | Sequence |
|---|---|---|---|
| 3859 | C | AGAACA | AR |
| 3859 | N | AGAACAG | GR |
| 3859 | N | AGAACA | GR |
| 3859 | C | AGAACA | GR |
| 3859 | N | AGAACA | PR |
| 3859 | C | AGAACA | PR |
| 3859 | N | AGAACA | PR A |
| 3859 | C | AGAACA | PR A |
| 3860 | N | GAACAG | Lva |
| 3877 | C | ATCACA | GR |
| 3886 | N | TGAGTCA | AP-1 |
| 3886 | C | TGAGTCA | AP-1 |
| 3886 | C | TGAGTCA | c-Fos |
| 3886 | C | TGAGTCA | c-Jun |
| 3886 | C | TGAGTCA | Fra1 |
| 3886 | C | TGAGTCA | NF-E2 |
| 3887 | C | GAGTCA | GCN4 |
| 3931 | N | AGATAG | GATA-1 |
| 3931 | C | AGATAG | GATA-1 |
| 3960 | N | TTGGCA | NF-I/L |
| 3965 | C | ATTTTA | F2F |
| 3965 | C | ATTTTA | Pit-1 |
| 4026 | N | TATTTAA | TBP |
| 4037 | N | TCTGAT | GR |
| 4040 | N | GATGCAT | Pit-1 |
| 4042 | C | TGCATA | EFII |
| 4079 | N | TTCAAAG | SRY |
| 4079 | N | TTCAAAG | TCF-1A |
| 4079 | N | TTCAAA | TFIID |
| 4079 | N | CAGGTC | TGT3 |

TABLE 1-continued

| Position | Factor Strand | Consensus | Sequence |
|---|---|---|---|
| 4140 | N | TGATTCA | AP-1 |
| 4140 | C | TGATTCA | AP-1 |
| 4140 | N | TGATTC | GCN4 |
| 4164 | N | GGGAGTG | p300 |
| 4205 | C | AGATAA | GATA-1 |
| 4205 | N | AGATAA | GATA-2 |
| 4219 | C | TTAGTCAC | AP-1 |
| 4219 | C | TTAGTCA | AP-1 |
| 4219 | C | TTAGTCAC | c-Fos |
| 4219 | C | TTAGTCAC | c-Jun |
| 4219 | C | TTAGTCA | c-Jun |
| 4219 | C | TTAGTCA | Jun-D |
| 4220 | C | TAGTCA | GCN4 |
| 4271 | N | TGTTCT | AR |
| 4271 | N | TGTTCT | GR |
| 4271 | C | TGTTCT | GR |
| 4271 | N | TGTTCT | PR |
| 4271 | C | TGTTCT | PR |
| 4271 | N | TGTTCT | PR A |
| 4271 | C | TGTTCT | PR A |
| 4280 | C | TGACCCA | c-Fos |
| 4280 | C | TGACCCA | c-Jun |
| 4280 | C | TGACCCA | ER |
| 4292 | C | CTTATCAG | GATA-1 |
| 4292 | C | CTTATCA | GATA-1 |
| 4361 | N | TTCAAAG | SRY |
| 4361 | N | TTCAAAG | TCF-1A |
| 4361 | N | TTCAAA | TFIID |

TABLE 2

COMPARISON OF ALL PROTEIN SEQUENCES

| | 1 | 15 | 16 | 30 | 31 | 45 | 46 | 60 | 61 | 75 | 76 | 90 |
|---|---|---|---|---|---|---|---|---|---|---|---|---|
| TSU6 | MEMGRRIHLELRNGT | | PSDVKELVLDNSRSN | | EGKLEGLTDEFEELE | | FLSTINVGLTSIANL | | PKLNKLKKLELSSNR | | ASVGLEVLAEKCPNL | |
| D3 | MEMGRRIHLELRNRT | | PSDVKELVLDNSRSN | | EGKLEGLTDEFEELE | | FLSTINVGLTSIANL | | PKLNKLKKLELSDNR | | VSVGLEVLAEKCPNL | |
| PG | MEMGRRIHLELRNRT | | PSDVKELFLDNSQSN | | EGKLEGLADEFEELE | | LLNTINIGLTSIANL | | AKLNKLKKLELSDNR | | ASVGLEVLAEKCPNL | |
| FT1.11 | MEMGKWIHLELRNRT | | PSDVKELFLDNSQSN | | EGKLEGLTDEFEELE | | LLNTINIGLSSIANL | | PKLNKLKKLELSSNR | | ASVGLEVLAEKCPNL | |
| TSU1 | MEMGKWIHLELRNRT | | PSDVKELFLDNSQSN | | EGKLEGLTDEFEELE | | LLNTINIGLTSIANL | | PKLNKLKKLELSSNR | | ASVGLEVLAEKCPNL | |
| FT3.18 | MEMGKWIHLELRNRT | | PSDVKELFLDNSQSN | | EGKLEGLTDEFEELE | | LLNTINIGLTSIANL | | PKLNKLKKLELSSNR | | ASVGLEVLAEKCPNL | |
| FT2.4 | MEMGRRIHLELRNRT | | PSDVKELFLDNSRSN | | EGKLEGLTDEFEELE | | FLSTINVGLTSIANL | | PKLNKLKKLELSSNR | | ASVGLEVLAEKCPNL | |
| FT2.2 | MEMGRRIHSELRNRA | | PSDVKELALDNSRSN | | EGKLEALTDEFEELE | | FLSKINGGLTSISDL | | PKL-KLRKLEI---K | | VSGGLEVLAEKCPNL | |
| KG | MEMGRRIHSELRNRA | | PSDVKELALDNSRSN | | EGKLEALTDEFEELE | | FLSKINGGLTSISDL | | PKL-KLRKLEI---R | | VSGGLEVLAEKCPNL | |
| FT1.7 | MEMGRRIHLELRNRT | | PSDVKELFLDNSRSN | | EGKLEGLTDEFEELE | | FLSTINVGLTSIANL | | PKLNKLKKLELSDNR | | ASVGLEVLAEKCPNL | |
| P3 | MEMGRRIHLELRNRT | | PSDVKELVLDNSRSN | | EGKLEGLTDEFEELE | | LLNTINIGLTSIANL | | PKLNKLKKLELSSNR | | VSGGLEVLAEKCPNL | |
| pp32 | MEMGRRIHLELRNRT | | PSDVKELVLDNSRSN | | EGKLEGLTDEFEELE | | FLSTINVGLTSIANL | | PKLNKLKKLELSSNR | | VSGGLEVLAEKCPNL | |
| P8 | MEMGRRIHLELRNRT | | PSDVKELVLDNSRSN | | EGKLEGLTDEFEELE | | FLSTINVGLTSIANL | | PKLNKLKKLELSSNR | | ASVGLEVLAEKCPNL | |

| | 91 | 105 | 106 | 120 | 121 | 135 | 136 | 150 | 151 | 165 | 166 | 180 |
|---|---|---|---|---|---|---|---|---|---|---|---|---|
| TSU6 | IHLNLSGNKIKDLST | | IEPLKKLENLESLDL | | FTCEVTNLNNY---- | | --------------- | | --------------- | | --------------- | |
| D3 | IHLNLSGNKIKDLST | | IEPLKKLENLESLDL | | FTCEVTNLNNY---- | | --------------- | | --------------- | | --------------- | |
| PG | IHLNLSGNKIKDLST | | IEPLKKLENLESLDL | | FTCEVTNLNNY---- | | --------------- | | --------------- | | --------------- | |
| FT1.11 | IHLNLSGNKIKDLST | | IEPLKKLENLESLDL | | FTCEVTNLNNY---- | | --------------- | | --------------- | | --------------- | |
| TSU1 | IHLNLSGNKIKDLST | | IEPLKKLENLESLDL | | FTCEVTNLNNY---- | | --------------- | | --------------- | | --------------- | |
| FT3.18 | IHLNLSGNKIKDLST | | IEPLKKLENLESLDL | | FTCEVTNLNNY---- | | --------------- | | --------------- | | --------------- | |
| FT2.4 | IHLNLSGNKIKDLST | | IEPLKKLENLESLDL | | FNCEVTNLNDYGENV | | FKLLLQLTYLDSCYW | | DHKEAPYSDIEDHVE | | GLDDEEEGEHEEEYD | |
| FT2.2 | THLYLSGNKIKDLST | | IEPLKQLENLKSLDL | | FNCEVTNLNDYGENV | | FKLLLQLTYLDSCYW | | DHKEAPYSDIEDHVE | | GLDDEEEGEHEEEYD | |
| KG | THLYLSGNKIKDLST | | IEPLKQLENLKSLDL | | FNCEVTNLNDYGENV | | FKLLLQLTYLDSCYW | | DHKEAPYSDIEDHVE | | GLDDEEEDEEEEYD | |
| FT1.7 | IHLNLSGNKIKDLST | | IEPLKKLENLESLDL | | FTCEVTNLNNYRENV | | FKLLPQLTYLDGYDR | | DDKEAPDSDAEGYVE | | GLDDEEEDEEEEYD | |
| P3 | THLNLSGNKIKDLST | | IEPLKKLENLKSLDL | | FNCEVTNLNDYRENV | | FKLLPQLTYLDGYDR | | DDKEAPDSDAEGYVE | | GLDDEEEDEEEEYD | |
| L3 | IHLNLSGNKIKDLST | | IEPLKKLENLESLDL | | FNCEVTNLNDYRENV | | FKLLPQLTYLDGYDR | | DDKEAPDSDAEGYVE | | GLDDEEEDEEEEYD | |
| pp32 | THLNLSGNKIKDLST | | IEPLKKLENLKSLDL | | FNCEVTNLNDYRENV | | FKLLPQLTYLDGYDR | | DDKEAPDSDAEGYVE | | GLDDEEEDEEEEYD | |
| P8 | IHLNLSGNKIKDLST | | IEPLKKLENLKSLDL | | SNCEVTNLNDYRENV | | --------------- | | --------------- | | --------------- | |

| | 181 | 195 | 196 | 210 | 211 | 225 | 226 | 240 | 241 | | | |
|---|---|---|---|---|---|---|---|---|---|---|---|---|
| TSU6 | --------------- | | --------------- | | --------------- | | --------------- | | --- | | | |
| D3 | --------------- | | --------------- | | --------------- | | --------------- | | --- | | | |
| PG | --------------- | | --------------- | | --------------- | | --------------- | | --- | | | |
| FT1.11 | --------------- | | --------------- | | --------------- | | --------------- | | --- | | | |
| TSU1 | --------------- | | --------------- | | --------------- | | --------------- | | --- | | | |
| FT3.18 | --------------- | | --------------- | | --------------- | | --------------- | | --- | | | |
| FT2.4 | --------------- | | --------------- | | --------------- | | --------------- | | --- | | | |
| FT2.2 | EDAQVVEDEEGEEEE | | EEGEEEDVSGGDEED | | EEGYNDGEVDGEEDE | | EELGEEERGQKRK-- | | --- | | | |
| KG | EDAQVVEDEEGEGEE | | EEGEEEDVSGGDEED | | EEGYNDGEVDGEEDE | | EELGEEERGQKRK-- | | --- | | | |
| FT1.7 | EDAQVVEDEEDEEDE | | EEGEEEDVSGEEEEE | | EEGYNDGEVDGEEDE | | EELGEEERGQKRKRE | | PEDEGEDDD | | | |
| P3 | EDAQVVEDEEDEEDE | | EEGEEEDVSGEEEEE | | EEGYNDGEVDGEEDE | | EELGEEERGQKRKRE | | PEDEGEDDD | | | |
| L3 | EDAQVVEDEEDEEDE | | EEGEEEDVSGEEEEE | | EEGYNDGEVDGEEDE | | EELGEEERGQKRKRE | | PEDEGEDDD | | | |
| pp32 | EDAQVVEDEEDEEDE | | EEGEEEDVSGEEEEE | | EEGYNDGEVDGEEDE | | EELGEEERGQKRKRE | | PEDEGEDDD | | | |
| P8 | EDAQVVEDEEDEEDE | | EEGEEEDVSGEEEEE | | EEGYNDGEVDGEEDE | | EELGEEERGQKRKRE | | PEDEGEDDD | | | |

| | | |
|---|---|---|
| TSU6 | 131 | (SEQ ID NO:28) |
| D3 | 131 | (SEQ ID NO:37) |
| PG | 131 | (SEQ ID NO:38) |
| FT1.11 | 131 | (SEQ ID NO:29) |
| TSU1 | 131 | (SEQ ID NO:29) |
| FT3.18 | 131 | (SEQ ID NO:29) |
| FT2.4 | 131 | (SEQ ID NO:39) |
| FT2.2 | 234 | (SEQ ID NO:4) |
| KG | 234 | (SEQ ID NO:5) |
| FT1.7 | 245 | (SEQ ID NO:31) |
| P3 | 249 | (SEQ ID NO:40) |
| L3 | 249 | (SEQ ID NO:29) |
| pp32 | 249 | (SEQ ID NO:40) |
| P8 | 249 | (SEQ ID NO:30) |

TSU6 and TSU1 from TSU cell line; D3 from DU-145 cell line; P3 and P8 from PC-3 cell line; FT1, FT2 and FT3 from patient carcinoma; LE from LNCAP; KG from placenta

TABLE 3

Comparison to pp32 Sequences

| CLONE | % Identity cDNA | % Identity Protein | % Similarity Protein |
|---|---|---|---|
| D3, DU-145 cells | 95 | 90 | 95 |
| P3, PC-3 | 86 | 94 | 96 |
| P8, PC-3 | 98 | 97 | 97 |
| FT1.11 | 97 | 86 | 92 |
| FT1.7 | 95 | 95 | 95 |
| FT2.2 | 94 | 85 | 88 |
| FT2.4 | 99 | 86 | 92 |
| FT3.18 | 99 | 90 | 94 |

TABLE 3A pp32 Homologs human pp32 (Genbank Locus HSU73477)
murine pp32 (Genbank Locus MMU73478)
human cerebellar leucine rich acidic nuclear protein (LANP) (Genbank Locus AF025684)
murine LANP (Genbank Locus AF022957)
murine RFC1 (Genbank Locus MUSMRFC, Accession NO. L23755)
11PP2a or human potent heat-stable protein phospatase 2a inhibitor (Genbank Locus HSU60823)
SSP29 (Genbank Locus H5U70439)
HLA-DR associated protein 1 (Genbank Locus HSPPHAPI, Accession No. X75090)
PHAPI2a (EMBL Locus HSPRAPI2A, Genbank Accession No. Y07569)
PHAPI2b (EMBL Locus HSPHAPI2B, Genbank Accession No. Y07570)
April (EMBL Locus HSAPRIL)

TABLE 1A

| Sequence | Sequence Group | Nucleotide Identity with pp32 | Gaps | Protein Identity with pp32 | Effect on Oncogene-Mediated Transformation | Comment |
|---|---|---|---|---|---|---|
| FT 1.3 | A | 99.8 | | 100 | Not Tested | Identical to pp32 |
| D1 | A | 99.9 | | 100 | Not tested | Identical to pp32 with 2 silent nt changes |
| L3 | A | 99.9 | | 100 | Not Tested | |
| D3 | U | 95.8 | 0 | 96.9 | Generally Stimulatory | Encodes truncated variant pp32 |
| D5 | U | 99.6 | 0 | 99.6 | Not Tested | |
| FT 1.2 | U | 92.9 | 1 | | Not tested | No ORF |
| P3 | U | 96.5 | 1 | 94.4 | Slightly Stimulatory | |
| P8 | U | 98.7 | 0 | 98.0 | Variable | |
| FT 1.11 | B | 92.4 | 2 | 89.3 | Not Tested | All sequences identical; appears to be product of pp32r2 |
| FT 2.4 | B | 92.4 | 2 | 89.3 | Variable | |
| T1 | B | 92.4 | 2 | 89.3 | | |
| T6 | U | 94.2 | 1 | 93.9 | Not Tested | Encodes truncated variant pp32 |
| FT 3.18 | U | 94.7 | 2 | 89.3 | Stimulatory | Encodes truncated variant pp32 |
| FT 2.2 | C | 94.4 | 3 | 87.6 | Stimulatory | Sequences differ by 1 nt. appears to be product of pp32r1 |
| FT 3.3 | C | 94.4 | 3 | 87.6 | not tested | |
| FT 1.7 | U | 95.9 | 2 | 91.4 | Stimulatory | |

TABLE 2A

| Protein | Genbank Accession | Length | Human pp32 | Human pp32r1 | Human pp32r2 | Human April | Murine pp32 |
|---|---|---|---|---|---|---|---|
| Human pp32 | HSU73477 | 249 | 100% | 88% Identity 2 gaps; Z = 77 | 84% Identity 0 gaps; Z = 73 | 71% Identity 3 gaps; Z = 58 | 89% Identity 1 gap; Z = 87 |
| Human pp32r1 | AF008216 | 234 | | 100% Identity | 785 Identity 2 gaps; Z = 65 | 61% Identity 5 gaps; Z = 15 | 90% identity 3 gaps; Z = 64 |
| Human pp32r2 | HSU71084 | 131 | | | 100% Identity | 61% Identity 3 gaps; Z = 52 | 77% Identity 1 gap; Z = 80 |
| Human April | Y07969 | 249 | | | | 100% | 71% Identity 4 gaps; Z = 68 |
| Murine pp32 | U734778 | 247 | | | | | 100% Identity |

Percent amino acid identity of pp32 and related proteins. Sequences were aligned using the GAP program (7). The number of gaps in the alignment is indicated as well as the Z score, a statistical measure of protein relatedness derived from 50 comparisons of randomized protein sequences.

TABLE 6A

Tumorigenicity in Nude Mice of HIH3T3 Cells Transfected with pp32 and pp32 Variants

| pp32 Species | Clone | Tumors/ | Average Tumor Weight |
|---|---|---|---|
| FT1.7 | 1 | 3/3 | 14.9 ± 2.1 |
| | 2[1] | 3/3 | 13.3 ± 3.7 |
| FT2.2 | 1 | 3/3 | 10.5 ± 2.8 |
| | 2 | 3/3 | 3.8 ± 2.1 |
| FT2.4 | 1 | 3/3[6] | 1.3 ± 0.9 |
| | 2 | 3/3 | 13.8 ± 3.3 |
| D3 | 5[2] | 0/3 | |
| | 6[2] | 0/3 | |
| P3 | 11 | 3/3 | 5.7 ± 0.5 |
| | 14[3] | 3/3 | 2.1 ± 1.2 |
| P8 | 1[4] | 3/3 | 6.4 ± 5.3 |
| | 2 | 3/3 | 11.3 ± 3.9 |
| | 4[5] | 3/3 | 10.1 ± 4.8 |
| L3 (pp32) | 5[5] | 0/3 | |
| | 6[4] | 0/3 | |
| Vector Control | 2[3] | 0/3 | |
| | 3[1] | 0/3 | |

[1]FT1.7, clone 2 and Vector Control, clone 3 were tested on contralateral sides of a single group of animals.
[2]D3 clone 5 was tested on the contralateral sides of a group of animals simultaneously injected with NIH3T3 cells transfected with a clone of pp32r1 (data not shown). D3 clone 6 was tested on the contralateral sides of a group of animals simultaneously injected with a second clone of NIH3T3 cells transfected with pp32r1 (data not shown).
[3]P3, clone 14 and Vector Control, clone 2 were tested on contralateral sides of a single group of animals.
[4]P8, clone 1 and pp32, clone 6 were tested on contralateral sides of a single group of animals.
[5]P8, clone 4 and pp32, clone 5 were tested on contralateral sides of a single group of animals.
[6]One tumor in this group, weighing 0.5 gm, was detected only upon post mortem dissection.

What is claimed is:

1. An antibody that specifically binds to a polypeptide consisting of the sequence of pp32r1 (SEQ ID NO:4), but does not specifically bind to a polypeptide consisting of the sequence of pp32 (SEQ ID NO:5).

2. The antibody of claim 1, wherein the antibody is a monoclonal antibody.

* * * * *

UNITED STATES PATENT AND TRADEMARK OFFICE
CERTIFICATE OF CORRECTION

PATENT NO. : 6,930,175 B1
DATED : August 16, 2005
INVENTOR(S) : Gary R. Pasternack et al.

It is certified that error appears in the above-identified patent and that said Letters Patent is hereby corrected as shown below:

Title page,
Item [56], References Cited, OTHER PUBLICATIONS,
"C.M. Brennan et al." reference, change "Mma" to -- mRNA --;
"Ji-Chun Xue et al." reference, change "Idenitification" to -- Identification --;
"Walensky et al." reference, change "$M$" to -- $M_r$ --; and change "SelfRe-newal" to
-- self-renewal --;
"Ulitzur et al." reference, change "Protiens" to -- Proteins --; and change "o fBiological"
to -- of Biological --;
"Chen, et al." reference, change "Retinoblatoma" to -- Retinoblastoma --;
"Gomez-Marquez et al." reference, change "β Gene" to -- α Gene --;
"Morla, et al." reference, change "58:193" to -- 58:193-203 --;
"Durban, et al." reference, change "Phosphorylatoin" to -- Phosphorylation --;
"Matthews, et al." reference, change "Protien" to -- Protein --;
"Van Den Heuvel, et al." reference, change "Protiens" to -- Proteins --;
"Buttyan, R." reference, change "in Apoptosis, in Apoptosis:" to -- in Apopotsis: --;
"Hockenbery, et al." reference, change "Protien" to -- Protein --;
"Van Etten, et al." reference, change "-689" to -- 678 --;
"Aster, et al." reference, change "THe" to -- The --;
"Spiegal, et al." reference, change "Spiegal" to -- Spiegel --;
"Tang, et al." reference, change "1998" to -- 1988 --;
insert the following reference:
-- Weger, et al. 1992, "Morphometry and Prognosis in Cancer of the Pancreatic Head."
Pathol. Res. Pract., 188:764-769 Gustav Fischer Verlag, Stuttgart --;

Column 5,
Line 26, change "5,734.022" to -- 5,734,022 --;

Column 11,
Line 58, change "an" to -- art --;

Column 14,
Line 46, change "5.759,791" to -- 5,759,791 --;

Column 17,
Line 28, change "et at." to -- et al. --;

UNITED STATES PATENT AND TRADEMARK OFFICE
CERTIFICATE OF CORRECTION

PATENT NO. : 6,930,175 B1
DATED : August 16, 2005
INVENTOR(S) : Gary R. Pasternack et al.

It is certified that error appears in the above-identified patent and that said Letters Patent is hereby corrected as shown below:

<u>Column 24,</u>
Line 64, change "NIH31T3" to -- NIH3T3 --.

Signed and Sealed this

Twenty-fifth Day of April, 2006

JON W. DUDAS
*Director of the United States Patent and Trademark Office*

SEQUENCE LISTING

<160> NUMBER OF SEQ ID NOS: 55

<210> SEQ ID NO 1
<211> LENGTH: 5785
<212> TYPE: DNA
<213> ORGANISM: Homo sapiens

<400> SEQUENCE: 1

```
aagctttcct gatctctaaa tcaaggtcag ctccctaagc tcttggctcc cgtactgaaa    60
cttttttctta tgtaactctc ataaacacat agcataatgt tttgcatgtt tttcttccct   120
atcagttgca agttccagca gagctgatat attttcattt cattcgctac tatagcccta   180
gagcctgaca tagtttctgg ctgtgaatgc tcaataaata tttgtttaat tgagtagaaa   240
cataaagtat ctatttcatt gaaggaaaga ataattagct acattttct ttttcttgcc    300
ttaatatttg aggaatttgc ttatatgtca taataaaaaa gttaaagcct tatacattat   360
actaaggaat ttggacatta aattcaagct agccttttcta taaacaaaat actgaatttc   420
tgtccctaaa tttgttcctt ccctattctt ccccattgag atgacaccaa atccctctag   480
ctgctcaaac caagtacccg tatgttattc ttaattatct ctttaccttg cttctcatat   540
gcaatttgtt aacaagtcat cttcagtctg tatccattat tctcccttc cagaccacca    600
acatgtcttg actatactgc tacaatagcc tcccaactct tgtcctactt aaaattcatt   660
gtaaaaaatc agtcttggcc gggcacggtg gctcacacct ataatcccag cactttggga   720
gtcccaggcg ggcgggtcac gaggtcaaga gatggagacc atcatggcca acatggtgaa   780
accctgtctc tactataaat acaaaaaaat tatctgggtg tggtggcaca tgcctgtaat   840
cccaactact agggaggctg aggcaggaga atcgcttgaa cctgggaggc ggaggttgca   900
gtgagccgag atcgcaccat tgcactccag cctggcaaca gagcgagact ccatcccaaa   960
acaaaacaaa acaaaaccat gtaaaacatg tctgtaaaac atgtcagatt tcgtgttcag  1020
aagtcttaca tgtcttttca ttatgctaag ataaaaccca aatgcatttt cttggtttct  1080
aaagccaaga aaataagagt tgctttcagc aaccttgttt cttccgccat gcttttccct  1140
```

```
agctcactct ttttaggcaa gtcgacctga ttttctttct gttagtctgt ttctgcctcg    1200
tggtctggct ttctttctgt tagtctgttt ccacctcgtg gtcttggtcc tggctcttca    1260
ttctgcctgg aatgctctcc actccagatc cttactagat cttagctcag tcatcaccct    1320
cgcaggaaga tcttccaacc attcacctgc atacacctat ggctgctccc tagagaacat    1380
cattctgttt tcttcacttc ctagcactta ctgctttctg aaattatcta ctttgattgt    1440
ttatttcttt ctttactctt actaggatac ctgggtcatt aaaggaggga tatttctctc    1500
ttatttactg ttataaactt aatgcttagg ctgtagaagt tatacaatat ttgaagaata    1560
aatcgttaaa tgtataacat ttttgaagaa agataattgt gggatccatt tagtttgcaa    1620
acatttgatc tgtgtgttag acagaaggcc atggtaaagg acaaagacat attttatagg    1680
actgtaccct gaaaaataaa taaacttgaa ccagttatac aagacttatg tgcaggaaac    1740
aggtaccagt tatatttaga aatggtaaat caccttctaa gcataactca gagcacaata    1800
tattgagggg tagagagaga agtgcgtctt agatattggt aatcatatta ggactgacgc    1860
catccttgat ttttcttctg ggaaacagct caaaatgact attttaatgt tacaatgata    1920
tcttgcatct tgccagtaaa taatataata gacactagga atccaaattg taagatgaac    1980
aagtctttat agagggagag ccaaatacac aataaataac acaaggtggt aaatgcagta    2040
atacaaacat acataccatg cataggagtg cagagaaggt gtgcttctcc gaatgcagtc    2100
acccagaaag tccttctgta gaaagggata tcttaaatgg tgcttaaagg aaaagtaacc    2160
aaaggcaact aaagattgca aggaggtccc aggaaaaagc aaaagaacca aggtacata    2220 ggcacaaaag tagcctgcct tcctgggaac ttccaatagt ttgctggagc acacagttag    2280
aagtactgtg ccatgggagc aaagactgaa gacatatgca ggttcaaggg cacagagccc    2340
catatatgtc atgataagat attgggaagc cactggggag ctactgaaac tttaagcagg    2400
gaaataaaat tgtcatatct acaccttaga aatttgattt ttttctcttc ttttatcttc    2460
tcttctcctc tcttctctct ctctctctct gtgtgtgtgt gtgtgtgtgt                2520
gtgtgtgtgt gacagagtcc tgctctgtca cccaggctgg agtgtagtgg agtgatctcc    2580
gcttactgca gtctctgcct ctcaagcgat tccctgcctc agcctcccga gtagctggga    2640
ttacaggcgg gctctacaac agctggctaa cttttgtatt ttttggtaac aaccaggttt    2700
taccatgttg gccaggctgg tcttgaactc ctgacctcag gtgatctgcc tgccttggct    2760
ttccaaagtg ctgggattac aggcgtgagc caccctgcct ggtgtagaag tttgattttg    2820
atgtcagtgt ggtagatgaa tttgtgggaa gcaaacaag atagagttca atgacagtga    2880
aaagtttatt gtataagcta tataaagaa atgttgaag gtttgaaatc cattagtggc    2940
agtaagggtg tacagaacga aactatttga gaagtacaca aggcaagtct tactttcaag    3000
gcagtttatg taagctcatt caattgtctc agtgttcttg ctatgtgtgg gttataggat    3060
ttggaacata tgatcaatct gagcacacat cagtaaactg aataggatta ttaaaatcca    3120
caagcatttt actagtggaa tctgtgtatat tttctagcta ctcttgcttg ttttatttga    3180
atcttttgct catatcctat agtaaagatt tcaggaaata tattttatt tgcctagaat    3240 tttagccttt tagttttttg aatctattgc tcatattctt atagtaagag tttcagggaa    3300
tgtatttcta tttgtctgga attttagcct ttcaggtttt tgagcccctc ttttgcttat    3360
gggacatagt atgagacaag atgaaatgat acttctattc ccaattcact gatgggaaa    3420 atgaagcaaa aaatgttatt cactcaaggc ttctgccatg tttcctggtg gaattacggc    3480
```

-continued

```
tcagacacaa atttcctaat gcctgtgctg ctaacttctc aatagaacac tatattaatt    3540
tatcttcttc ctgagtgttt ttccacaaat cccatagcct gtgaaaagat tgttttaggg    3600
aaatattatt tttaatatag catattttgt caatgtggga cataggacta gtacctgctg    3660
aaaaccatct catgatcctt gtgtaagaac taattcacac tagaaatact attttccttg    3720
ctcattaaaa acataaatgt ctcagaaagt aaaaaattat tcctctctaa ataaacatac    3780
atgccactca aattttattc ctctaccact tgccgtatct aaacctagtt agatactttg    3840
gttttaggta taatctgaca gaacagatac aaccaagatc acattgtgag tcagaagtgg    3900
aaaattcata attcatgatg ataccaataa agatagatt tagcttttta caggatgttt    3960
ttggcatttt attctttcat ttgaggggag atctcaccaa aatatgtctt tcatggttca    4020
ttgtgttatt taatttctgt gatgcatatt ctcaggttac tttaaaccta gtctatagat    4080
tcaaagatat cccgtgtcag gtctctaaaa gtaaaagaa aaatgggtac ttgtgaaggc    4140
tgattcacag taagtagtgt agaggggagt gccttgtgta ttcacaaatt atcaacgtga    4200
gcatcagata agattttctt tagtcacaca cacctacctt cttactagga agatccatat    4260
acttgaataa ttgttctgct tgacccaggt tacttatcag tccctttatt ataatatttg    4320
taaatattgg ggctcgagaa ccgagcggag ctggttgagt cttcaaagtc ctaaaacgtg    4380
cggccgtggg ttcgaggttt attgattgaa ttcggctggc acgagagcct ctgcagacag    4440
agagcgcgag agatggagat gggcagacgg attcattcag agctgcggaa cagggcgccc    4500
tctgatgtga aagaacttgc cctggacaac agtcggtcga atgaaggcaa actcgaagcc    4560
ctcacagatg aatttgaaga actggaattc ttaagtaaaa tcaacggagg cctcacctca    4620
atctcagact taccaaagtt aaagttgaga aagcttgaac taagagtctc aggggggcctg    4680 gaagtattgg cagaaaagtg tccaaacctc acgcatctat atttaagtgg caacaaaatt    4740
aaagacctca gcacaataga gccactgaaa cagttagaaa acctcaagag cttagacctt    4800
ttcaattgcg aggtaaccaa cctgaacgac tacggagaaa acgtgttcaa gcttctcctg    4860
caactcacat atctcgacag ctgttactgg gaccacaagg aggcccctta ctcagatatt    4920
gaggaccacg tggagggcct ggatgacgag gaggagggtg agcatgagga ggagtatgat    4980
gaagatgctc agtagtgga agatgaggag ggcgaggagg aggaggagga aggtgaagag    5040
gaggacgtga gtggagggga cgaggaggat gaagaaggtt ataacgatgg agaggtagat    5100
ggcgaggaag atgaagaaga gcttggtgaa gaagaaaggg gtcagaagcg aaaatgagaa    5160
cctgaagatg agggagaaga tgatgactaa gtagaataac ctattttgaa aaattcctat    5220
tgtgatttga ctgtttttac ccatatcccc tcccccctcc aatcctgccc cctgaaactt    5280 actttttct gattgtaaca ttgctgtggg aatgagacgg gaaagtgta ctgggggttg    5340 tggagggagg gagggcagga ggcggtggac taaaatacta tttttactgc caaataaaat    5400
aatatttgta aatattaact gggatactag ctttgtagaa tgattactat taattattct    5460
ctctctcttt ttattttttt acacattcta ttcttttaag tatagtcctt ttagtccaag    5520
gaaaaggcac tacaatccac ttattaatgc ttgctactgt gttcaagtaa aataagctcc    5580
aggatttaac aaaaagagga aagaaaatat ttacaatgaa aatgttgcta aaaatttaaa    5640
acaaattaca gtaaatgtat tgttaaagca aattctattt ttaaaattta ttaataagga    5700
aataatttgc taaagcaaat ttttggaaaa ataataatgc actttatact tgattttatt    5760
tattaaaaca atgatttata agctt                                         5785
```

<210> SEQ ID NO 2
<211> LENGTH: 1035
<212> TYPE: DNA
<213> ORGANISM: homo sapiens

<400> SEQUENCE: 2

| | |
|---|---:|
| gagtcttcaa agtcctaaaa cgtgcggccg tgggttcgag gtttattgat tgaattcggc | 60 |
| tggcacgaga gcctctgcag acagagagcg cgagagatgg agatgggcag acggattcat | 120 |
| tcagagctgc ggaacagggc gccctctgat gtgaaagaac ttgccctgga caacagtcgg | 180 |
| tcgaatgaag gcaaactcga agccctcaca gatgaatttg aagaactgga attcttaagt | 240 |
| aaaatcaacg gaggcctcac ctcaatctca gacttaccaa agttaaagtt gagaaagctt | 300 |
| gaactaagag tctcaggggg cctggaagta ttggcagaaa agtgtccaaa cctcacgcat | 360 |
| ctatatttaa gtggcaacaa aattaaagac ctcagcacaa tagagccact gaaacagtta | 420 |
| gaaaacctca agagcttaga ccttttcaat tgcgaggtaa ccaacctgaa cgactacgga | 480 |
| gaaaacgtgt tcaagcttct cctgcaactc acatatctcg acagctgtta ctgggaccac | 540 |
| aaggaggccc cttactcaga tattgaggac cacgtggagg gcctggatga cgaggaggag | 600 |
| ggtgagcatg aggaggagta tgatgaagat gctcaggtag tggaagatga ggagggcgag | 660 |
| gaggaggagg aggaaggtga agaggaggac gtgagtggag gggacgagga ggatgaagaa | 720 |
| ggttataacg atggagaggt agatggcgag gaagatgaag aagagcttgg tgaagaagaa | 780 |
| aggggtcaga agcgaaaatg agaacctgaa gatgagggag aagatgatga ctaagtagaa | 840 |
| taacctattt tgaaaaattc ctattgtgat ttgactgttt ttacccatat cccctccccc | 900 |
| ctccaatcct gcccctgaa acttacttt ttctgattgt aacattgctg tgggaatgag | 960 |
| acgggaaaag tgtactgggg gttgtggagg gagggagggc aggaggcggt ggactaaaat | 1020 |
| actatttta ctgcc | 1035 |

<210> SEQ ID NO 3
<211> LENGTH: 1052
<212> TYPE: DNA
<213> ORGANISM: Homo sapiens

<400> SEQUENCE: 3

| | |
|---|---:|
| gaattcccaa agtcctaaaa cgcgcggccg tgggttcggg gtttattgat tgaattccgc | 60 |
| cggcgcggga gcctctgcag agagagagcg cgagagatgg agatgggcag acggattcat | 120 |
| ttagagctgc ggaacaggac gccctctgat gtgaaagaac ttgtcctgga caacagtcgg | 180 |
| tcgaatgaag gcaaactcga aggcctcaca gatgaatttg aagaactgga attcttaagt | 240 |
| acaatcaacg taggcctcac ctcaatcgca aacttaccaa agttaaacaa acttaagaag | 300 |
| cttgaactaa gcgataacag agtctcaggg ggcctagaag tattggcaga aaagtgtccg | 360 |
| aacctcacgc atctaaattt aagtggcaac aaaattaaag acctcagcac aatagagcca | 420 |
| ctgaaaaagt tagaaaacct caagagctta gaccttttca attgcgaggt aaccaacctg | 480 |
| aacgactacc gagaaaatgt gttcaagctc ctcccgcaac tcacatatct cgacggctat | 540 |
| gaccgggacg acaaggaggc ccctgactcg gatgctgagg gctacgtgga gggcctggat | 600 |
| gatgaggagg aggatgagga tgaggaggag tatgatgaag atgctcaggt agtggaagac | 660 |
| gaggaggacg aggatgagga ggaggaaggt gaagaggagg acgtgagtgg agaggaggag | 720 |
| gaggatgaag aaggttataa cgatggagag gtagatgacg aggaagatga agaagagctt | 780 |
| ggtgaagaag aaagggggtca gaagcgaaaa cgagaacctg aagatgaggg agaagatgat | 840 |

-continued

```
gactaagtgg aataacctat tttgaaaaat tcctattgtg atttgactgt ttttacccat    900 atccctctc ccccccccct ctaatcctgc cccctgaaac ttattttttt ctgattgtaa    960
cgttgctgtg ggaacgagag gggaagagtg tactgggggt tgcgggggga ggatggcggg   1020 tggggtgga ataaaatact attttttactg cc                                 1052
```

<210> SEQ ID NO 4
<211> LENGTH: 234
<212> TYPE: PRT
<213> ORGANISM: Homo sapiens

<400> SEQUENCE: 4

| Met | Glu | Met | Gly | Arg | Arg | Ile | His | Ser | Glu | Leu | Arg | Asn | Arg | Ala | Pro |
|---|---|---|---|---|---|---|---|---|---|---|---|---|---|---|---|
| 1 | | | | 5 | | | | | 10 | | | | | 15 | |

| Ser | Asp | Val | Lys | Glu | Leu | Ala | Leu | Asp | Asn | Ser | Arg | Ser | Asn | Glu | Gly |
|---|---|---|---|---|---|---|---|---|---|---|---|---|---|---|---|
| | | | 20 | | | | | 25 | | | | | 30 | | |

| Lys | Leu | Glu | Ala | Leu | Thr | Asp | Glu | Phe | Glu | Glu | Leu | Glu | Phe | Leu | Ser |
|---|---|---|---|---|---|---|---|---|---|---|---|---|---|---|---|
| | | | 35 | | | | | 40 | | | | | 45 | | |

| Lys | Ile | Asn | Gly | Gly | Leu | Thr | Ser | Ile | Ser | Asp | Leu | Pro | Lys | Leu | Lys |
|---|---|---|---|---|---|---|---|---|---|---|---|---|---|---|---|
| | 50 | | | | | 55 | | | | | 60 | | | | |

| Leu | Arg | Lys | Leu | Glu | Leu | Arg | Val | Ser | Gly | Leu | Glu | Val | Leu | Ala |
|---|---|---|---|---|---|---|---|---|---|---|---|---|---|---|
| 65 | | | | 70 | | | | | 75 | | | | | 80 |

| Glu | Lys | Cys | Pro | Asn | Leu | Thr | His | Leu | Tyr | Leu | Ser | Gly | Asn | Lys | Ile |
|---|---|---|---|---|---|---|---|---|---|---|---|---|---|---|---|
| | | | | 85 | | | | | 90 | | | | | 95 | |

| Lys | Asp | Leu | Ser | Thr | Ile | Glu | Pro | Leu | Lys | Gln | Leu | Glu | Asn | Leu | Lys |
|---|---|---|---|---|---|---|---|---|---|---|---|---|---|---|---|
| | | | | 100 | | | | | 105 | | | | | 110 | |

| Ser | Leu | Asp | Leu | Phe | Asn | Cys | Glu | Val | Thr | Asn | Leu | Asn | Asp | Tyr | Gly |
|---|---|---|---|---|---|---|---|---|---|---|---|---|---|---|---|
| | | | 115 | | | | | 120 | | | | | 125 | | |

| Glu | Asn | Val | Phe | Lys | Leu | Leu | Leu | Gln | Leu | Thr | Tyr | Leu | Asp | Ser | Cys |
|---|---|---|---|---|---|---|---|---|---|---|---|---|---|---|---|
| | 130 | | | | | 135 | | | | | 140 | | | | |

| Tyr | Trp | Asp | His | Lys | Glu | Ala | Pro | Tyr | Ser | Asp | Ile | Glu | Asp | His | Val |
|---|---|---|---|---|---|---|---|---|---|---|---|---|---|---|---|
| 145 | | | | | 150 | | | | | 155 | | | | | 160 |

| Glu | Gly | Leu | Asp | Asp | Glu | Glu | Glu | Gly | Glu | His | Glu | Glu | Glu | Tyr | Asp |
|---|---|---|---|---|---|---|---|---|---|---|---|---|---|---|---|
| | | | | 165 | | | | | 170 | | | | | 175 | |

| Glu | Asp | Ala | Gln | Val | Val | Glu | Asp | Glu | Glu | Gly | Glu | Glu | Glu | Glu | Glu |
|---|---|---|---|---|---|---|---|---|---|---|---|---|---|---|---|
| | | | 180 | | | | | 185 | | | | | 190 | | |

| Glu | Gly | Glu | Glu | Glu | Asp | Val | Ser | Gly | Gly | Asp | Glu | Glu | Asp | Glu | Glu |
|---|---|---|---|---|---|---|---|---|---|---|---|---|---|---|---|
| | | | 195 | | | | | 200 | | | | | 205 | | |

| Gly | Tyr | Asn | Asp | Gly | Glu | Val | Asp | Gly | Glu | Glu | Asp | Glu | Glu | Glu | Leu |
|---|---|---|---|---|---|---|---|---|---|---|---|---|---|---|---|
| | 210 | | | | | 215 | | | | | 220 | | | | |

| Gly | Glu | Glu | Glu | Arg | Gly | Gln | Lys | Arg | Lys |
|---|---|---|---|---|---|---|---|---|---|
| 225 | | | | | 230 | | | | |

<210> SEQ ID NO 5
<211> LENGTH: 249
<212> TYPE: PRT
<213> ORGANISM: Homo sapiens

<400> SEQUENCE: 5

| Met | Glu | Met | Gly | Arg | Arg | Ile | His | Leu | Glu | Leu | Arg | Asn | Arg | Thr | Pro |
|---|---|---|---|---|---|---|---|---|---|---|---|---|---|---|---|
| 1 | | | | 5 | | | | | 10 | | | | | 15 | |

| Ser | Asp | Val | Lys | Glu | Leu | Val | Leu | Asp | Asn | Ser | Arg | Ser | Asn | Glu | Gly |
|---|---|---|---|---|---|---|---|---|---|---|---|---|---|---|---|
| | | | 20 | | | | | 25 | | | | | 30 | | |

| Lys | Leu | Glu | Gly | Leu | Thr | Asp | Glu | Phe | Glu | Glu | Leu | Glu | Phe | Leu | Ser |
|---|---|---|---|---|---|---|---|---|---|---|---|---|---|---|---|
| | | | 35 | | | | | 40 | | | | | 45 | | |

| Thr | Ile | Asn | Val | Gly | Leu | Thr | Ser | Ile | Ala | Asn | Leu | Pro | Lys | Leu | Asn |
|---|---|---|---|---|---|---|---|---|---|---|---|---|---|---|---|

```
                50                      55                      60
Lys Leu Lys Lys Leu Glu Leu Ser Asp Asn Arg Val Ser Gly Gly Leu
 65                      70                      75                      80

Glu Val Leu Ala Glu Lys Cys Pro Asn Leu Thr His Leu Asn Leu Ser
                     85                      90                      95

Gly Asn Lys Ile Lys Asp Leu Ser Thr Ile Glu Pro Leu Lys Lys Leu
                100                     105                     110

Glu Asn Leu Lys Ser Leu Asp Leu Phe Asn Cys Glu Val Thr Asn Leu
            115                     120                     125

Asn Asp Tyr Arg Glu Asn Val Phe Lys Leu Leu Pro Gln Leu Thr Tyr
130                     135                     140

Leu Asp Gly Tyr Asp Arg Asp Asp Lys Glu Ala Pro Asp Ser Asp Ala
145                     150                     155                     160

Glu Gly Tyr Val Glu Gly Leu Asp Asp Glu Glu Asp Glu Asp Glu
                165                     170                     175

Glu Glu Tyr Asp Glu Asp Ala Gln Val Val Glu Asp Glu Glu Asp Glu
            180                     185                     190

Asp Glu Glu Glu Glu Gly Glu Glu Asp Val Ser Gly Glu Glu Glu
            195                     200                     205

Glu Asp Glu Glu Gly Tyr Asn Asp Gly Glu Val Asp Asp Glu Asp
            210                     215                     220

Glu Glu Glu Leu Gly Glu Glu Glu Arg Gly Gln Lys Arg Lys Arg Glu
225                     230                     235                     240

Pro Glu Asp Glu Gly Glu Asp Asp
                245
```

<210> SEQ ID NO 6
<211> LENGTH: 889
<212> TYPE: DNA
<213> ORGANISM: Homo sapiens

<400> SEQUENCE: 6

```
gggttcgagg tttattgatt gaattcggct ggcacgagag cctctgcaga cagagagcgc      60
gagagatgga gatgggcaga cggattcatt cagagctgcg aacagggcg ccctctgatg     120
tgaaagaact tgccctggac aacagtcggt cgaatgaagg caaactcgaa gccctcacag     180
atgaatttga agaactggaa ttcttaagta aaatcaacgg aggcctcacc tcaatctcag     240
acttaccaaa gttaaagttg agaaagcttg aactaagagt ctcagggggc ctggaagtat     300
tggcagaaaa gtgtccaaac ctcacgcatc tatatttaag tggcaacaaa attaaagacc     360
tcagcacaat agagccactg aaacagttag aaaacctcaa gagcttagac cttttcaatt     420
gcgaggtaac caacctgaac gactacgag aaaacgtgtt caagcttctc ctgcaactca     480
catatctcga cagctgttac tgggaccaca aggaggcccc ttactcagat attgaggacc     540
acgtggaggg cctggatgac gaggaggagg gtgagcatga ggaggagtat gatgaagatg     600
ctcaggtagt ggaagatgag gagggcgagg aggaggagga ggaaggtgaa gaggaggacg     660
tgagtggagg ggacgaggag gatgaagaag gttataacga tggagaggta gatgcgagg     720
aagatgaaga agagcttggt gaagaagaaa ggggtcagaa gcgaaaatga gaacctgaag     780
atgagggaga agatgatgac taagtagaat aacctatttt gaaaaattcc tattgtgatt     840
tgactgtttt tacccatatc ccctccccc tccaatcctg ccccctgaa                  889
```

<210> SEQ ID NO 7
<211> LENGTH: 906

```
<212> TYPE: DNA
<213> ORGANISM: Homo sapiens

<400> SEQUENCE: 7
gggttcgggg tttattgatt gaattccgct ggcgcgggag cctctgcaga gagagagcgc      60
gagagatgga gatgggcaga cggattcatt tagagctgcg gaacaggacg ccctctgatg     120
tgaaagaact tgtcctggac aacagtcggt cgaatgaagg caaactcgaa ggcctcacag     180
atgaatttga agaactggaa ttcttaagta caatcaacgt aggcctcacc tcaatcgcaa     240
acttaccaaa gttaaacaaa cttaagaagc ttgaactaag cagtaacaga gtctcagggg     300
gcctagaagt attggcagaa aagtgtccaa acctcacgca tctaaattta agtggcaaca     360
aaattaaaga cctcagcaca atagagccac tgaaaaagtt agaaaacctc aagagcttag     420
accttttcaa ttgcgaggta accaacctga acgactaccg agaaaatgtg ttcaagctcc     480
tcctgcaact cacatatctc gacggctgtg accgggacga caaggaggcc cctgactcgg     540
atgctgaggg ctacgtggag ggcctggatg acgaggagga ggatgaggat gaggaggagt     600
atgatgaaga tgctcaggta gtggaagatg aggaggacga ggatgaggag gaggaaggtg     660
aagaggagga cgtgagtgga gaggaggagg aggatgaaga aggttataac gatggagagg     720
tagatgacga ggaagatgaa gaagagcttg gtgaagaaga aagggggtcag aagcgaaaag     780
agaacctgaa gatgagggag aagatgatga ctaagtggaa taacctatttt tgaaaaattc     840
ctattgtgat ttgactgttt ttacccatat cccctctccc cccccctct aatcctgccc     900
cctgaa                                                                906

<210> SEQ ID NO 8
<211> LENGTH: 907
<212> TYPE: DNA
<213> ORGANISM: homo sapiens

<400> SEQUENCE: 8
gggttcgggg tttattgatt gaattccgcc ggcgcgggag cctctgcaga gagagagcgc      60
gagagatgga gatgggcaga cggattcatt tagagctgcg gaacaggacg ccctctgatg     120
tgaaagaact tgtcctggac aacagtcggt cgaatgaagg caaactcgaa ggcctcacag     180
atgaatttga agaactggaa ttcttaagta caatcaacgt aggcctcacc tcaatcgcaa     240
acttaccaaa gttaaacaaa cttaagaagc ttgaactaag cgataacaga gtctcagggg     300
gcctagaagt attggcagaa aagtgtccga acctcacgca tctaaattta agtggcaaca     360
aaattaaaga cctcagcaca atagagccac tgaaaaagtt agaaaacctc aagagcttag     420
accttttcaa ttgcgaggta accaacctga acgactaccg agaaaatgtg ttcaagctcc     480
tcccgcaact cacatatctc gacggctatg accgggacga caaggaggcc cctgactcgg     540
atgctgaggg ctacgtggag ggcctggatg atgaggagga ggatgaggat gaggaggagt     600
atgatgaaga tgctcaggta gtggaagacg aggaggacga ggatgaggag gaggaaggtg     660
aagaggagga cgtgagtgga gaggaggagg aggatgaaga aggttataac gatggagagg     720
tagatgacga ggaagatgaa gaagagcttg gtgaagaaga aagggggtcag aagcgaaaac     780
gagaacctga agatgaggga agatgatga actaagtgga ataacctatt tgaaaaaatt     840
cctattgtga tttgactgtt tttacccata tcccctctcc cccccccctc taatcctgcc     900
ccctgaa                                                               907

<210> SEQ ID NO 9
```

<211> LENGTH: 907
<212> TYPE: DNA
<213> ORGANISM: Homo sapiens

<400> SEQUENCE: 9

```
gggttcgagg tttattgatt gaattcggct ggcacgagag cctctgcaga cagagagcgc      60
gagagatgga gatgggcaga cggattcatt cagagctgcg gaacagggcg ccctctgatg     120
tgaaagaact tgccctggac aacagtcggt cgaatgaagg caaactcgaa gccctcacag     180
atgaatttga agaactggaa ttcttaagta aaatcaacgg aggcctcacc tcaatctcag     240
acttaccaaa gttaaacaag ttgagaaagc ttgaactaag cagtaacaga gtctcagggg     300
gcctggaagt attggcagaa aagtgtccaa acctcacgca tctatattta agtggcaaca     360
aaattaaaga cctcagcaca atagagccac tgaaacagtt agaaaacctc aagagcttag     420
accttttcaa ttgcgaggta accaacctga cgactacgg agaaaacgtg ttcaagcttc      480
tcctgcaact cacatatctc gacagctgtt actgggacca aaggaggcc cttactcag      540
atattgagga ccacgtggag ggcctggatg acgaggagga gggtgagcat gaggaggagt     600
atgatgaaga tgctcaggta gtggaagatg aggagggcga ggaggaggag gaggaaggtg     660
aagaggagga cgtgagtgga ggggacgagg aggatgaaga aggttataac gatggagagg     720
tagatggcga ggaagatgaa gaagagcttg gtgaagaaga aaggggtcag aagcgaaaat     780
gagaacctga agatgaggga gaagatgatg actaagtaga ataacctatt tgaaaaatt     840
cctattgtga tttgactgtt tttacccata tcccctctcc ccccccctc caatcctgcc     900
ccctgaa                                                              907
```

<210> SEQ ID NO 10
<211> LENGTH: 907
<212> TYPE: DNA
<213> ORGANISM: Homo sapiens

<400> SEQUENCE: 10

```
gggttcgggg tttattgatt gaattcggct ggcgcgggag cctctgcaga gagagagcgc      60
gagagatgga gatgggcaga cggattcatt tagagctgcg gaacgggacg ccctctgatg     120
tgaaagaact tgtcctggac aacagtcggt cgaatgaagg caaactcgaa ggcctcacag     180
atgaatttga agaactggaa ttcttaagta caatcaacgt aggcctcacc tcaatcgcaa     240
acttaccaaa gttaaacaaa cttaagaagc ttgaactaag cagtaacaga gcctcagtgg     300
gcctagaagt attggcagaa aagtgtccaa acctcataca tctaaattta agtggcaaca     360
aaattaaaga cctcagcaca atagagcccc tgaaaaagtt agaaaacctc gagagcttag     420
accttttcac ttgcgaggta accaacctga caaactactg agaagatg ttcaagctcc        480
tcctgcaact cacatatctc aacggctgtg accggatga caaggaggcc cctaactcgg      540
atggtgaggg ctttgtggag tgcctggatg acaaggagga ggatgaggat gaggaggagt     600
atgatgaaga tgctcaggta atggaagatg aggaggacga ggatgaggag gaggaacgtg     660
aagaggagga cgtgagtgga gacgaggagg agaaggatga aggttataac aatgagagg      720
tagatgatga ggaagatgaa gaagagcttg gtgaagaaga aggggtcag aagcgaaaat     780
aagaaactga agatgaggga gaagacgatg cctaagtgga ataatctatt tgaaaaatt     840
cctttgtga ttttactgtt tttagccgta ccccctctcc cccccactc taatcctgcc     900
ccctgaa                                                              907
```

```
<210> SEQ ID NO 11
<211> LENGTH: 907
<212> TYPE: DNA
<213> ORGANISM: Homo sapiens

<400> SEQUENCE: 11
gggttcgggg tttattgatt gaattcggct ggcacgagag cctctgcaga cagagagcgc      60
gagagacgga gatgggcaga cggattcatt cagagctgcg gaacagggcg ccctctgatg     120
tgaaagaact tgccctggac aacagtcggt cgaatgaagg caaactcgaa gccctcacag     180
atgaatttga agaactggaa ttcttaagta aaatcaacgg aggcctcacc tcaatctcag     240
acttaccaaa gttaaacaag ttgagaaagc ttgaactaag cagtaacaga gtctcagggg     300
gcctggaagt attggcagaa aagtgtccaa acctcacgca tctatattta agtggcaaca     360
aaattaaaga cctcagcaca atagagccac tgaaacagtt agaaaacctc aagagcttag     420
acctttttcaa ttgcgaggta accaacctga acgactacgg agaaaacgtg ttcaagcttc     480
tcctgcaact cacatatctc gacagctgtt actgggacca caaggaggcc ccttactcag     540
atattgaggc ccacgtggag ggcctggatg acgaggagga gggtgagcat gaggaggagt     600
atgatgaaga tgctcaggta gtggaagatg aggagggcga ggaggaggag gaggaaggtg     660
aagaggagga cgtgagtgga ggggacgagg aggatgaaga aggttataac gatggagagg     720
tagatggcga ggaagatgaa gaagagcttg gtgaagaaga aaggggtcag aagcgaaaat     780
gagaacctga agatgaggga gaagatgatg actaagtaga ataacctatt ttgaaaaatt     840
cctattgtga tttgactgtt tttacccata tcccctctcc cccccccctc taatcctgcc     900
ccctgaa                                                              907

<210> SEQ ID NO 12
<211> LENGTH: 907
<212> TYPE: DNA
<213> ORGANISM: Homo sapiens

<400> SEQUENCE: 12
gggttcgggg tttattggtt gaattccgct ggctcaggag cctctgcaga gagaaagcgt      60
gagagatgga gatgggcaaa tggattcatt tagagctgcg gaacaggacg ccctccgatg     120
tgaaagaact tttcctggac aacagtcagt caaatgaagg caaattggaa ggcctcacag     180
atgaatttga agaactggaa ttattaaata caatcaacat aggcctcacc tcaattgcaa     240
acttgccaaa gttaaacaaa cttaagaagc ttgaactaag cagtaacaga gcctcagtgg     300
gcctagaagt attggcagaa aagtgtccaa acctcataca tctaaattta agtggcaaca     360
aaattaaaga cctcagcaca atagagcccc tgaaaaagtt agaaaacctc gagagcttag     420
acctttttcac ttgcgaggta accaacctga caactactg agaaagatg ttcaagctcc     480
tcctgcaact cacatatctc aacggctgtg acccggatga caaggaggcc cctaactcgg     540
atggtgaggg ctttgtggag tgcctggatg acaaggagga ggatgaggat gaggaggagt     600
atgatgaaga tgctcaggta atggaagatg aggaggacga ggatgaggag gaggaacgtg     660
aagaggagga cgtgagtgga gacgaggagg agaaggatga aggttataac aatggagagg     720
tagatgatga ggaagatgaa gaagagcttg gtgaagaaga aagggqtcag aagcgaaaat     780
aagaaactga agatgaggga gaagacgatg cctaagtgga ataatctatt ttgaaaaatt     840
ccttttgtga ttttactgtt tttagccgta tccctctcc ccccccactc taatcctgcc     900
ccctgaa                                                              907
```

<210> SEQ ID NO 13
<211> LENGTH: 907
<212> TYPE: DNA
<213> ORGANISM: Homo sapiens

<400> SEQUENCE: 13

| | | | | | |
|---|---|---|---|---|---|
| gggttcgggg | tttattgatt | gaattccgcc | ggcgcgggag | cctctgcaga | gagagagcgc | 60 |
| gagagatgga | gatgggcaga | cggattcatt | tagagctgcg | gaacaggacg | ccctctgatg | 120 |
| tgaaagaact | tgtcctggac | aacagtcggt | cgaatgaagg | caaactcgaa | ggcctcacag | 180 |
| atgaatttga | agaactggaa | ttcttaagta | caatcaacgt | aggcctcacc | tcaatcgcaa | 240 |
| acttgccaaa | gttaaacaaa | cttaagaagc | ttgaactaag | cagtaacaga | gcctcagtgg | 300 |
| gcctagaagt | attggcagaa | aagtgtccaa | acctcataca | tctaaattta | agtggcaaca | 360 |
| aaattaaaga | cctcagcaca | atagagccac | tgaaaaagtt | agaaaacctc | aagagcttag | 420 |
| acctttccaa | ttgcgaggta | accaacctga | acgactaccg | agaaaatgtg | ttcaagctcc | 480 |
| tcccgcaact | cacatatctc | gacggctatg | accgggacga | caaggaggcc | cctgactcgg | 540 |
| atgctgaggg | ctacgtggag | ggcctggatg | atgaggagga | ggatgaggat | gaggaggagt | 600 |
| atgatgaaga | tgctcaggta | gtagaagacg | aggaggacga | ggatgaggag | gaggaaggtg | 660 |
| aagaggagga | cgtgagtgga | gaggaggagg | aggatgaaga | aggttataac | gatggagagg | 720 |
| tagatgacga | ggaagatgaa | gaagagcttg | gtgaagaaga | aaggggtcag | aagcgaaaac | 780 |
| gagaacctga | agatgaggga | gaagatgatg | actaagtgga | ataacctatt | ttgaaaaatt | 840 |
| cctattgtga | tttgactgtt | tttacccata | tcccctctcc | ccccccctc | taatcctgcc | 900 |
| ccctgaa | | | | | | 907 |

<210> SEQ ID NO 14
<211> LENGTH: 908
<212> TYPE: DNA
<213> ORGANISM: Homo sapiens

<400> SEQUENCE: 14

| | | | | | |
|---|---|---|---|---|---|
| gggttcgggg | tttattggtt | gaattccgct | ggctcaggag | cctctgcaga | gaaagcgcgc | 60 |
| tgagagatgg | agatgggcaa | atggattcat | ttagagctgc | ggaacaggac | gccctccgat | 120 |
| gtgaaagaac | ttttcctgga | caacagtcag | tcaaatgaag | gcaaattgga | aggcctcaca | 180 |
| gatgaatttg | aagaactgga | attattaaat | acaatcaaca | taggcctcac | ctcaattgca | 240 |
| aacttgccaa | agttaaacaa | acttaagaag | cttgaactaa | gcagtaacag | agcctcagtg | 300 |
| ggcctagaag | tattggcaga | aaagtgtcca | aacctcatac | atctaaattt | aagtggcaac | 360 |
| aaaattaaag | acctcagcac | aatagagccc | tgaaaaagt | tagaaaacct | cgagagctta | 420 |
| gacctttca | cttgcgaggt | aaccaacctg | aacaactacc | gagaaaatgt | gttcaagctc | 480 |
| ctcccgcaac | tcacatatct | cgacggctat | gaccgggaca | caaggaggc | ccctgactcg | 540 |
| gatgctgagg | gctacgtgga | gggcctggat | gatgaggagg | aggatgagga | tgaggaggag | 600 |
| tatgatgaag | atgctcaggt | agtggaagac | gaggaggacg | aggatgagga | ggaggaaggt | 660 |
| gaagaggagg | acgtgagtgg | agaggaggag | gaggatgaag | aaggttataa | cgatggagag | 720 |
| gtagatgacg | aggaagatga | agaagagctt | ggtgaagaag | aaaggggtca | gaagcgaaaa | 780 |
| cgagaacctg | aagatgaggg | agaagatgat | gactaagtgg | aataacctat | tttgaaaaat | 840 |
| tcctattgtg | atttgactgt | ttttacccat | atcccctctc | ccccccccct | ctaatcctgc | 900 |
| ccctgaa | | | | | | 908 |

<210> SEQ ID NO 15
<211> LENGTH: 907
<212> TYPE: DNA
<213> ORGANISM: Homo sapiens

<400> SEQUENCE: 15

```
gggttcgggg tttattgatt gaattccgcc ggcgcgggag cctctgcaga gagagagcgc      60
gagagatgga gatgggcaga cggattcatt tagagctgcg gaacaggacg ccctctgatg     120
tgaaagaact tgtcctggac aacagtcggt cgaatgaagg caaactcgaa ggcctcacag     180
atgaatttga agaactggaa ttcttaagta caatcaacgt aggcctcacc tcaatcgcaa     240
acttaccaaa gttaaacaaa cttaagaagc ttgaactaag cgataacaga gtctcagggg     300
gcctggaagt attggcagaa aagtgtccga acctcacgca tctaaattta agtggcaaca     360
aaattaaaga cctcagcaca atagagccac tgaaaaagtt agaaaacctc aagagcttag     420
acctttttcaa ttgcgaggta accaacctga acgactaccg agaaaatgtg ttcaagctcc     480
tcccgcaact cacatatctc gacggctatg accgggacga caaggaggcc cctgactcgg     540
atgctgaggg ctacgtggag ggcctggatg atgaggagga ggatgaggat gaggaggagt     600
atgatgaaga tgctcaggta gtggaagacg aggaggacga ggatgaggag gaggaaggtg     660
aagaggagga cgtgagtgga gaggaggagg aggatgaaga aggttataac gatggagagg     720
tagatgacga ggaagatgaa gaagagcttg gtgaagaaga aagggtcag aagcgaaaac     780
gagaacctga agatgaggga gaagatgatg actaagtgga ataacctatt ttgaaaaatt     840
cctattgtga tttgactgtt tttacccata tccctctcc ccccccctc taatcctgcc     900
ccctgaa                                                                907
```

<210> SEQ ID NO 16
<211> LENGTH: 907
<212> TYPE: DNA
<213> ORGANISM: Homo sapiens

<400> SEQUENCE: 16

```
gggttcgggg tttattgatt gaattcggct ggcacgagag cctctgcaga cagagagcgc      60
gagagatgga gatgggcaga cggattcatt cagagctgcg gaacagggcg ccctctgatg     120
tgaaagaact tgccctggac aacagtcggt cgaatgaagg caaactcgaa gccctcacag     180
atgaatttga agaactggaa ttcttaagta aaatcaacgg aggcctcacc tcaatctcag     240
acttaccaaa gttaaacaag ttgagaaagc ttgaactaag cagtaacaga gtctcagggg     300
gcctggaagt attggcagaa aagtgtccaa acctcacgca tctatattta agtggcaaca     360
aaattaaaga cctcagcaca atagagccac tgaaacagtt agaaaacctc aagagcttag     420
acctttttcaa ttgcgaggta accaacctga acgactacgg agaaaacgtg ttcaagcttc     480
tcctgcaact cacatatctc gacagctgtt actgggacca aaggaggcc ccttactcag     540
atattgagga ccacgtggag ggcctggatg acgaggagga gggtgagcat gaggaggagt     600
atgatgaaga tgctcaggta gtggaagatg aggagggcga ggaggaggag gaggaaggtg     660
aagaggagga cgtgagtgga ggggacgggg aggatgaaga aggttataac gatggagagg     720
tagatggcga ggaagatgaa gaagagcttg gtgaagaaga aagggtcag aagcgaaaat     780
gagaacctga agatgaggga gaagatgatg actaagtaga ataacctatt ttgaaaaatt     840
cctattgtga tttgactgtt tttacccata tcccatctcc ccccccctc taatcctgcc     900
```

-continued

| ccctgaa | 907 |

<210> SEQ ID NO 17
<211> LENGTH: 907
<212> TYPE: DNA
<213> ORGANISM: Homo sapiens

<400> SEQUENCE: 17

| gggttcgggg tttattggtt gaattccgct ggctcaggag cctctgcaga gagaaagcgt | 60 |
| gagagatgga gatgggcaaa tggattcatt tagagctgcg gaacaggacg ccctccgatg | 120 |
| tgaaagaact tttcctggac aacagtcagt caaatgaagg caaattggaa ggcctcacag | 180 |
| atgaatttga ggaactggaa ttattaaata caatcaacat aggcctcacc tcaattgcaa | 240 |
| acttgccaaa gttaaacaaa cttaagaagc ttgaactaag cagtaacaga gcctcagtgg | 300 |
| gcctagaagt attggcagaa aagtgtccaa acctcataca tctaaattta agtggcaaca | 360 |
| aaattaaaga cctcagcaca atagagcccc tgaaaaagtt agaaaaccttt gagagcttag | 420 |
| accttttcac ttgcgaggta accaacctga caactactg agaaaagatg ttcaagctcc | 480 |
| tcctgcaact cacatatctc aacggctgtg acccggatga caaggaggcc cctaactcgg | 540 |
| atggtgaggg ctacgtggag ggcctggacg atgaggagga ggatgaggat gaggaggagt | 600 |
| atgatgaaga tgctcaggta gtggaagacg aggaggacga ggatgaggag gaggaaggtg | 660 |
| aagaggagga cgtgagtgga gaggaggagg aggatgaaga aggttataac gatggagagg | 720 |
| tagatgacga ggaagatgaa gaagagcttg gtgaagaaga aagggtcag aagcgaaaac | 780 |
| gagaacctga agatgaggga gaagatgatg actaagtgga ataacctatt tgaaaaatt | 840 |
| cctattgtga tttgactgtt tttagccgta tcccctctcc cccccactc taatcctgcc | 900 |
| ccctgaa | 907 |

<210> SEQ ID NO 18
<211> LENGTH: 907
<212> TYPE: DNA
<213> ORGANISM: Homo sapiens

<400> SEQUENCE: 18

| gggttcgggg tttattggtt gaattccgct ggctcaggag cctctgcaga gagaaagcgt | 60 |
| gagagatgga gatgggcaaa tggattcatt tagagctgcg gaacaggacg ccctccgatg | 120 |
| tgaaagaact tttcctggac aacagtcagt caaatgaagg caaattggaa ggcctcacag | 180 |
| atgaatttga agaactggaa ttattaaata caatcaacat aggcctcacc tcaattgcaa | 240 |
| acttgccaaa gttaaacaaa cttaagaagc ttgaactaag cagtaacaga gcctcagtgg | 300 |
| gcctagaagt attggcagaa aagtgtccaa acctcataca tctaaattta agtggcaaca | 360 |
| aaattaaaga cctcagcaca atagagcccc tgaaaaagtt agaaaacctc gagagcttag | 420 |
| accttttcac ttgcgaggta accaacctga caactactg agaaaagatg ttcaagctcc | 480 |
| tcctgcaact cacatatctc aacggctgtg acccggatga caaggaggcc cctaactcgg | 540 |
| atggtgaggg ctttgtggag tgcctggatg acaaggagga ggatgaggat gaggaggagt | 600 |
| atgatgaaga tgctcaggta atggaagatg aggaggacga ggatgaggag gaggaacgtg | 660 |
| aagaggagga cgtgagtgga gacgaggagg agaaggatga aggttataac aatggagagg | 720 |
| tagatgatga ggaagatgaa gaagagcttg gtgaagaaga aagggtcag aagcgaaaat | 780 |
| aagaaactga agatgaggga gaagacgatg cctaagtgga ataatctatt tgaaaaatt | 840 |
| ccttttgtga ttttactgtt tttagccgta tcccctctcc cccccactc taatcctgcc | 900 |

```
ccctgaa                                                                  907

<210> SEQ ID NO 19
<211> LENGTH: 907
<212> TYPE: DNA
<213> ORGANISM: Homo sapiens

<400> SEQUENCE: 19
gggttcgggg tttattgatt gaattcggct ggcacgagag cctctgcaga cagagagcgc         60
gagagatgga gatgggcaga cggattcatt cagagctgcg gaacagggcg ccctctgatg        120
tgaaagaact tgtcctggac aacagtcggt cgaatgaagg caaactcgaa gccctcacag        180
atgaatttga agaactggaa ttcttaagta aaatcaacgg aggcctcacc tcaatctcag        240
acttaccaaa gttaaacaag ttgagaaagc ttgaactaag cagtaacaaa gtctcagggg        300
gcctggaagt attggcagaa aagtgtccaa acctcacgca tctatattta agtggcaaca        360
aaattaaaga cctcagcaca atagagccac tgaaacagtt agaaaacctc aagagcttag        420
accttttcaa ttgcgaggta accaacctga cgactacgg agaaaacgtg ttcaagcttc         480
tcctgcaact cacatatctc gacagctgtt actgggacca caaggaggcc ccttactcag        540
atattgagga ccacgtggag ggcctggatg acgaggagga gggtgagcat gaggaggagt        600
atgatgaaga tgctcaggta gtggaagatg aggagggcga ggaggaggag gaggaaggtg        660
aagaggagga cgtgagtgga ggggacgagg aggatgaaga aggttataac gatggagagg        720
tagatggcga ggaagatgaa gaagagcttg gtgaagaaga aaggggtcag aagcgaaaat        780
gagaacctga agatgaggga gaagatgatg actaagtaga ataacctatt ttgaaaaatt        840
cctattgtga tttgactgtt tttacccata tccccctcc cccccctc taatcctgcc          900 ccctgaa                                                                  907

<210> SEQ ID NO 20
<211> LENGTH: 907
<212> TYPE: DNA
<213> ORGANISM: Homo sapiens

<400> SEQUENCE: 20
gggttcgggg tttattgatt gaattccgcc ggcgcgggag cctctgcaga gagggagcgc         60
gagagatgga gatgggcaga cggattcatt tagagctgcg gaacaggacg ccctctgatg        120
tgaaagaact tgtcctggac aacagtcggt cgaatgaagg caaactcgaa ggcctcacag        180
atgaatttga agaactggaa ttcttaagta caatcaacgt aggcctcacc tcaatcgcaa        240
acttaccaaa gttaaacaag ttgagaaagc ttgaactaag cagtaacaga gtctcagggg        300
gcctggaagt attggcagaa aagtgtccaa acctcacgca cctatattta agtggcaaca        360
aaattaaaga cctcagcaca atagagccac tgaaacagtt agaaaacctc aagagcttag        420
accttttcaa ttgcgaggta accaacctga cgactacgg agaaaacgtg ttcaagcttc         480
tcctgcaact cacatatctc gacagctgtt actgggacca caaggaggcc ccttactcag        540
atattgagga ccacgtggag ggcctggatg acgaggagga gggtgagcat gaggaggagt        600
atgatgaaga tgctcaggta gtggaagatg aggagggcga ggagggggag gaggaaggtg        660
aagaggagga cgtgagtgga ggggacgagg aggatgaaga aggttataac gatggagagg        720
tagatgacga ggaagatgaa gaagagcttg gtgaagaaga aaggggtcag aagcgaaaac        780
gagaacctga agatgaggga gaagatgatg actaagtgga ataacctatt ttgaaaaatt        840
```

-continued

```
cctattgtga tttgactgtt tttacccata tcccctctcc ccccccccctc taatcctgcc    900
ccctgaa                                                               907
```

<210> SEQ ID NO 21
<211> LENGTH: 907
<212> TYPE: DNA
<213> ORGANISM: Homo sapiens

<400> SEQUENCE: 21

```
gggttcgggg tttattgatt gaattccgcc ggcgcgggag cctctgcaga gagagagcgc     60
gagagatgga gatgggcaga cggattcatt tagagctgcg gaacaggacg ccctctgatg    120
tgaaagaact tgtcctggac aacagtcggt cgaatgaagg caaactcgag ggcctcacag    180
atgaatttga agaactggaa ttcttaagta caatcaacgt aggcctcacc tcaatcgcaa    240
acttaccaaa gttaaacaaa cttaagaagc ttgaactaag cgataacaga gtctcagggg    300
gcctggaagt attggcagaa aagtgtccga acctcacgca tctaaattta agtggcaaca    360
aaattaaaga cctcagcaca atagagccac tgaaaaagtt agaaaacctc aagagcttag    420
accttttcaa ttgcgaggta accaacctga acgactaccg agaaaatgtg ttcaagctcc    480
tcccgcaact cacatatctc gacggctatg accgggacga caaggaggcc cctgactcgg    540
atgctgaggg ctacgtggag ggcctggatg atgaggagga ggatgaggat gaggaggagt    600
atgatgaaga tgctcaggta gtggaagacg aggaggacga ggatgaggag gaggaaggtg    660
aagaggagga cgtgagtgga gaggaggagg aggatgaaga aggttataac gatggagagg    720
tagatgacga ggaagatgaa gaagagcttg gtgaagaaga aaggggtcag aagcgaaaac    780
gagaacctga agatgaggga gaagatgatg actaagtgga ataacctatt ttgaaaaatt    840
cctattgtga tttgactgtt tttacccata tcccctctcc ccccccccctc taatcctgcc    900
ccctgaa                                                               907
```

<210> SEQ ID NO 22
<211> LENGTH: 907
<212> TYPE: DNA
<213> ORGANISM: Homo sapiens

<400> SEQUENCE: 22

```
gggttcgggg tttattggtt gaattccgct ggctcaggag cctctgcaga gagaaagcgt     60
gagagatgga gatgggcaaa tggattcatt tagagctgcg gaacaggacg ccctccgatg    120
tgaaagaact tttcctggac aacagtcagt caaatgaagg caaattggaa ggcctcacag    180
atgaatttga agaactggaa ttattaaata caatcaacat aggcctcacc tcaattgcaa    240
acttgccaaa gttaaacaaa cttaagaagc ttgaactaag cagtaacaga gcctcagtgg    300
gcctagaagt attggcagaa aagtgtccaa acctcataca tctaaattta agtggcaaca    360
aaattaaaga cctcagcaca atagagcccc tgaaaaagtt agaaaacctc gagagcttag    420
accttttcac ttgcgaggta accaacctga acaactactg agaaaagatg ttcaagctcc    480
tcctgcaact cacatatctc aacggctgtg acccggatga caaggaggcc cctaactcgg    540
atggtgaggg ctttgtggag tgcctggatg acaaggagga ggatgaggat gaggaggagt    600
atgatgaaga tgctcaggta atggaagatg aggaggacga ggatgaggag gaggaacgtg    660
aagaggagga cgtgagtgga gacgaggagg agaaggatga aggttataac aatggagagg    720
tagatgatga ggaagatgaa gaagagcttg gtgaagaaga aaggggtcag aagcgaaaat    780
aagaaactga agatgaggga gaagacgatg cctaagtgga ataatctatt ttgaaaaatt    840
```

```
ccttttgtga ttttactgtt tttagccgta tccctctcc ccccccactc taatcctgcc      900
ccctgaa                                                                907

<210> SEQ ID NO 23
<211> LENGTH: 907
<212> TYPE: DNA
<213> ORGANISM: Homo sapiens

<400> SEQUENCE: 23
gggttcgggg tttattgatt gaattccgcc ggcgcgggag cctctgcaga gagagagcgc      60
gagagatgga gatgggcaga cggattcatc tagagctgcg aacaggacg  ccctctgatg     120 tgaaagaact tgtcctggtc aacagtcggt cgaatgaagg caaactcgaa ggcctcacag     180
atgaatttga agaactggaa ttcttaagta caatcaacgt aggcctcacc tcaatcgcaa     240
acttaccaaa gttaaacaaa cttaagaagc ttgaactaag cgataacaga gtctcagggg     300
gcctagaagt attggcagaa aagtgtccga acctcacgca tctaaattta agtggcaaca     360
aaattaaaga cctcagcaca atagagccac tgaaaaagtt agaaaacctc aagagcttag     420
accttttcaa ttgcgaggta accaacctga acgactaccg agaaaatgtg ttcaagctcc     480
tcccgcaact cacatatctc gacggctatg accgggacga caaggaggcc cctgactcgg     540
atgctgaggg ctacgtggag ggcctggatg atgaggagga ggatgaggat gaggaggagt     600
atgatgaaga tgctcaggta gtggaagacg aggaggacga ggatgaggag gaggaaggtg     660
aagaggagga cgtgagtgga gaggaggagg aggatgaaga aggttataac gatggagagg     720
tagatgacga ggaagatgaa gaagagcttg gtgaagaaga aagggggtcag aagcgaaaac     780 gagaacctga agatgaggga gaagatgatg actaagtgga ataacctatt ttgaaaaatt     840
cctattgtga tttgactgtt tttacccata tccctctcc ccccccctc taatcctgcc       900 ccctgaa                                                                907

<210> SEQ ID NO 24
<211> LENGTH: 907
<212> TYPE: DNA
<213> ORGANISM: Homo sapiens

<400> SEQUENCE: 24
gggttcgggg tttattgatt gaattccgcc ggcgcgggag cctctgcaga gagagagcgc      60
gagagatgga gatgggcaga cggattcatt tagagctgcg aacaggacg  ccctctgatg     120 tgaaagaact tgtcctggac aacagtcggt cgaatgaagg caaactcgaa ggcctcacag     180
atgaatttga agaactggaa ttcttaagta caatcaacgt aggcctcacc tcaatcgcaa     240
acttaccaaa gttaaacaaa cttaagaagc ttgaactaag cgataacaga gtctcagggg     300
gcctagaagt attggcagaa aagtgtccaa acctcataca tctaaattta agtggcaaca     360
aaattaaaga cctcagcaca atagagcccc tgaaaaagtt agaaaacctc gagagcttag     420
accttttcac ttgcgaggta accaacctga acaactactg agaaagatg  ttcaagctcc     480 tcctgcaact cacatatctc aacggctgtg acccggatga caaggaggcc cctaactcgg     540
atggtgaggg ctttgtggag tgcctggatg acaaggagga ggatgaggat gaggaggagt     600
atgatgaaga tgctcaggta atggaagatg aggaggacga ggatgaggag gaggaacgtg     660
aagaggagga cgtgagtgga gacgaggagg agaaggatga aggttataac aatggagagg     720
tagatgatga ggaagatgaa gaagagcttg gtgaagaaga aagggggtcag aagcgaaaat     780
```

-continued

| aagaaactga agatgaggga gaagacgatg cctaagtgga ataatctatt ttgaaaaatt | 840 |
| cctattgtga tttgactgtt tttacccata tcccctctcc cccccccctc taatcctgcc | 900 |
| ccctgaa | 907 |

<210> SEQ ID NO 25
<211> LENGTH: 908
<212> TYPE: DNA
<213> ORGANISM: Homo sapiens

<400> SEQUENCE: 25

| gggttcgggg tttattgatt gaattccgcc ggcgcgggag cctctgcaga gagagagcgc | 60 |
| ggagagatgg agatgggcag acggattcat ttagagctgc ggaacaggac gccctctgat | 120 |
| gtgaaagaac ttgtcctgga caacagtcgg tcgaatgaag caaaactcga aggcctcaca | 180 |
| gatgaatttg aagaactgga attcttaagt acaatcaacg taggcctcac ctcaatcgca | 240 |
| aacttaccaa agttaaacaa acttaagaag cttgaactaa gcgataacag agtctcaggg | 300 |
| ggcctggaag tattggcaga aaagtgtccg aacctcacgc atctaaattt aagtggcaac | 360 |
| aaaattaaag acctcagcac aatagagcca ctgaaaaagt tagaaaacct caagagctta | 420 |
| gacctttca attgcgaggt aaccaacctg aacgactacc gagaaaatgt gttcaagctc | 480 |
| ctcccgcaac tcacatatct cgacggctat gaccgggacg acaaggaggc ccctgactcg | 540 |
| gatgctgagg gctacgtgga gggcctggat gatgaggagg aggatgagga tgaggaggag | 600 |
| tatgatgaag atgctcaggt agtggaagac gaggaggacg aggatgagga ggaggaaggt | 660 |
| gaagaggagg acgtgagtgg agaggaggag gaggatgaag aaggttataa cgatggagag | 720 |
| gtagatgacg aggaagatga agaagagctt ggtgaagaag aaaggggtca gaagcgaaaa | 780 |
| cgagaacctg aagatgaggg agaagatgat gactaagtgg aataacctat tttgaaaaat | 840 |
| tcctattgtg atttgactgt ttttacccat atcccctctc ccccccccct ctaatcctgc | 900 |
| ccctgaa | 908 |

<210> SEQ ID NO 26
<211> LENGTH: 249
<212> TYPE: PRT
<213> ORGANISM: Homo sapiens

<400> SEQUENCE: 26

Met Glu Met Gly Arg Arg Ile His Leu Glu Leu Arg Asn Arg Thr Pro
1               5                   10                  15

Ser Asp Val Lys Glu Leu Val Leu Asp Asn Ser Arg Ser Asn Glu Gly
            20                  25                  30

Lys Leu Glu Gly Leu Thr Asp Glu Phe Glu Glu Leu Glu Phe Leu Ser
        35                  40                  45

Thr Ile Asn Val Gly Leu Thr Ser Ile Ala Asn Leu Pro Lys Leu Asn
    50                  55                  60

Lys Leu Lys Lys Leu Glu Leu Ser Ser Asn Arg Val Ser Gly Gly Leu
65                  70                  75                  80

Glu Val Leu Ala Glu Lys Cys Pro Asn Leu Ile His Leu Asn Leu Ser
                85                  90                  95

Gly Asn Lys Ile Lys Asp Leu Ser Thr Ile Glu Pro Leu Lys Lys Leu
            100                 105                 110

Glu Asn Leu Lys Ser Leu Asp Leu Phe Asn Cys Glu Val Thr Asn Leu
        115                 120                 125

Asn Asp Tyr Arg Glu Asn Val Phe Lys Leu Leu Pro Gln Leu Thr Tyr

```
                130                 135                 140
Leu Asp Gly Tyr Asp Arg Asp Asp Lys Glu Ala Pro Asp Ser Asp Ala
145                 150                 155                 160

Glu Gly Tyr Val Glu Gly Leu Asp Asp Glu Glu Asp Glu Asp Glu
                165                 170                 175

Glu Glu Tyr Asp Glu Asp Ala Gln Val Val Glu Asp Glu Glu Asp Glu
                180                 185                 190

Asp Glu Glu Glu Gly Glu Glu Asp Val Ser Gly Glu Glu
        195                 200                 205

Glu Asp Glu Glu Gly Tyr Asn Asp Gly Glu Val Asp Asp Glu Glu Asp
        210                 215                 220

Glu Glu Glu Leu Gly Glu Glu Arg Gly Gln Lys Arg Lys Arg Glu
225                 230                 235                 240

Pro Glu Asp Glu Gly Glu Asp Asp Asp
                245
```

<210> SEQ ID NO 27
<211> LENGTH: 249
<212> TYPE: PRT
<213> ORGANISM: Homo sapiens

<400> SEQUENCE: 27

```
Met Glu Met Gly Arg Arg Ile His Leu Glu Leu Arg Asn Arg Thr Pro
1               5                   10                  15

Ser Asp Val Lys Glu Leu Val Leu Asp Asn Ser Arg Ser Asn Glu Gly
                20                  25                  30

Lys Leu Glu Gly Leu Thr Asp Glu Phe Glu Glu Leu Glu Phe Leu Ser
                35                  40                  45

Thr Ile Asn Val Gly Leu Thr Ser Ile Ala Asn Leu Pro Lys Leu Asn
        50                  55                  60

Lys Leu Lys Lys Leu Glu Leu Ser Asp Asn Arg Val Ser Gly Gly Leu
65                  70                  75                  80

Glu Val Leu Ala Glu Lys Cys Pro Asn Leu Thr His Leu Asn Leu Ser
                85                  90                  95

Gly Asn Lys Ile Lys Asp Leu Ser Thr Ile Glu Pro Leu Lys Lys Leu
                100                 105                 110

Glu Asn Leu Lys Ser Leu Asp Leu Phe Asn Cys Glu Val Thr Asn Leu
                115                 120                 125

Asn Asp Tyr Arg Glu Asn Val Phe Lys Leu Leu Pro Gln Leu Thr Tyr
        130                 135                 140

Leu Asp Gly Tyr Asp Arg Asp Asp Lys Glu Ala Pro Asp Ser Asp Ala
145                 150                 155                 160

Glu Gly Tyr Val Glu Gly Leu Asp Asp Glu Glu Asp Glu Asp Glu
                165                 170                 175

Glu Glu Tyr Asp Glu Asp Ala Gln Val Val Glu Asp Glu Glu Asp Glu
                180                 185                 190

Asp Glu Glu Glu Gly Glu Glu Asp Val Ser Gly Glu Glu
        195                 200                 205

Glu Asp Glu Glu Gly Tyr Asn Asp Gly Glu Val Asp Asp Glu Glu Asp
        210                 215                 220

Glu Glu Glu Leu Gly Glu Glu Arg Gly Gln Lys Arg Lys Arg Glu
225                 230                 235                 240

Pro Glu Asp Glu Gly Glu Asp Asp Asp
                245
```

```
<210> SEQ ID NO 28
<211> LENGTH: 131
<212> TYPE: PRT
<213> ORGANISM: Homo sapiens

<400> SEQUENCE: 28

Met Glu Met Gly Arg Arg Ile His Leu Glu Leu Arg Asn Gly Thr Pro
1               5                   10                  15

Ser Asp Val Lys Glu Leu Val Leu Asp Asn Ser Arg Ser Asn Glu Gly
            20                  25                  30

Lys Leu Glu Gly Leu Thr Asp Glu Phe Glu Leu Glu Phe Leu Ser
        35                  40                  45

Thr Ile Asn Val Gly Leu Thr Ser Ile Ala Asn Leu Pro Lys Leu Asn
    50                  55                  60

Lys Leu Lys Lys Leu Glu Leu Ser Ser Asn Arg Ala Ser Val Gly Leu
65                  70                  75                  80

Glu Val Leu Ala Glu Lys Cys Pro Asn Leu Ile His Leu Asn Leu Ser
                85                  90                  95

Gly Asn Lys Ile Lys Asp Leu Ser Thr Ile Glu Pro Leu Lys Lys Leu
            100                 105                 110

Glu Asn Leu Glu Ser Leu Asp Leu Phe Thr Cys Glu Val Thr Asn Leu
        115                 120                 125

Asn Asn Tyr
    130

<210> SEQ ID NO 29
<211> LENGTH: 131
<212> TYPE: PRT
<213> ORGANISM: Homo sapiens

<400> SEQUENCE: 29

Met Glu Met Gly Lys Trp Ile His Leu Glu Leu Arg Asn Arg Thr Pro
1               5                   10                  15

Ser Asp Val Lys Glu Leu Phe Leu Asp Asn Ser Gln Ser Asn Glu Gly
            20                  25                  30

Lys Leu Glu Gly Leu Thr Asp Glu Phe Glu Glu Leu Glu Leu Leu Asn
        35                  40                  45

Thr Ile Asn Ile Gly Leu Thr Ser Ile Ala Asn Leu Pro Lys Leu Asn
    50                  55                  60

Lys Leu Lys Lys Leu Glu Leu Ser Ser Asn Arg Ala Ser Val Gly Leu
65                  70                  75                  80

Glu Val Leu Ala Glu Lys Cys Pro Asn Leu Ile His Leu Asn Leu Ser
                85                  90                  95

Gly Asn Lys Ile Lys Asp Leu Ser Thr Ile Glu Pro Leu Lys Lys Leu
            100                 105                 110

Glu Asn Leu Glu Ser Leu Asp Leu Phe Thr Cys Glu Val Thr Asn Leu
        115                 120                 125

Asn Asn Tyr
    130

<210> SEQ ID NO 30
<211> LENGTH: 249
<212> TYPE: PRT
<213> ORGANISM: Homo sapiens

<400> SEQUENCE: 30

Met Glu Met Gly Arg Arg Ile His Leu Glu Leu Arg Asn Arg Thr Pro
```

```
                1               5                    10                   15
Ser Asp Val Lys Glu Leu Val Leu Asp Asn Ser Arg Ser Asn Glu Gly
                20                   25                   30

Lys Leu Glu Gly Leu Thr Asp Glu Phe Glu Glu Leu Glu Phe Leu Ser
                35                   40                   45

Thr Ile Asn Val Gly Leu Thr Ser Ile Ala Asn Leu Pro Lys Leu Asn
                50                   55                   60

Lys Leu Lys Lys Leu Glu Leu Ser Ser Asn Arg Ala Ser Val Gly Leu
65                   70                   75                   80

Glu Val Leu Ala Glu Lys Cys Pro Asn Leu Ile His Leu Asn Leu Ser
                85                   90                   95

Gly Asn Lys Ile Lys Asp Leu Ser Thr Ile Glu Pro Leu Lys Lys Leu
                100                  105                  110

Glu Asn Leu Lys Ser Leu Asp Leu Ser Asn Cys Glu Val Thr Asn Leu
                115                  120                  125

Asn Asp Tyr Arg Glu Asn Val Phe Lys Leu Leu Pro Gln Leu Thr Tyr
                130                  135                  140

Leu Asp Gly Tyr Asp Arg Asp Asp Lys Glu Ala Pro Asp Ser Asp Ala
145                  150                  155                  160

Glu Gly Tyr Val Glu Gly Leu Asp Asp Glu Glu Asp Glu Asp Glu
                165                  170                  175

Glu Glu Tyr Asp Glu Asp Ala Gln Val Val Glu Asp Glu Glu Asp Glu
                180                  185                  190

Asp Glu Glu Glu Glu Gly Glu Glu Asp Val Ser Gly Glu Glu Glu
                195                  200                  205

Glu Asp Glu Glu Gly Tyr Asn Asp Gly Glu Val Asp Asp Glu Glu Asp
                210                  215                  220

Glu Glu Glu Leu Gly Glu Glu Arg Gly Gln Lys Arg Lys Arg Glu
225                  230                  235                  240

Pro Glu Asp Glu Gly Glu Asp Asp Asp
                245
```

<210> SEQ ID NO 31
<211> LENGTH: 249
<212> TYPE: PRT
<213> ORGANISM: Homo sapiens

<400> SEQUENCE: 31

```
Met Glu Met Gly Lys Trp Ile His Leu Glu Leu Arg Asn Arg Thr Pro
1               5                    10                   15

Ser Asp Val Lys Glu Leu Phe Leu Asp Asn Ser Gln Ser Asn Glu Gly
                20                   25                   30

Lys Leu Glu Gly Leu Thr Asp Glu Phe Glu Glu Leu Glu Leu Leu Asn
                35                   40                   45

Thr Ile Asn Ile Gly Leu Thr Ser Ile Ala Asn Leu Pro Lys Leu Asn
                50                   55                   60

Lys Leu Lys Lys Leu Glu Leu Ser Ser Asn Arg Ala Ser Val Gly Leu
65                   70                   75                   80

Glu Val Leu Ala Glu Lys Cys Pro Asn Leu Ile His Leu Asn Leu Ser
                85                   90                   95

Gly Asn Lys Ile Lys Asp Leu Ser Thr Ile Glu Pro Leu Lys Lys Leu
                100                  105                  110

Glu Asn Leu Glu Ser Leu Asp Leu Phe Thr Cys Glu Val Thr Asn Leu
                115                  120                  125
```

```
Asn Asn Tyr Arg Glu Asn Val Phe Lys Leu Leu Pro Gln Leu Thr Tyr
    130                 135                 140

Leu Asp Gly Tyr Asp Arg Asp Asp Lys Glu Ala Pro Asp Ser Asp Ala
145                 150                 155                 160

Glu Gly Tyr Val Glu Gly Leu Asp Asp Glu Glu Asp Glu Asp Glu Asp
                165                 170                 175

Glu Glu Tyr Asp Glu Asp Ala Gln Val Val Glu Asp Glu Glu Asp Glu
                180                 185                 190

Asp Glu Glu Glu Gly Glu Glu Asp Val Ser Gly Glu Glu Glu
            195                 200                 205

Glu Asp Glu Glu Gly Tyr Asn Asp Gly Glu Val Asp Asp Glu Glu Asp
    210                 215                 220

Glu Glu Glu Leu Gly Glu Glu Arg Gly Gln Lys Arg Lys Arg Glu
225                 230                 235                 240

Pro Glu Asp Glu Gly Glu Asp Asp Asp
                245

<210> SEQ ID NO 32
<211> LENGTH: 238
<212> TYPE: PRT
<213> ORGANISM: Homo sapiens

<400> SEQUENCE: 32

Met Glu Met Gly Arg Arg Ile His Ser Glu Leu Arg Asn Arg Ala Pro
1               5                   10                  15

Ser Asp Val Lys Glu Leu Ala Leu Asp Asn Ser Arg Ser Asn Glu Gly
            20                  25                  30

Lys Leu Glu Ala Leu Thr Asp Glu Phe Glu Glu Leu Glu Phe Leu Ser
        35                  40                  45

Lys Ile Asn Gly Gly Leu Thr Ser Ile Ser Asp Leu Pro Lys Leu Asn
    50                  55                  60

Lys Leu Arg Lys Leu Glu Leu Ser Ser Asn Arg Val Ser Gly Gly Leu
65                  70                  75                  80

Glu Val Leu Ala Glu Lys Cys Pro Asn Leu Thr His Leu Tyr Leu Ser
                85                  90                  95

Gly Asn Lys Ile Lys Asp Leu Ser Thr Ile Glu Pro Leu Lys Gln Leu
            100                 105                 110

Glu Asn Leu Lys Ser Leu Asp Leu Phe Asn Cys Glu Val Thr Asn Leu
        115                 120                 125

Asn Asp Tyr Gly Glu Asn Val Phe Lys Leu Leu Leu Gln Leu Thr Tyr
    130                 135                 140

Leu Asp Ser Cys Tyr Trp Asp His Lys Glu Ala Pro Tyr Ser Asp Ile
145                 150                 155                 160

Glu Asp His Val Glu Gly Leu Asp Asp Glu Glu Gly Glu His Glu
                165                 170                 175

Glu Glu Tyr Asp Glu Asp Ala Gln Val Val Glu Asp Glu Glu Gly Glu
                180                 185                 190

Glu Glu Glu Glu Gly Glu Glu Asp Val Ser Gly Gly Asp Gly
            195                 200                 205

Glu Asp Glu Glu Gly Tyr Asn Asp Gly Glu Val Asp Gly Glu Glu Asp
    210                 215                 220

Glu Glu Glu Leu Gly Glu Glu Arg Gly Gln Lys Arg Lys
225                 230                 235

<210> SEQ ID NO 33
```

```
<211> LENGTH: 131
<212> TYPE: PRT
<213> ORGANISM: Homo sapiens

<400> SEQUENCE: 33

Met Glu Met Gly Lys Trp Ile His Leu Glu Leu Arg Asn Arg Thr Pro
1               5                   10                  15

Ser Asp Val Lys Glu Leu Phe Leu Asp Asn Ser Gln Ser Asn Glu Gly
            20                  25                  30

Lys Leu Glu Gly Leu Thr Asp Glu Phe Glu Glu Leu Glu Leu Leu Asn
        35                  40                  45

Thr Ile Asn Ile Gly Leu Thr Ser Ile Ala Asn Leu Pro Lys Leu Asn
    50                  55                  60

Lys Leu Lys Lys Leu Glu Leu Ser Ser Asn Arg Ala Ser Val Gly Leu
65                  70                  75                  80

Glu Val Leu Ala Glu Lys Cys Pro Asn Leu Ile His Leu Asn Leu Ser
                85                  90                  95

Gly Asn Lys Ile Lys Asp Leu Ser Thr Ile Glu Pro Leu Lys Lys Leu
            100                 105                 110

Glu Asn Leu Glu Ser Leu Asp Leu Phe Thr Cys Glu Val Thr Asn Leu
        115                 120                 125

Asn Asn Tyr
    130

<210> SEQ ID NO 34
<211> LENGTH: 238
<212> TYPE: PRT
<213> ORGANISM: Homo sapiens

<400> SEQUENCE: 34

Met Glu Met Gly Arg Arg Ile His Ser Glu Leu Arg Asn Arg Ala Pro
1               5                   10                  15

Ser Asp Val Lys Glu Leu Val Leu Asp Asn Ser Arg Ser Asn Glu Gly
            20                  25                  30

Lys Leu Glu Ala Leu Thr Asp Glu Phe Glu Glu Leu Glu Phe Leu Ser
        35                  40                  45

Lys Ile Asn Gly Gly Leu Thr Ser Ile Ser Asp Leu Pro Lys Leu Asn
    50                  55                  60

Lys Leu Arg Lys Leu Glu Leu Ser Ser Asn Lys Val Ser Gly Gly Leu
65                  70                  75                  80

Glu Val Leu Ala Glu Lys Cys Pro Asn Leu Thr His Leu Tyr Leu Ser
                85                  90                  95

Gly Asn Lys Ile Lys Asp Leu Ser Thr Ile Glu Pro Leu Lys Gln Leu
            100                 105                 110

Glu Asn Leu Lys Ser Leu Asp Leu Phe Asn Cys Glu Val Thr Asn Leu
        115                 120                 125

Asn Asp Tyr Gly Glu Asn Val Phe Lys Leu Leu Gln Leu Thr Tyr
    130                 135                 140

Leu Asp Ser Cys Tyr Trp Asp His Lys Glu Ala Pro Tyr Ser Asp Ile
145                 150                 155                 160

Glu Asp His Val Glu Gly Leu Asp Asp Glu Glu Gly Glu His Glu
                165                 170                 175

Glu Glu Tyr Asp Glu Asp Ala Gln Val Val Glu Asp Glu Gly Glu
            180                 185                 190

Glu Glu Glu Glu Glu Gly Glu Glu Glu Asp Val Ser Gly Gly Asp Glu
        195                 200                 205
```

-continued

```
Glu Asp Glu Glu Gly Tyr Asn Asp Gly Glu Val Asp Gly Glu Glu Asp
    210                 215                 220
Glu Glu Glu Leu Gly Glu Glu Arg Gly Gln Lys Arg Lys
225                 230                 235

<210> SEQ ID NO 35
<211> LENGTH: 249
<212> TYPE: PRT
<213> ORGANISM: Homo sapiens

<400> SEQUENCE: 35

Met Glu Met Gly Arg Arg Ile His Leu Glu Leu Arg Asn Arg Thr Pro
1               5                   10                  15
Ser Asp Val Lys Glu Leu Val Leu Asp Asn Ser Arg Ser Asn Glu Gly
                20                  25                  30
Lys Leu Glu Gly Leu Thr Asp Glu Phe Glu Glu Leu Glu Phe Leu Ser
            35                  40                  45
Thr Ile Asn Val Gly Leu Thr Ser Ile Ala Asn Leu Pro Lys Leu Asn
        50                  55                  60
Lys Leu Arg Lys Leu Glu Leu Ser Ser Asn Arg Val Ser Gly Gly Leu
65                  70                  75                  80
Glu Val Leu Ala Glu Lys Cys Pro Asn Leu Thr His Leu Tyr Leu Ser
                85                  90                  95
Gly Asn Lys Ile Lys Asp Leu Ser Thr Ile Glu Pro Leu Lys Gln Leu
            100                 105                 110
Glu Asn Leu Lys Ser Leu Asp Leu Phe Asn Cys Glu Val Thr Asn Leu
        115                 120                 125
Asn Asp Tyr Gly Glu Asn Val Phe Lys Leu Leu Gln Leu Thr Tyr
    130                 135                 140
Leu Asp Ser Cys Tyr Trp Asp His Lys Glu Ala Pro Tyr Ser Asp Ile
145                 150                 155                 160
Glu Asp His Val Glu Gly Leu Asp Asp Glu Glu Gly Glu His Glu
                165                 170                 175
Glu Glu Tyr Asp Glu Asp Ala Gln Val Val Asp Glu Glu Gly Glu
            180                 185                 190
Glu Gly Glu Glu Glu Gly Glu Glu Asp Val Ser Gly Gly Asp Glu
        195                 200                 205
Glu Asp Glu Glu Gly Tyr Asn Asp Gly Glu Val Asp Asp Glu Glu Asp
    210                 215                 220
Glu Glu Glu Leu Gly Glu Glu Arg Gly Gln Lys Arg Lys Arg Glu
225                 230                 235                 240
Pro Glu Asp Glu Gly Glu Asp Asp
                245

<210> SEQ ID NO 36
<211> LENGTH: 249
<212> TYPE: PRT
<213> ORGANISM: Homo sapiens

<400> SEQUENCE: 36

Met Glu Met Gly Arg Arg Ile His Leu Glu Leu Arg Asn Arg Thr Pro
1               5                   10                  15
Ser Asp Val Lys Glu Leu Val Leu Val Asn Ser Arg Ser Asn Glu Gly
                20                  25                  30
Lys Leu Glu Gly Leu Thr Asp Glu Phe Glu Glu Leu Glu Phe Leu Ser
            35                  40                  45
```

```
Thr Ile Asn Val Gly Leu Thr Ser Ile Ala Asn Leu Pro Lys Leu Asn
        50                  55                  60

Lys Leu Lys Lys Leu Glu Leu Ser Asp Asn Arg Val Ser Gly Gly Leu
65                  70                  75                  80

Glu Val Leu Ala Glu Lys Cys Pro Asn Leu Thr His Leu Asn Leu Ser
                85                  90                  95

Gly Asn Lys Ile Lys Asp Leu Ser Thr Ile Glu Pro Leu Lys Lys Leu
            100                 105                 110

Glu Asn Leu Lys Ser Leu Asp Leu Phe Asn Cys Glu Val Thr Asn Leu
        115                 120                 125

Asn Asp Tyr Arg Glu Asn Val Phe Lys Leu Leu Pro Gln Leu Thr Tyr
    130                 135                 140

Leu Asp Gly Tyr Asp Arg Asp Asp Lys Glu Ala Pro Asp Ser Asp Ala
145                 150                 155                 160

Glu Gly Tyr Val Glu Gly Leu Asp Asp Glu Glu Asp Glu Asp Glu
                165                 170                 175

Glu Glu Tyr Asp Glu Asp Ala Gln Val Val Glu Asp Glu Glu Asp Glu
            180                 185                 190

Asp Glu Glu Glu Gly Glu Glu Asp Val Ser Gly Glu Glu Glu
        195                 200                 205

Glu Asp Glu Glu Gly Tyr Asn Asp Gly Glu Val Asp Asp Glu Glu Asp
        210                 215                 220

Glu Glu Glu Leu Gly Glu Glu Glu Arg Gly Gln Lys Arg Lys Arg Glu
225                 230                 235                 240

Pro Glu Asp Glu Gly Glu Asp Asp
                245

<210> SEQ ID NO 37
<211> LENGTH: 131
<212> TYPE: PRT
<213> ORGANISM: Homo sapiens

<400> SEQUENCE: 37

Met Glu Met Gly Arg Arg Ile His Leu Glu Leu Arg Asn Arg Thr Pro
1               5                   10                  15

Ser Asp Val Lys Glu Leu Val Leu Asp Asn Ser Arg Ser Asn Glu Gly
                20                  25                  30

Lys Leu Glu Gly Leu Thr Asp Glu Phe Glu Glu Leu Glu Phe Leu Ser
            35                  40                  45

Thr Ile Asn Val Gly Leu Thr Ser Ile Ala Asn Leu Pro Lys Leu Asn
        50                  55                  60

Lys Leu Lys Lys Leu Glu Leu Ser Asp Asn Arg Val Ser Gly Gly Leu
65                  70                  75                  80

Glu Val Leu Ala Glu Lys Cys Pro Asn Leu Ile His Leu Asn Leu Ser
                85                  90                  95

Gly Asn Lys Ile Lys Asp Leu Ser Thr Ile Glu Pro Leu Lys Lys Leu
            100                 105                 110

Glu Asn Leu Glu Ser Leu Asp Leu Phe Thr Cys Glu Val Thr Asn Leu
        115                 120                 125

Asn Asn Tyr
    130

<210> SEQ ID NO 38
<211> LENGTH: 131
<212> TYPE: PRT
```

```
<213> ORGANISM: Homo sapiens

<400> SEQUENCE: 38

Met Glu Met Gly Lys Trp Ile His Leu Glu Leu Arg Asn Arg Thr Pro
1               5                   10                  15

Ser Asp Val Lys Glu Leu Phe Leu Asp Asn Ser Gln Ser Asn Glu Gly
                20                  25                  30

Lys Leu Glu Gly Leu Ala Asp Glu Phe Glu Glu Leu Glu Leu Leu Asn
            35                  40                  45

Thr Ile Asn Ile Gly Leu Ser Ser Ile Ala Asn Leu Ala Lys Leu Asn
    50                  55                  60

Lys Leu Lys Lys Leu Glu Leu Ser Ser Asn Arg Ala Ser Val Gly Leu
65                  70                  75                  80

Glu Val Leu Ala Glu Lys Cys Pro Asn Leu Ile His Leu Asn Leu Ser
                85                  90                  95

Gly Asn Lys Ile Lys Asp Leu Ser Thr Ile Glu Pro Leu Lys Lys Leu
            100                 105                 110

Glu Asn Leu Glu Ser Leu Asp Leu Phe Thr Cys Glu Val Thr Asn Leu
        115                 120                 125

Asn Asn Tyr
    130

<210> SEQ ID NO 39
<211> LENGTH: 234
<212> TYPE: PRT
<213> ORGANISM: Homo sapiens

<400> SEQUENCE: 39

Met Glu Met Gly Arg Arg Ile His Ser Glu Leu Arg Asn Arg Ala Pro
1               5                   10                  15

Ser Asp Val Lys Glu Leu Val Leu Asp Asn Ser Arg Ser Asn Glu Gly
                20                  25                  30

Lys Leu Glu Ala Leu Thr Asp Glu Phe Glu Glu Leu Glu Phe Leu Ser
            35                  40                  45

Lys Ile Asn Gly Gly Leu Thr Ser Ile Ser Asp Leu Pro Lys Leu Lys
    50                  55                  60

Leu Arg Lys Leu Glu Leu Lys Val Ser Gly Gly Leu Glu Val Leu Ala
65                  70                  75                  80

Glu Lys Cys Pro Asn Leu Thr His Leu Tyr Leu Ser Gly Asn Lys Ile
                85                  90                  95

Lys Asp Leu Ser Thr Ile Glu Pro Leu Lys Gln Leu Glu Asn Leu Lys
            100                 105                 110

Ser Leu Asp Leu Phe Asn Cys Glu Val Thr Asn Leu Asn Asp Tyr Gly
        115                 120                 125

Glu Asn Val Phe Lys Leu Leu Leu Gln Leu Thr Tyr Leu Asp Ser Cys
    130                 135                 140

Tyr Trp Asp His Lys Glu Ala Pro Tyr Ser Asp Ile Glu Asp His Val
145                 150                 155                 160

Glu Gly Leu Asp Asp Glu Glu Gly Glu His Glu Glu Glu Tyr Asp
                165                 170                 175

Glu Asp Ala Gln Val Val Glu Asp Glu Glu Gly Glu Glu Glu Glu
            180                 185                 190

Glu Gly Glu Glu Glu Asp Val Ser Gly Gly Asp Glu Glu Asp Glu Glu
        195                 200                 205

Gly Tyr Asn Asp Gly Glu Val Asp Gly Glu Glu Asp Glu Glu Glu Leu
```

```
              210                 215                 220
Gly Glu Glu Glu Arg Gly Gln Lys Arg Lys
225                 230
```

<210> SEQ ID NO 40
<211> LENGTH: 249
<212> TYPE: PRT
<213> ORGANISM: Homo sapiens

<400> SEQUENCE: 40

```
Met Glu Met Gly Arg Arg Ile His Leu Glu Leu Arg Asn Arg Thr Pro
1               5                   10                  15

Ser Asp Val Lys Glu Leu Val Leu Asp Asn Ser Arg Ser Asn Glu Gly
            20                  25                  30

Lys Leu Glu Gly Leu Thr Asp Glu Phe Glu Glu Leu Glu Phe Leu Ser
        35                  40                  45

Thr Ile Asn Val Gly Leu Thr Ser Ile Ala Asn Leu Pro Lys Leu Asn
    50                  55                  60

Lys Leu Lys Lys Leu Glu Leu Ser Asp Asn Arg Val Ser Gly Gly Leu
65                  70                  75                  80

Glu Val Leu Ala Glu Lys Cys Pro Asn Leu Thr His Leu Asn Leu Ser
                85                  90                  95

Gly Asn Lys Ile Lys Asp Leu Ser Thr Ile Glu Pro Leu Lys Lys Leu
            100                 105                 110

Glu Asn Leu Lys Ser Leu Asp Leu Phe Asn Cys Glu Val Thr Asn Leu
        115                 120                 125

Asn Asp Tyr Arg Glu Asn Val Phe Lys Leu Leu Pro Gln Leu Thr Tyr
    130                 135                 140

Leu Asp Gly Tyr Asp Arg Asp Asp Lys Glu Ala Pro Asp Ser Asp Ala
145                 150                 155                 160

Glu Gly Tyr Val Glu Gly Leu Asp Asp Glu Glu Asp Glu Asp Glu
                165                 170                 175

Glu Glu Tyr Asp Glu Asp Ala Gln Val Val Glu Asp Glu Glu Asp Glu
            180                 185                 190

Asp Glu Glu Glu Gly Glu Glu Asp Val Ser Gly Glu Glu Glu
        195                 200                 205

Glu Asp Glu Glu Gly Tyr Asn Asp Gly Glu Val Asp Asp Glu Glu Asp
            210                 215                 220

Glu Glu Glu Leu Gly Glu Glu Arg Gly Gln Lys Arg Lys Arg Glu
225                 230                 235                 240

Pro Glu Asp Glu Gly Glu Asp Asp
                245
```

<210> SEQ ID NO 41
<211> LENGTH: 26
<212> TYPE: DNA
<213> ORGANISM: Homo sapiens

<400> SEQUENCE: 41
tatgctagcg ggttcggggt ttattg                                      26

<210> SEQ ID NO 42
<211> LENGTH: 29
<212> TYPE: DNA
<213> ORGANISM: Homo sapiens

<400> SEQUENCE: 42
gattctagat ggtaagtttg cgattgagg 29

<210> SEQ ID NO 43
<211> LENGTH: 29
<212> TYPE: DNA
<213> ORGANISM: Homo sapiens

<400> SEQUENCE: 43
gaatctagaa ggaggaggaa ggtgaagag 29

<210> SEQ ID NO 44
<211> LENGTH: 29
<212> TYPE: DNA
<213> ORGANISM: Homo sapiens

<400> SEQUENCE: 44
ctatctagat tcaggggggca ggattagag 29

<210> SEQ ID NO 45
<211> LENGTH: 24
<212> TYPE: DNA
<213> ORGANISM: Homo sapiens

<400> SEQUENCE: 45
gaggtttatt gattgaattc ggct 24

<210> SEQ ID NO 46
<211> LENGTH: 24
<212> TYPE: DNA
<213> ORGANISM: Homo sapiens

<400> SEQUENCE: 46
ccccagtaca cttttcccgt ctca 24

<210> SEQ ID NO 47
<211> LENGTH: 17
<212> TYPE: DNA
<213> ORGANISM: Homo sapiens

<400> SEQUENCE: 47
gggttcgggg tttattg 17

<210> SEQ ID NO 48
<211> LENGTH: 20
<212> TYPE: DNA
<213> ORGANISM: Homo sapiens

<400> SEQUENCE: 48
ctctaatcct gcccctgaa 20

<210> SEQ ID NO 49
<211> LENGTH: 12
<212> TYPE: DNA
<213> ORGANISM: Artificial Sequence
<220> FEATURE:
<223> OTHER INFORMATION: Recognition sequence

<400> SEQUENCE: 49
tttttctttt tc 12

<210> SEQ ID NO 50
<211> LENGTH: 10
<212> TYPE: DNA
<213> ORGANISM: Artificial Sequence

```
-continued

<220> FEATURE:
<223> OTHER INFORMATION: Recognition Sequence

<400> SEQUENCE: 50
ttaaaattca                                                            10

<210> SEQ ID NO 51
<211> LENGTH: 10
<212> TYPE: DNA
<213> ORGANISM: Artificial Sequence
<220> FEATURE:
<223> OTHER INFORMATION: Recognition Sequence

<400> SEQUENCE: 51
atgtaaaaca                                                            10

<210> SEQ ID NO 52
<211> LENGTH: 11
<212> TYPE: DNA
<213> ORGANISM: Artificial Sequence
<220> FEATURE:
<223> OTHER INFORMATION: Recognition Sequence

<400> SEQUENCE: 52
aagataaaac c                                                          11

<210> SEQ ID NO 53
<211> LENGTH: 10
<212> TYPE: DNA
<213> ORGANISM: Artificial Sequence
<220> FEATURE:
<223> OTHER INFORMATION: Recognition Sequence

<400> SEQUENCE: 53
ccactgggga                                                            10

<210> SEQ ID NO 54
<211> LENGTH: 13
<212> TYPE: DNA
<213> ORGANISM: Artificial Sequence
<220> FEATURE:
<223> OTHER INFORMATION: Recognition Sequence

<400> SEQUENCE: 54
ctctctctct ctc                                                        13

<210> SEQ ID NO 55
<211> LENGTH: 11
<212> TYPE: DNA
<213> ORGANISM: Artificial Sequence
<220> FEATURE:
<223> OTHER INFORMATION: Recognition Sequence

<400> SEQUENCE: 55
aaaacataaa t                                                          11
```